(12) United States Patent
Liu

(10) Patent No.: US 11,190,752 B2
(45) Date of Patent: *Nov. 30, 2021

(54) OPTICAL IMAGING SYSTEM AND METHODS THEREOF

(71) Applicant: THE UNIVERSITY OF AKRON, Akron, OH (US)

(72) Inventor: Yang Liu, Iowa City, OH (US)

(73) Assignee: THE UNIVERSITY OF AKRON, Akron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/238,737

(22) Filed: Apr. 23, 2021

(65) Prior Publication Data

US 2021/0243425 A1 Aug. 5, 2021

Related U.S. Application Data

(63) Continuation of application No. 16/858,887, filed on Apr. 27, 2020, now Pat. No. 10,992,922, which is a
(Continued)

(51) Int. Cl.
*H04N 13/254* (2018.01)
*A61B 6/03* (2006.01)
(Continued)

(52) U.S. Cl.
CPC ....... *H04N 13/254* (2018.05); *A61B 1/00006* (2013.01); *A61B 1/045* (2013.01);
(Continued)

(58) Field of Classification Search
CPC .. H04N 13/254; H04N 13/271; H04N 13/296; H04N 13/246; H04N 5/33;
(Continued)

(56) References Cited

U.S. PATENT DOCUMENTS 6,377,910 B1 4/2002 Hsu et al. ............ 703/20
6,485,413 B1 11/2002 Boppart et al. ........ 600/160
(Continued)

OTHER PUBLICATIONS

International Search Report dated Jun. 24, 2016 in related application No. PCT/US2016/016991.
(Continued)

*Primary Examiner* — John R Schnurr
(74) *Attorney, Agent, or Firm* — Renner Kenner Greive Bobak Taylor & Weber

(57) ABSTRACT

An optical imaging system to image a target object includes a light source configured to emit one or more light rays to illuminate the target object and an image detector configured to capture a three-dimensional topography image of the target object when emitted light is emitted from the target object in response to being illuminated by the light rays emitted by the light source. A fluorescence image detector captures a fluorescence image of the target object when fluorescence is emitted from the target object in response illumination by light rays emitted by the light source. A controller instructs the image detector to capture the 3D topography image and the fluorescence image detector to detect the fluorescence image of the target object intraoperatively and to co-register and simultaneously display intraoperatively the co-registered topography and fluorescence information to the user via a display.

20 Claims, 39 Drawing Sheets

Related U.S. Application Data continuation of application No. 15/547,590, filed as application No. PCT/US2016/016991 on Feb. 8, 2016, now Pat. No. 10,666,928.

(60) Provisional application No. 62/112,993, filed on Feb. 6, 2015.

(51) Int. Cl.

| | | |
|---|---|---|
| *A61B 6/00* | (2006.01) | |
| *G06T 7/30* | (2017.01) | |
| *G06K 9/00* | (2006.01) | |
| *A61B 5/00* | (2006.01) | |
| *A61B 90/00* | (2016.01) | |
| *G06T 7/37* | (2017.01) | |
| *H04N 13/246* | (2018.01) | |
| *H04N 13/271* | (2018.01) | |
| *H04N 13/296* | (2018.01) | |
| *A61B 1/00* | (2006.01) | |
| *A61B 1/045* | (2006.01) | |
| *A61B 1/07* | (2006.01) | |
| *A61B 5/055* | (2006.01) | |
| *H04N 5/33* | (2006.01) | |
| *A61B 34/10* | (2016.01) | |

(52) U.S. Cl.
CPC .............. *A61B 1/07* (2013.01); *A61B 5/0064* (2013.01); *A61B 5/0071* (2013.01); *A61B 5/055* (2013.01); *A61B 6/032* (2013.01); *A61B 6/037* (2013.01); *A61B 6/508* (2013.01); *A61B 6/5247* (2013.01); *A61B 90/37* (2016.02); *G06K 9/00201* (2013.01); *G06T 7/30* (2017.01); *G06T 7/37* (2017.01); *H04N 5/33* (2013.01); *H04N 13/246* (2018.05); *H04N 13/271* (2018.05); *H04N 13/296* (2018.05); *A61B 5/0075* (2013.01); *A61B 5/7285* (2013.01); *A61B 5/7425* (2013.01); *A61B 5/7445* (2013.01); *A61B 2034/105* (2016.02); *A61B 2090/373* (2016.02); *G06K 2209/05* (2013.01); *G06T 2207/10028* (2013.01); *G06T 2207/10064* (2013.01); *G06T 2207/10072* (2013.01); *G06T 2207/10076* (2013.01); *G06T 2207/10081* (2013.01); *G06T 2207/10088* (2013.01); *G06T 2207/10104* (2013.01); *G06T 2207/10108* (2013.01)

(58) Field of Classification Search
CPC ......... A61B 1/045; A61B 5/055; A61B 6/032; A61B 5/0064; A61B 1/00006; A61B 90/37; A61B 6/037; A61B 1/07; A61B 6/5247; A61B 6/508; A61B 5/0071; A61B 5/7285; A61B 5/0075; A61B 5/7445; A61B 2034/105; A61B 2090/373; A61B 5/7425; G06K 9/00201; G06K 2209/05; G06T 7/30; G06T 7/37; G06T 2207/10064; G06T 2207/10088; G06T 2207/10081; G06T 2207/10028; G06T 2207/10076; G06T 2207/10108; G06T 2207/10072; G06T 2207/10104

See application file for complete search history.

(56) References Cited

U.S. PATENT DOCUMENTS

| | | | |
|---|---|---|---|
| 6,774,370 B1 | 8/2004 | Uchida et al. | 250/363.03 |
| 2001/0055462 A1* | 12/2001 | Seibel | A61B 1/00172 385/147 |
| 2007/0210244 A1 | 9/2007 | Halvis et al. | 250/226 |
| 2008/0088840 A1 | 4/2008 | Bodkin et al. | 356/328 |
| 2008/0272312 A1 | 11/2008 | Tuschel | 250/459.1 |
| 2009/0268010 A1* | 10/2009 | Zhao | H04N 13/207 348/45 |
| 2009/0275831 A1 | 11/2009 | Hall et al. | 600/437 |
| 2010/0063355 A1 | 3/2010 | Matsuura | 600/109 |
| 2011/0133056 A1 | 6/2011 | Dattner et al. | 250/208.1 |
| 2011/0268333 A1* | 11/2011 | Klingenbeck | A61B 6/4441 382/131 |
| 2012/0133778 A1 | 5/2012 | Shih et al. | 348/169 |
| 2014/0031669 A1* | 1/2014 | Hensley | A61B 5/055 600/411 |
| 2014/0226150 A1 | 8/2014 | Colonna De Lega | 356/73 |
| 2014/0378843 A1 | 12/2014 | Valdes et al. | 600/476 |

OTHER PUBLICATIONS

Written Opinion dated Jun. 24, 2016 in related application No. PCT/US2016/016991.

European Search Report dated Jun. 8, 2018 in related application No. EP 16747416.

\* cited by examiner

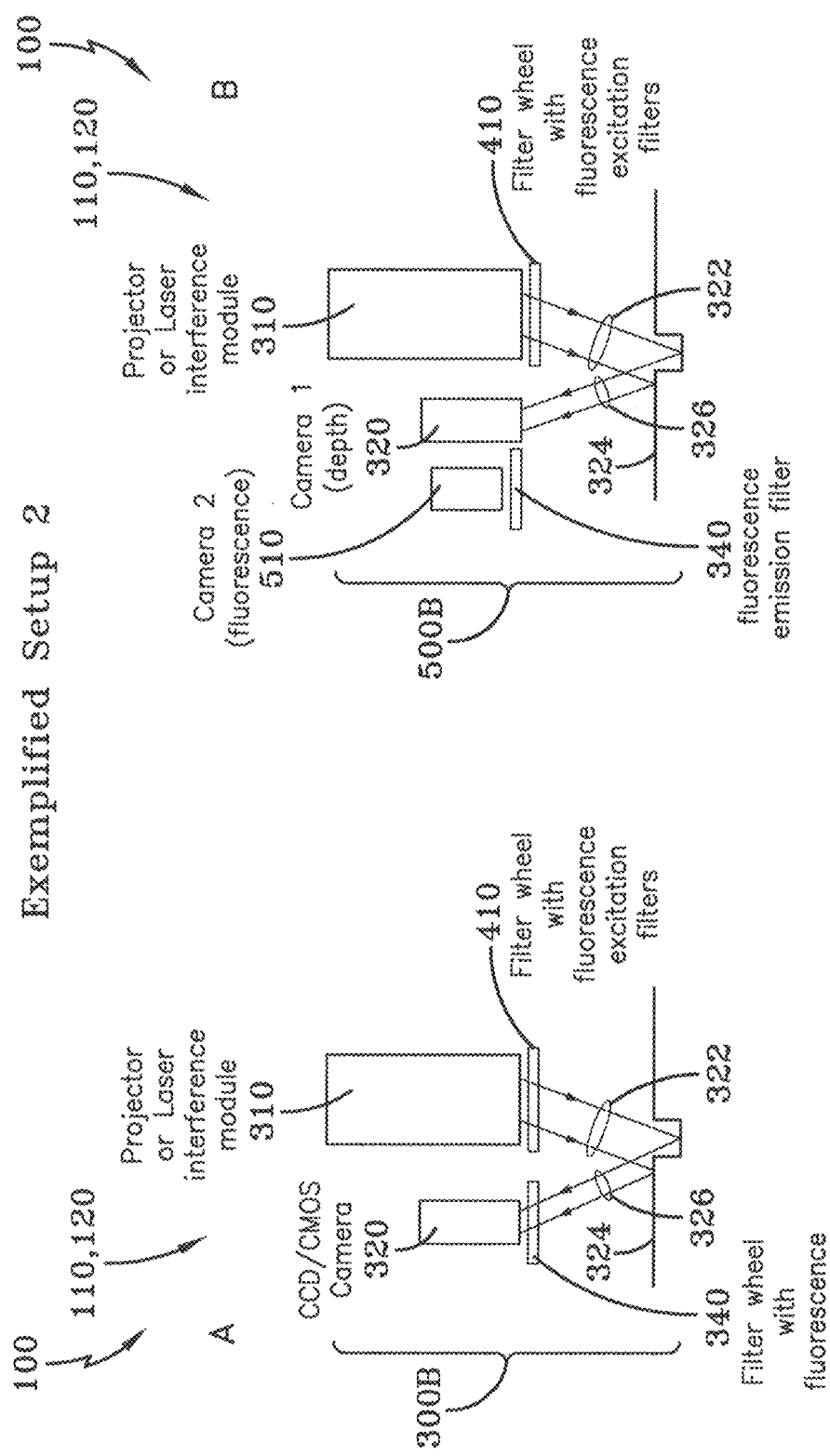

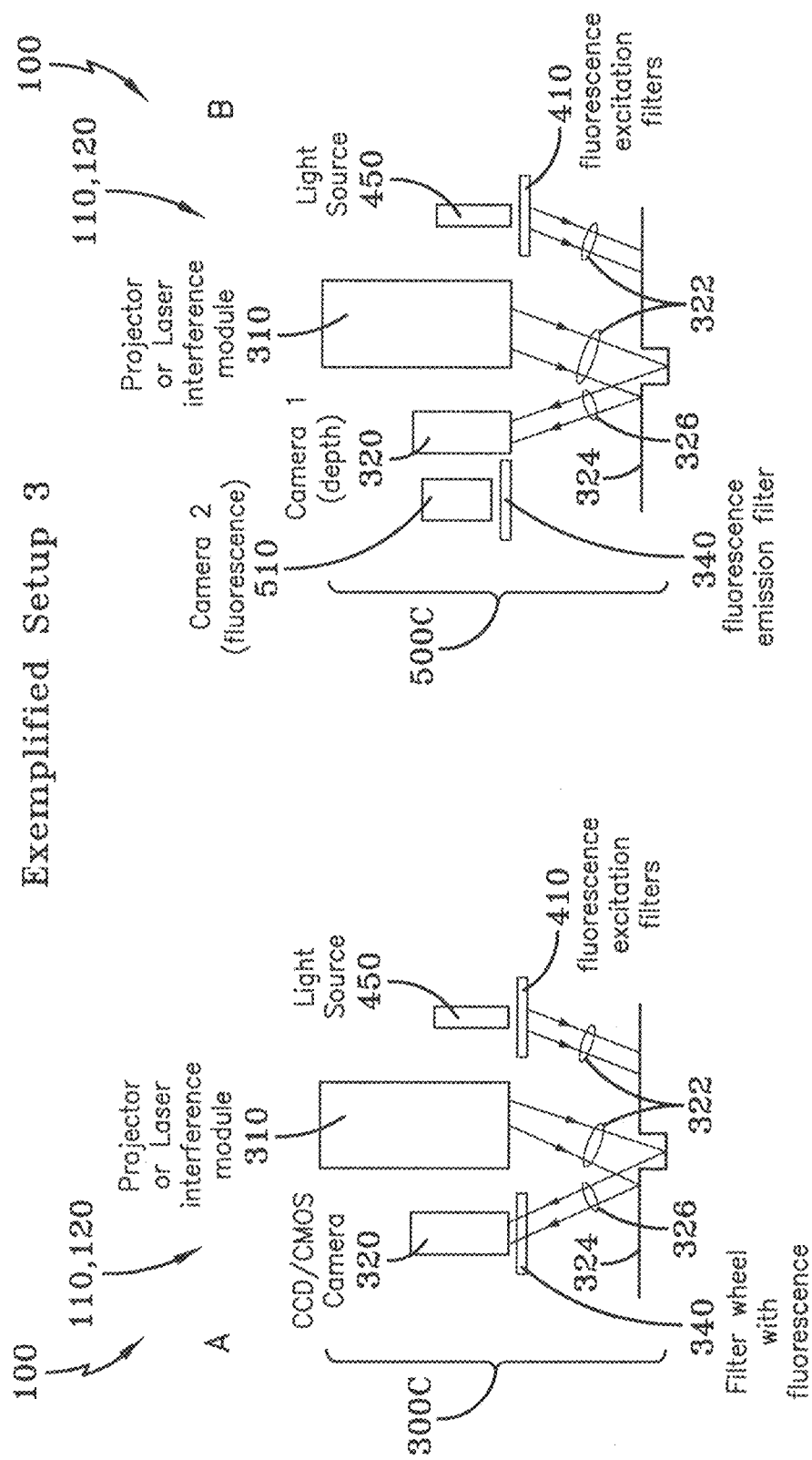

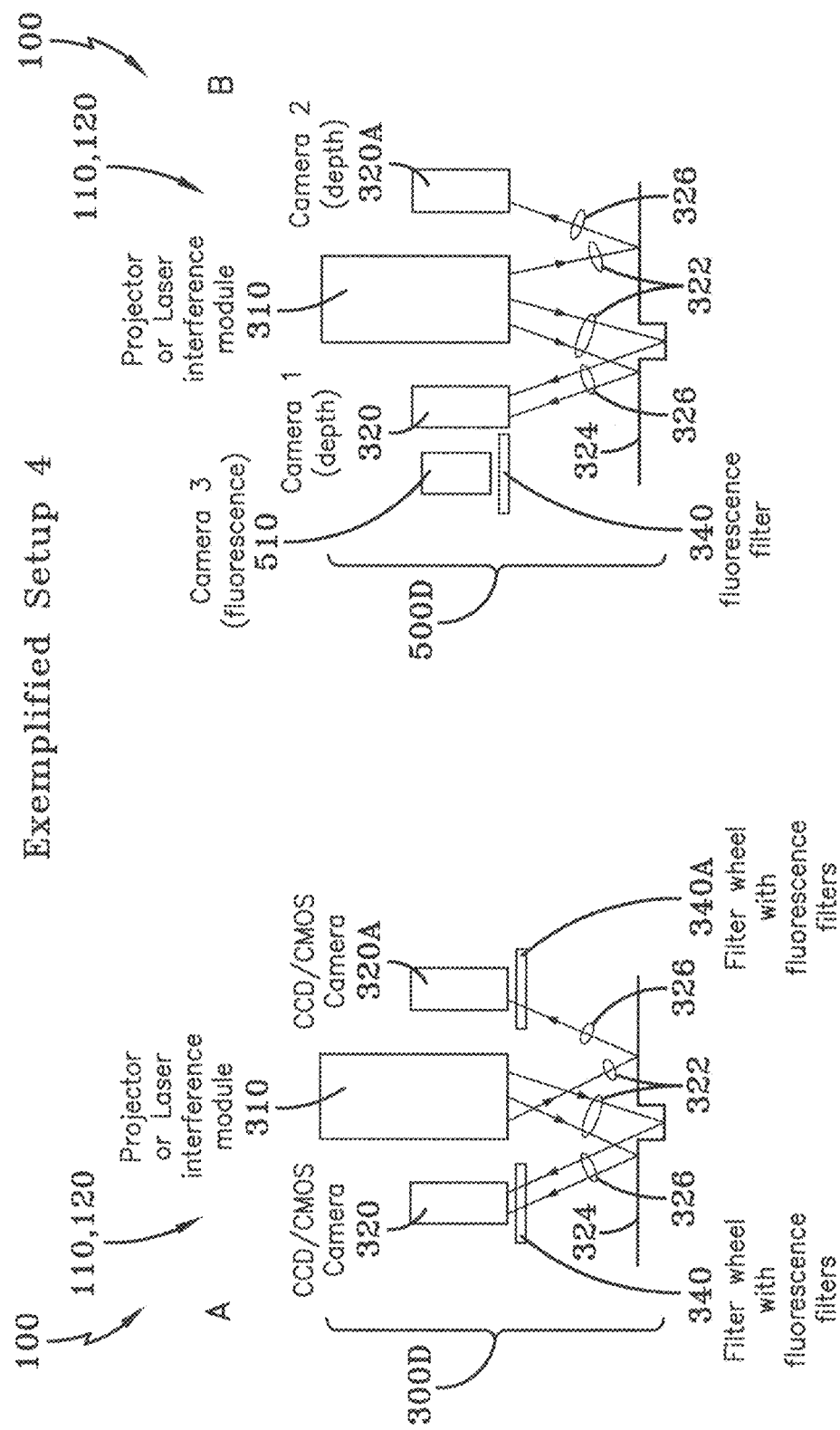

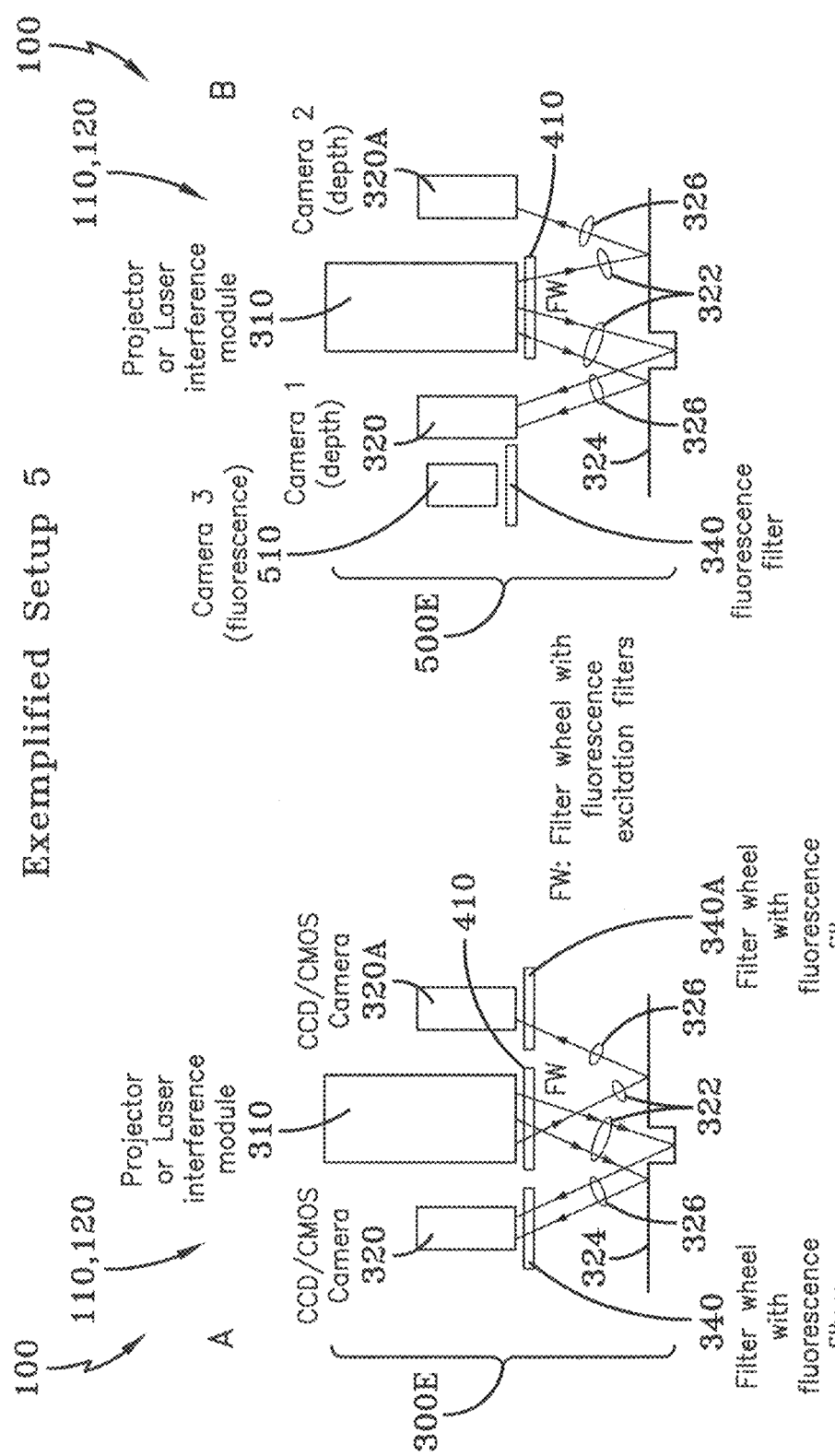

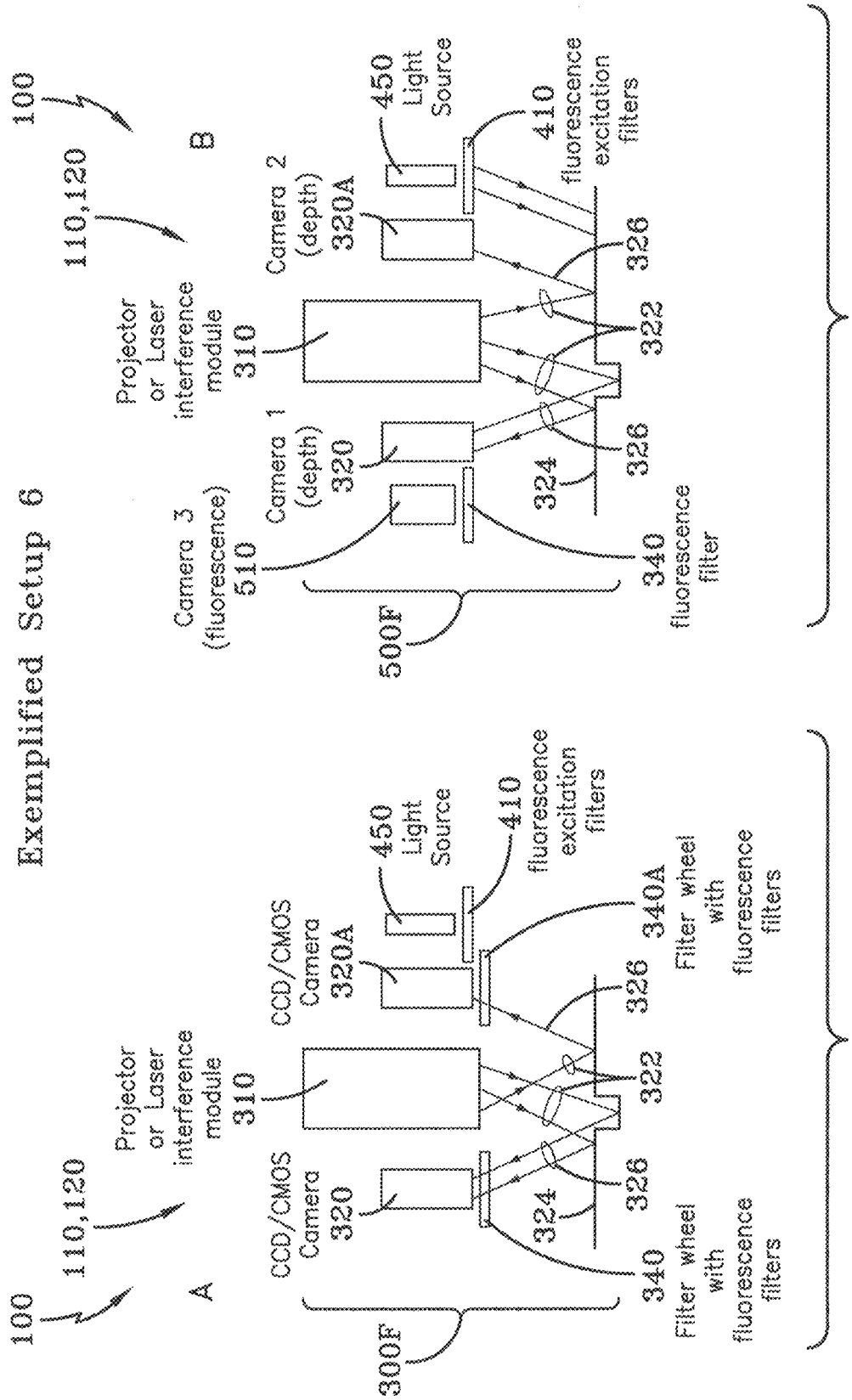

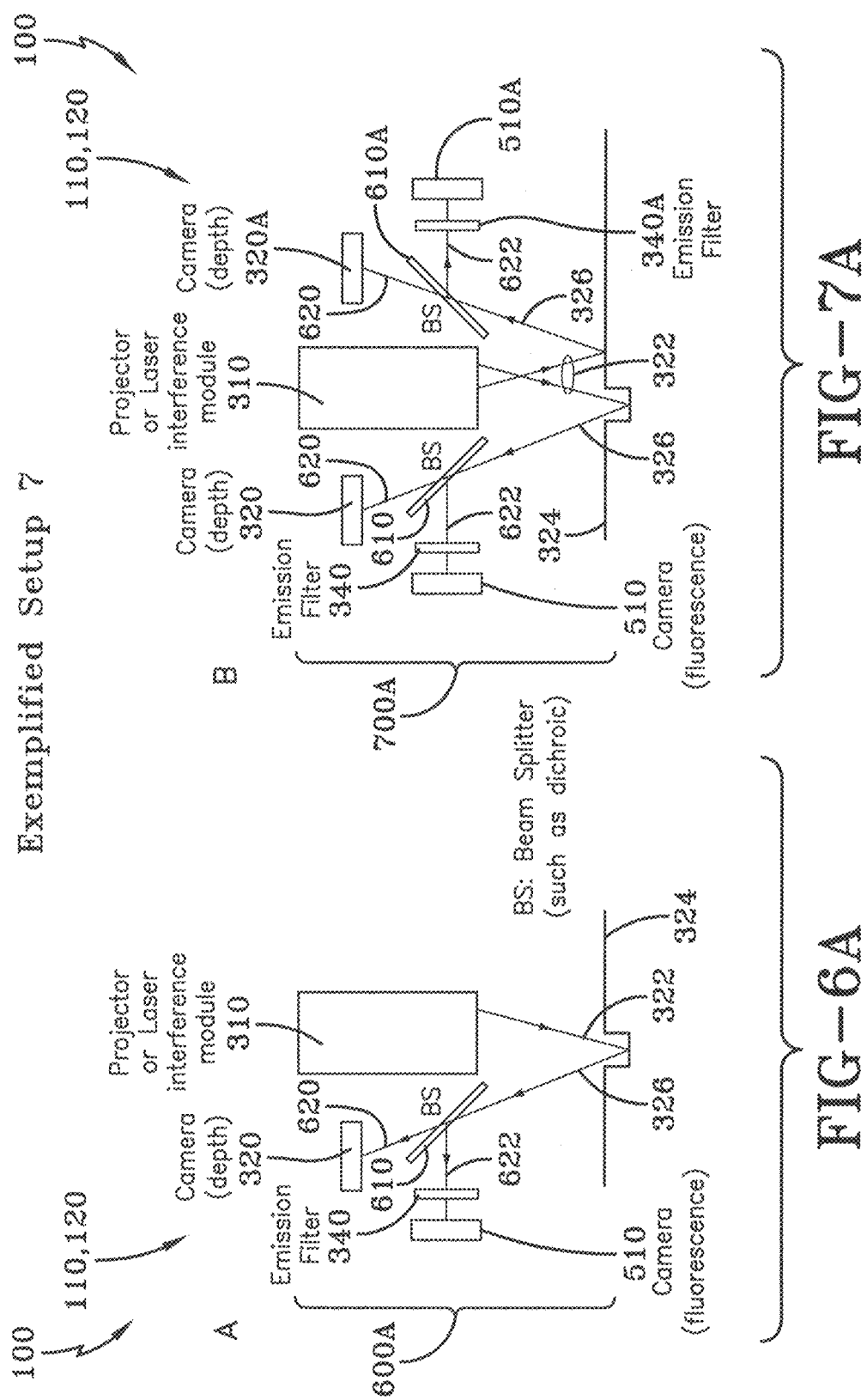

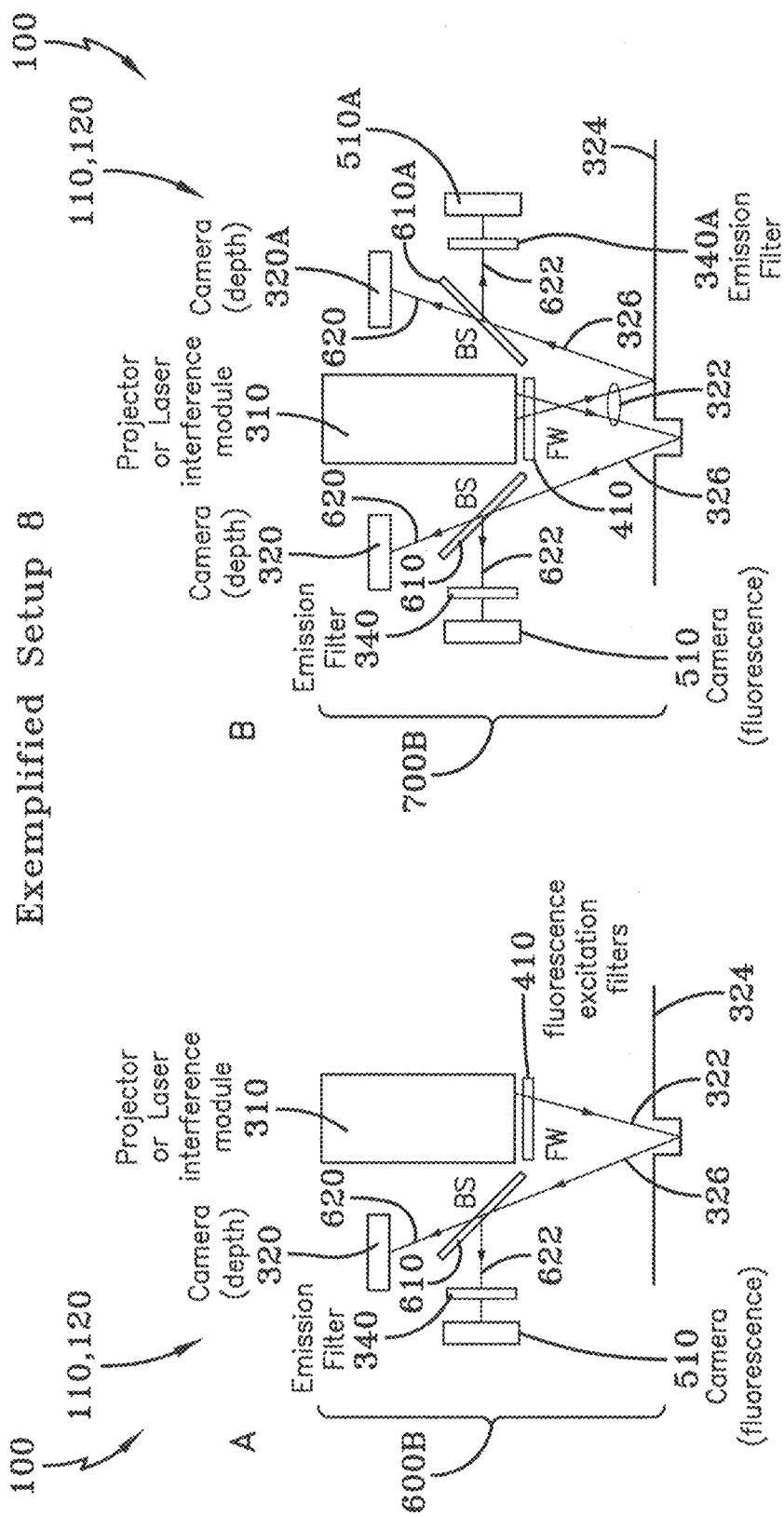

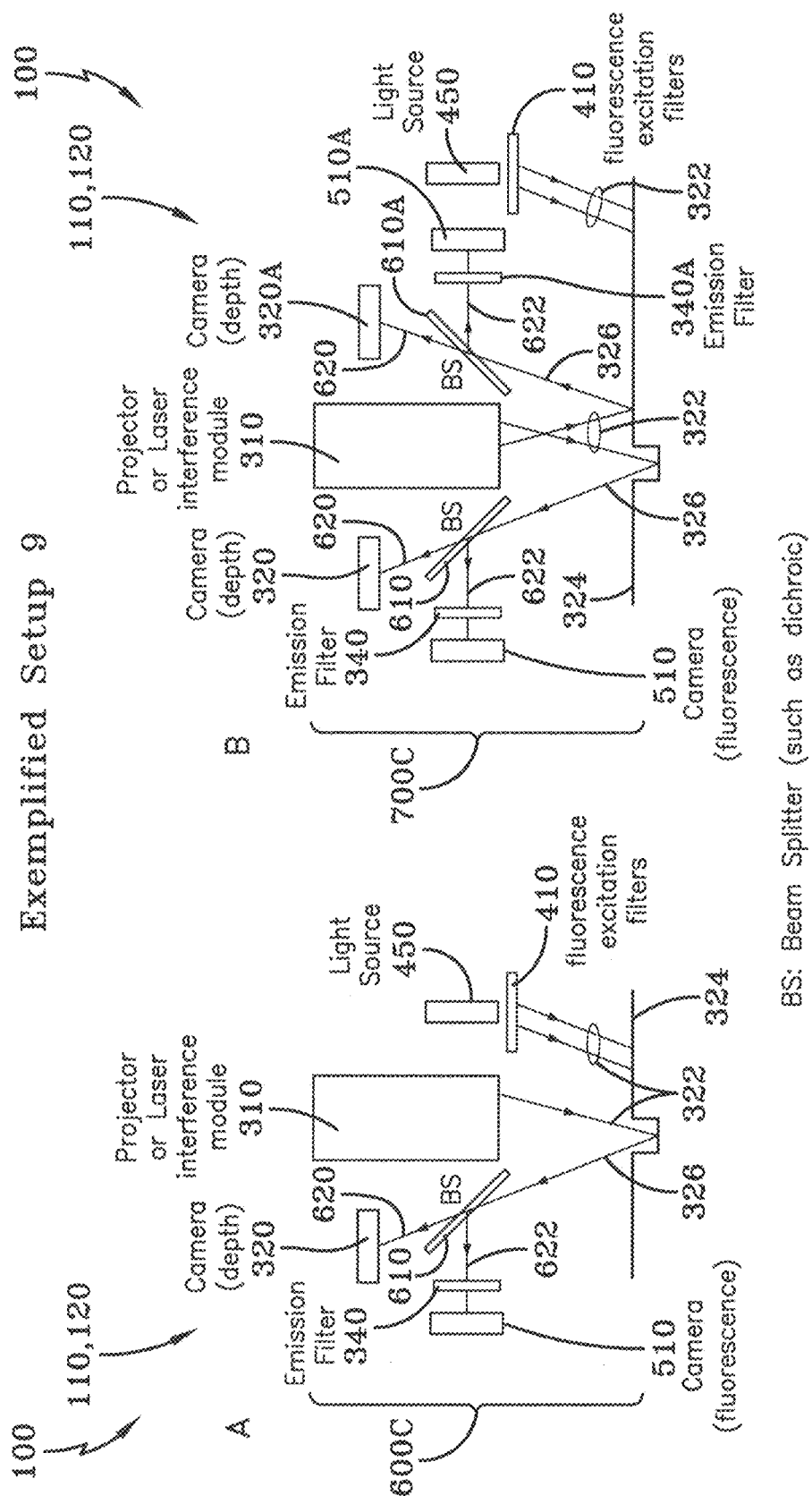

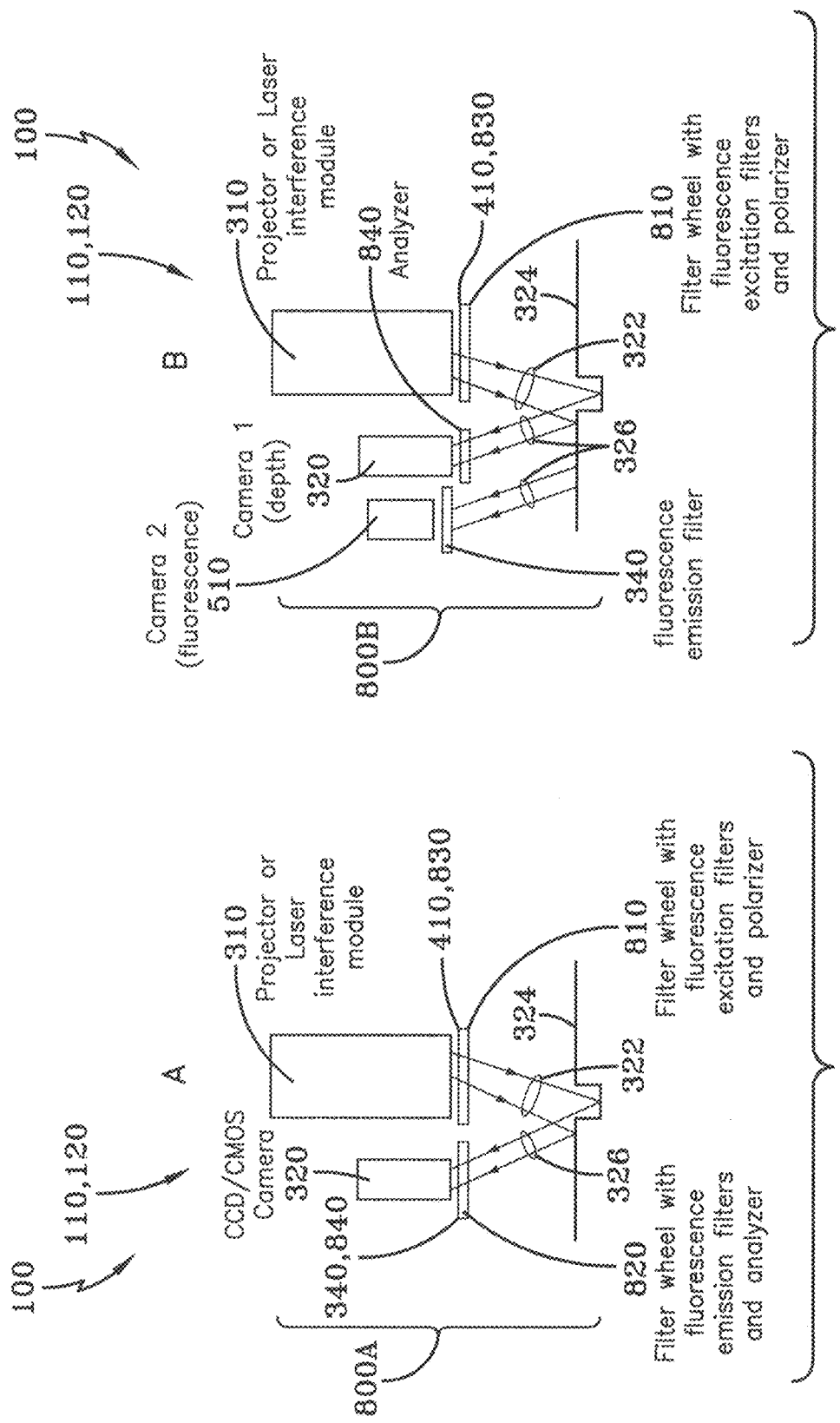

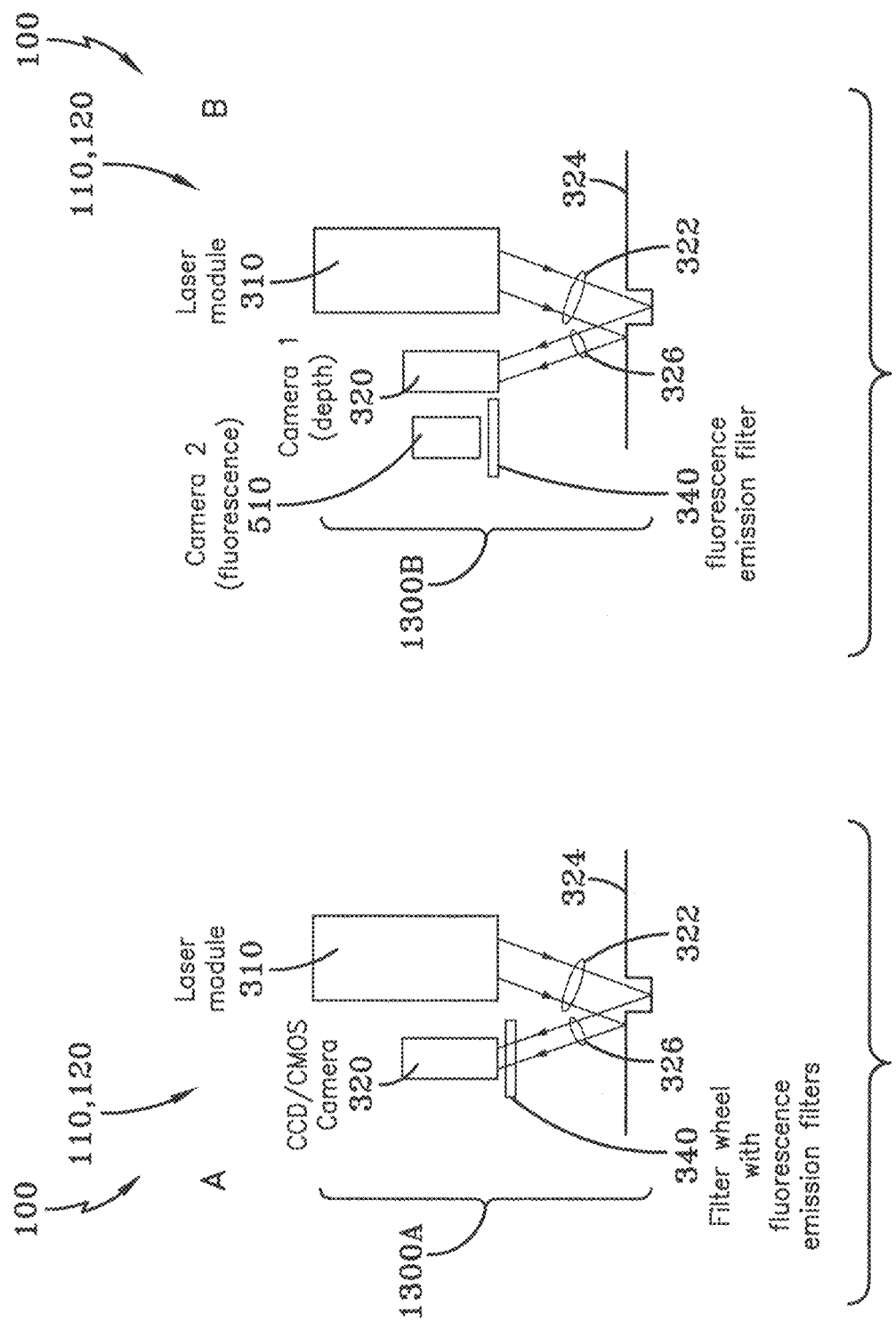

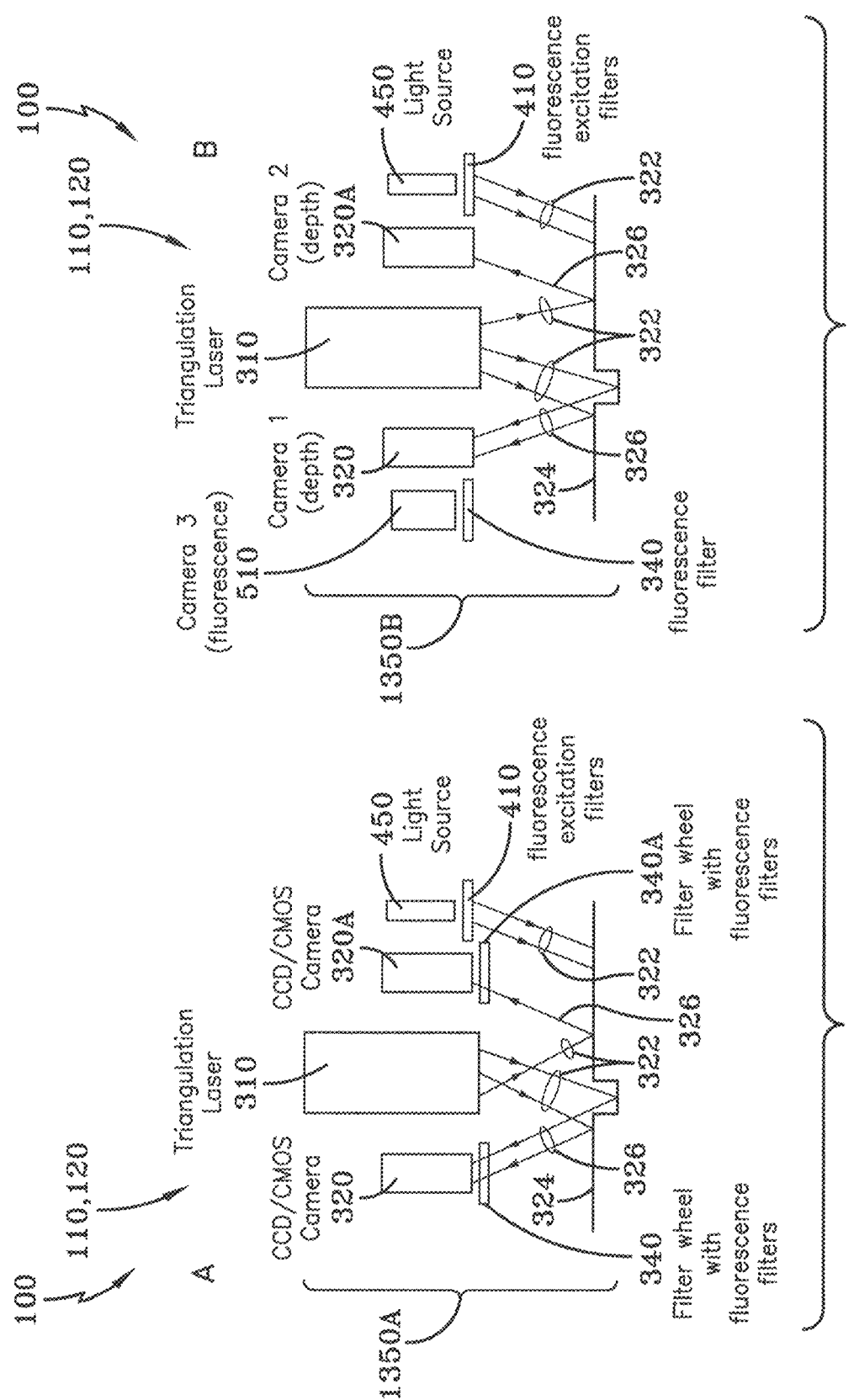

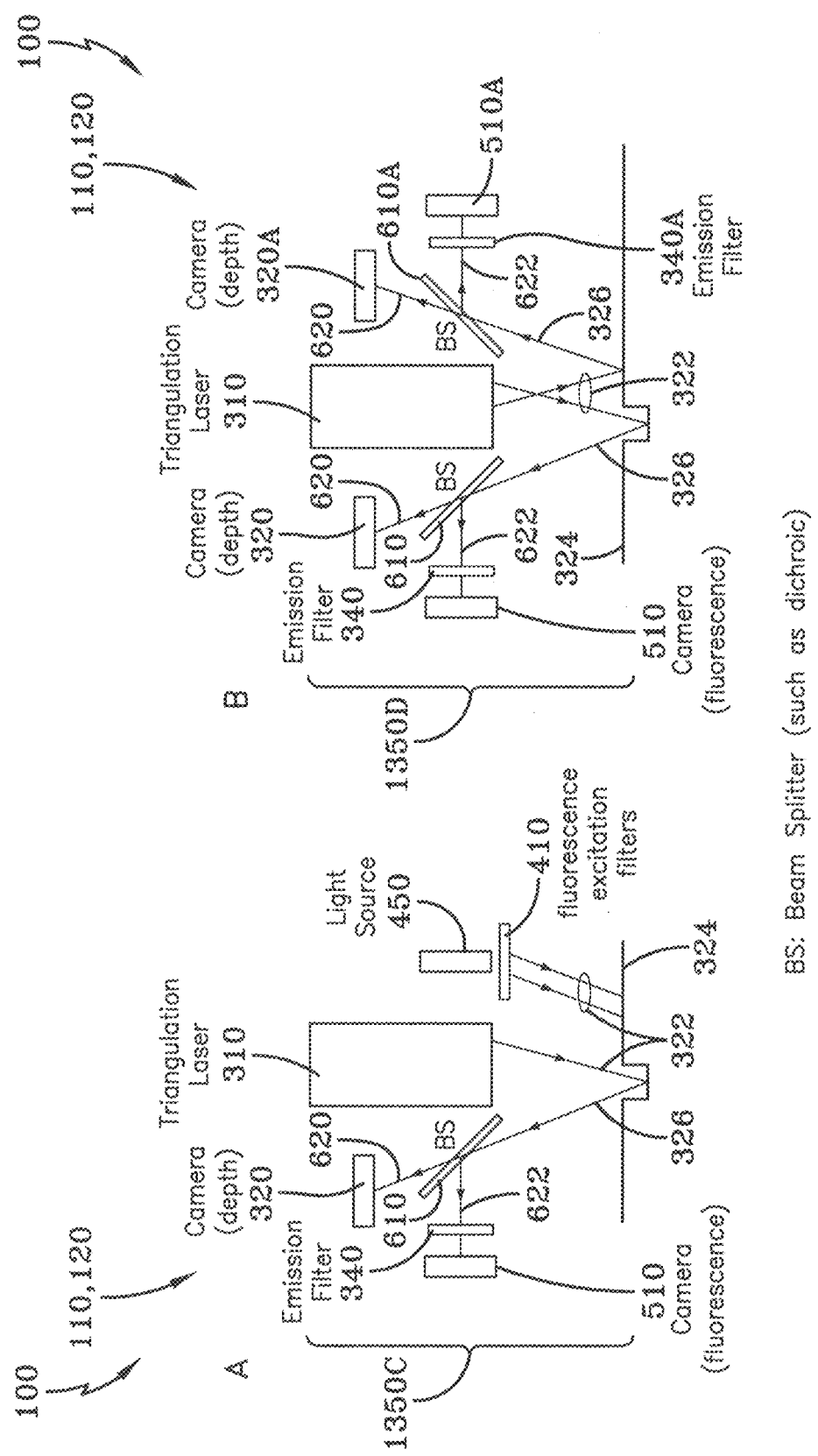

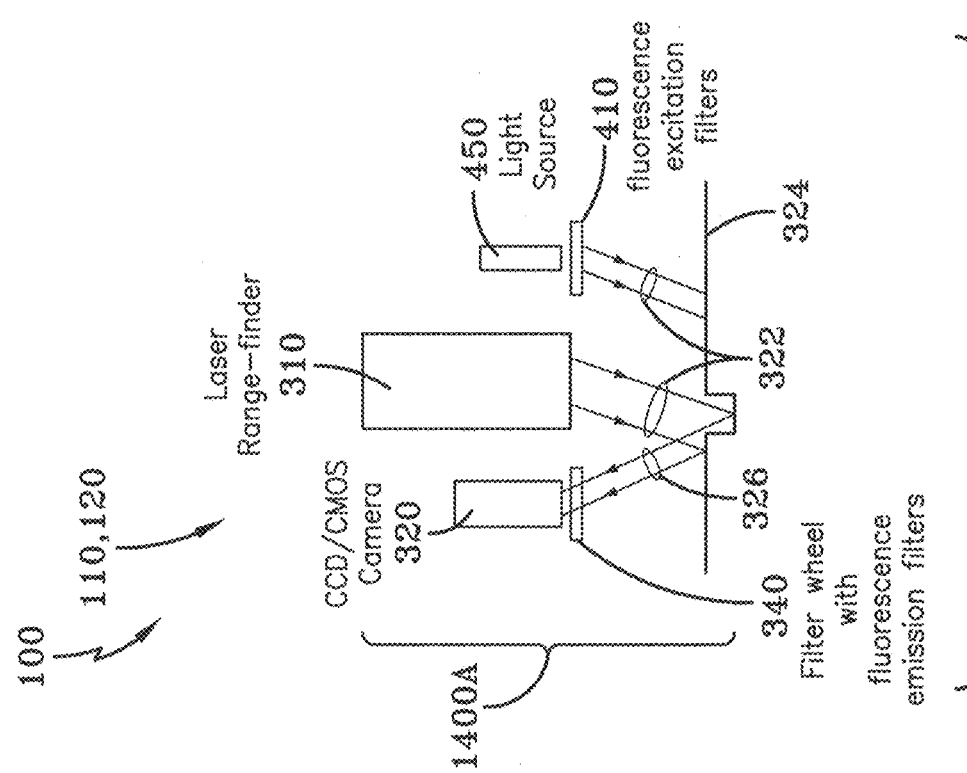

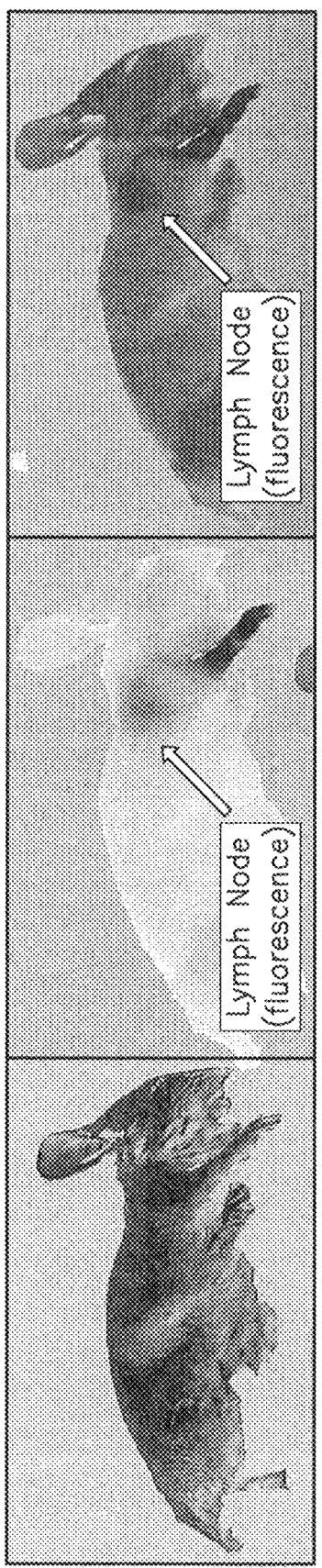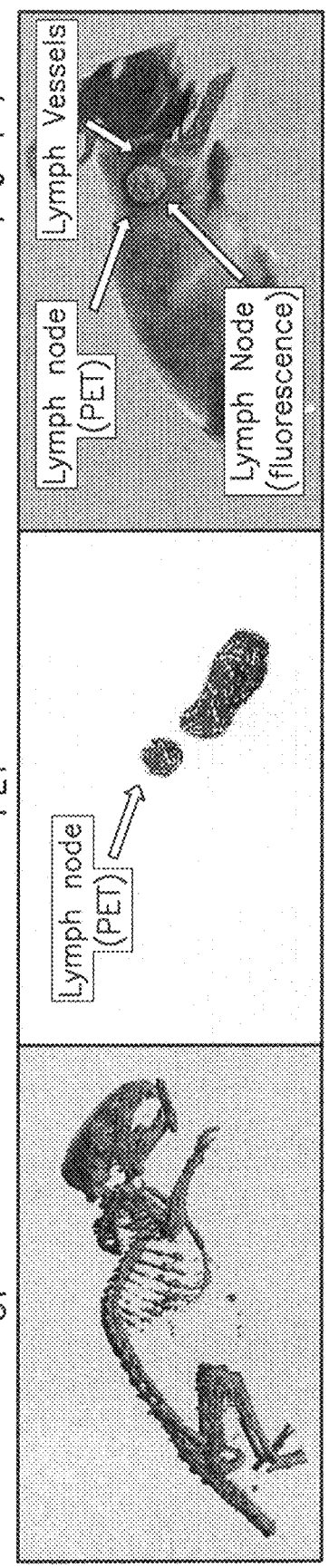

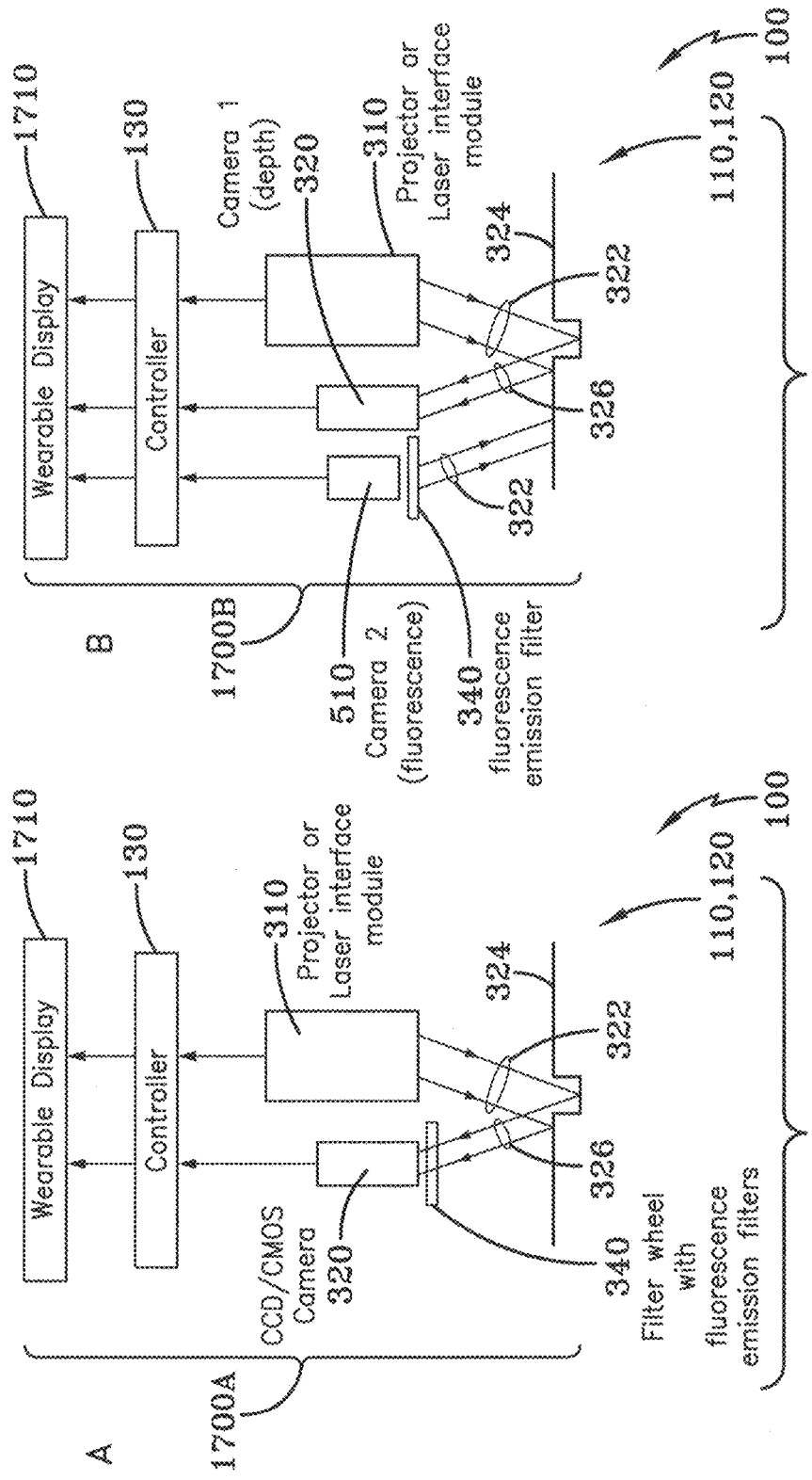

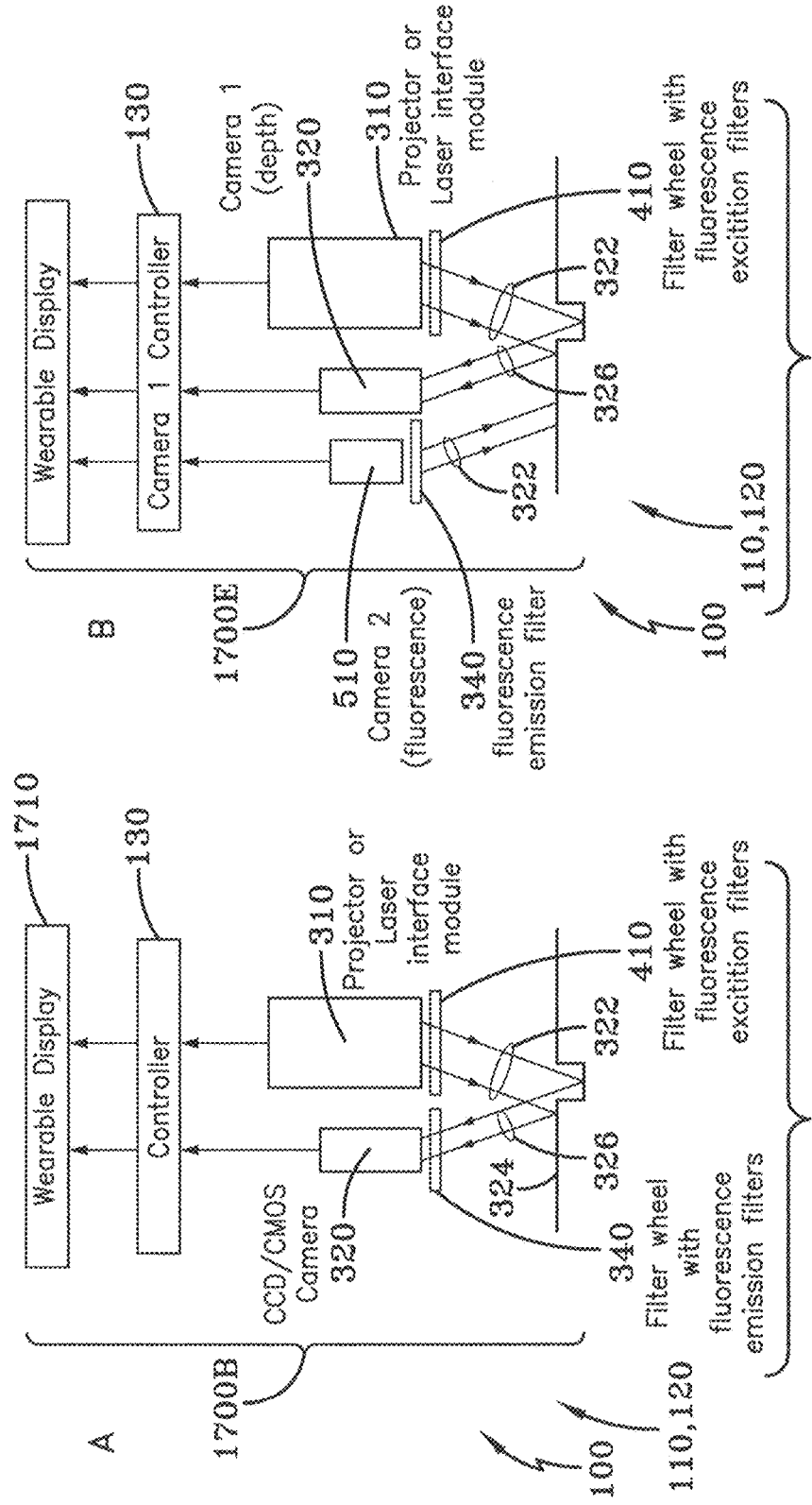

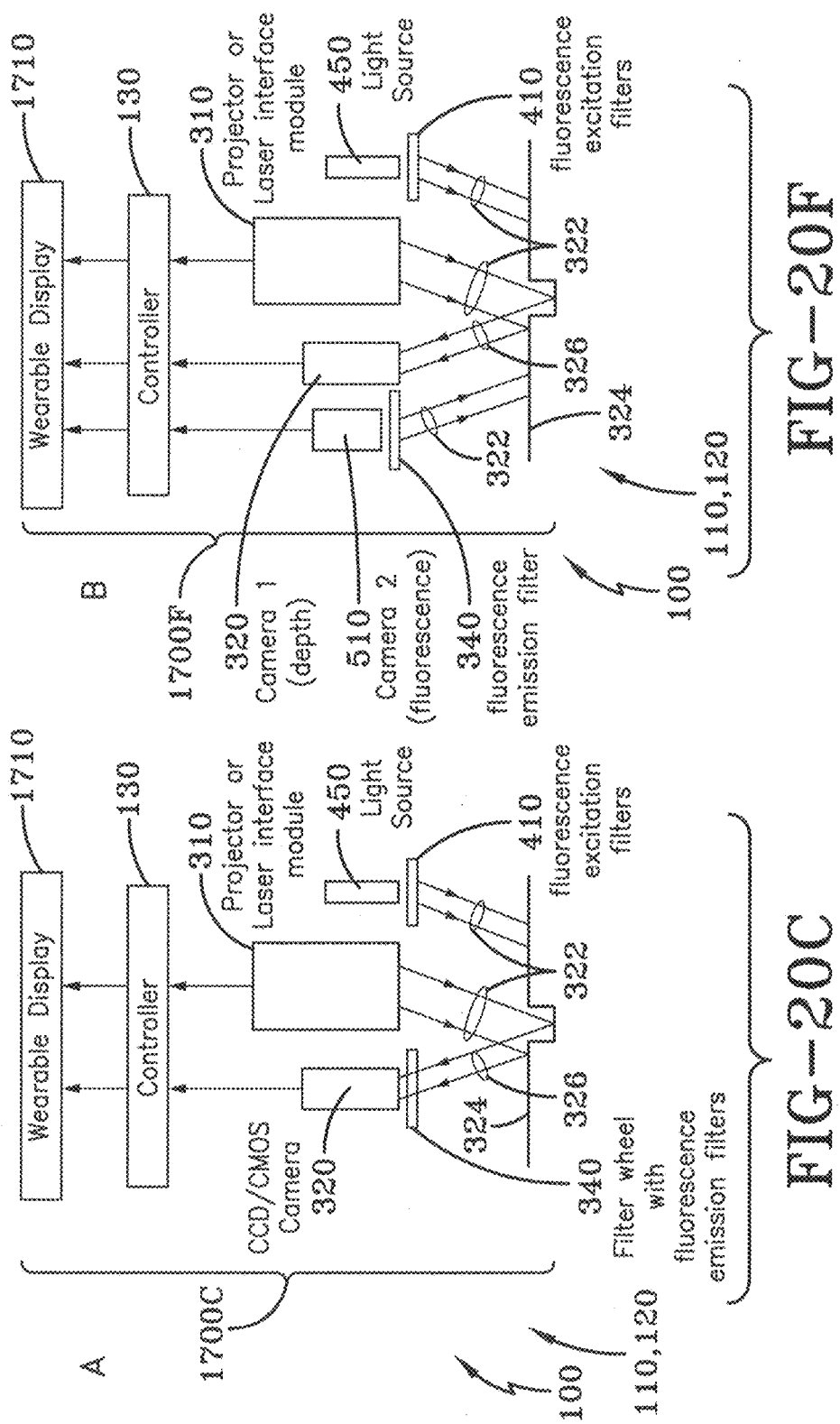

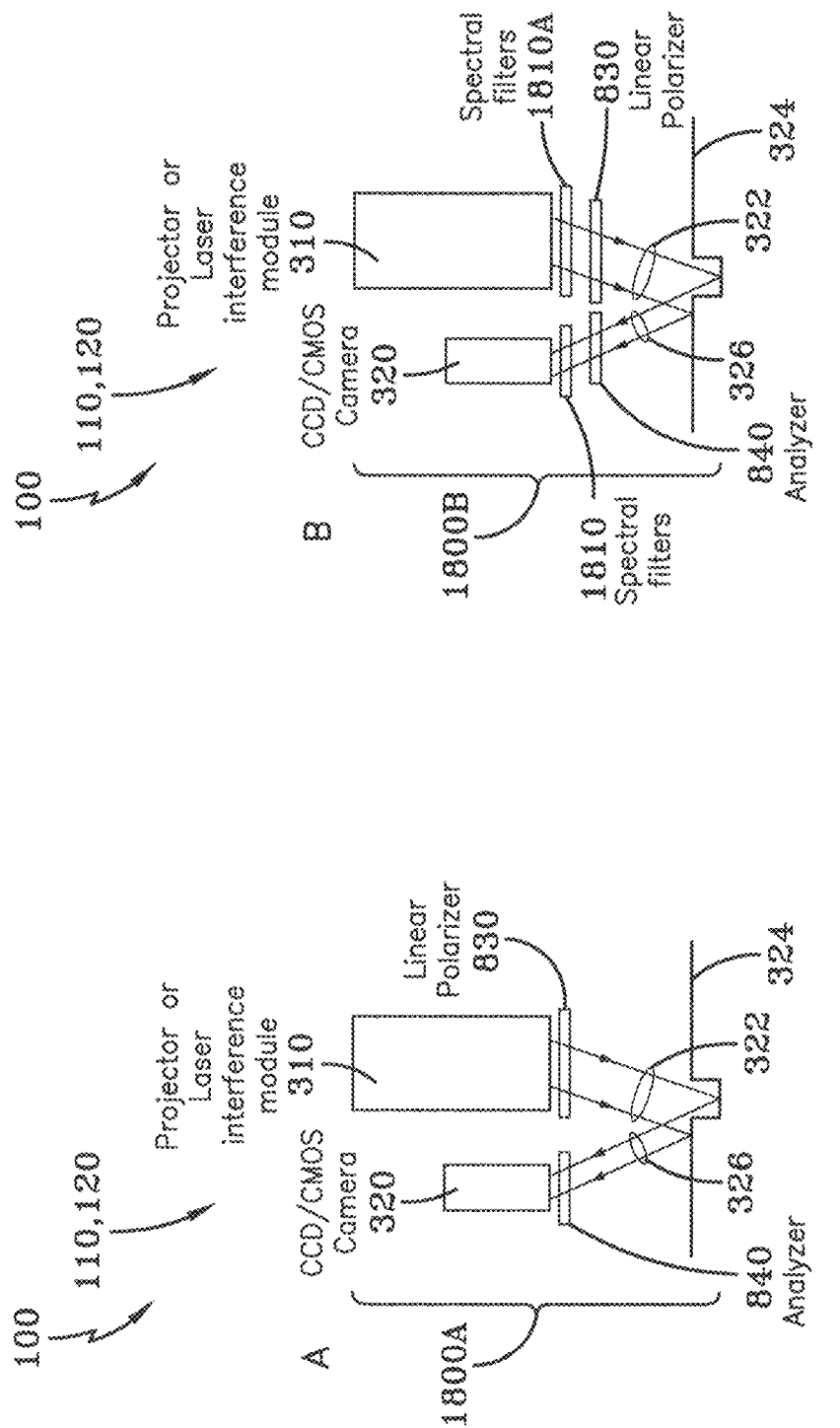

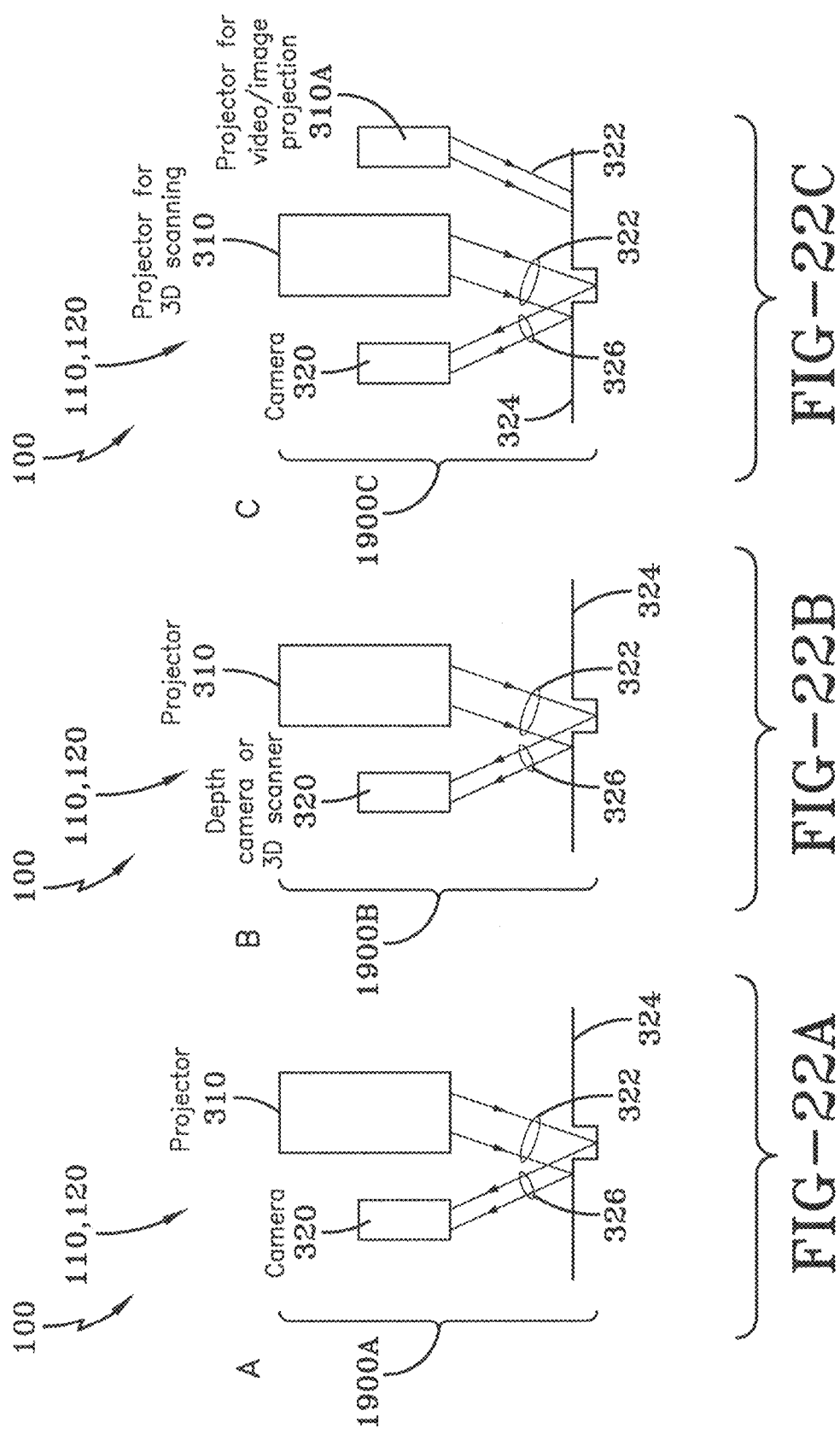

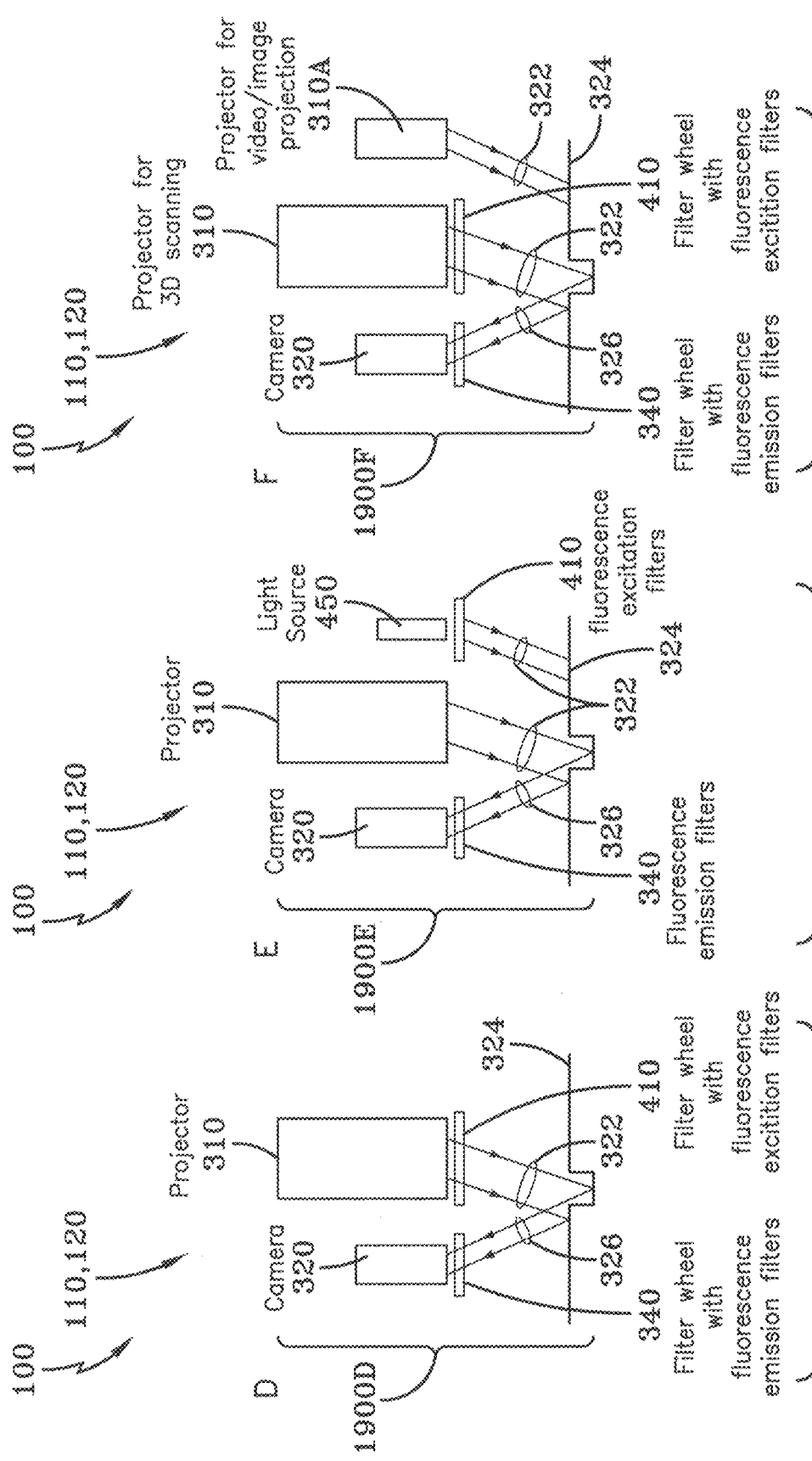

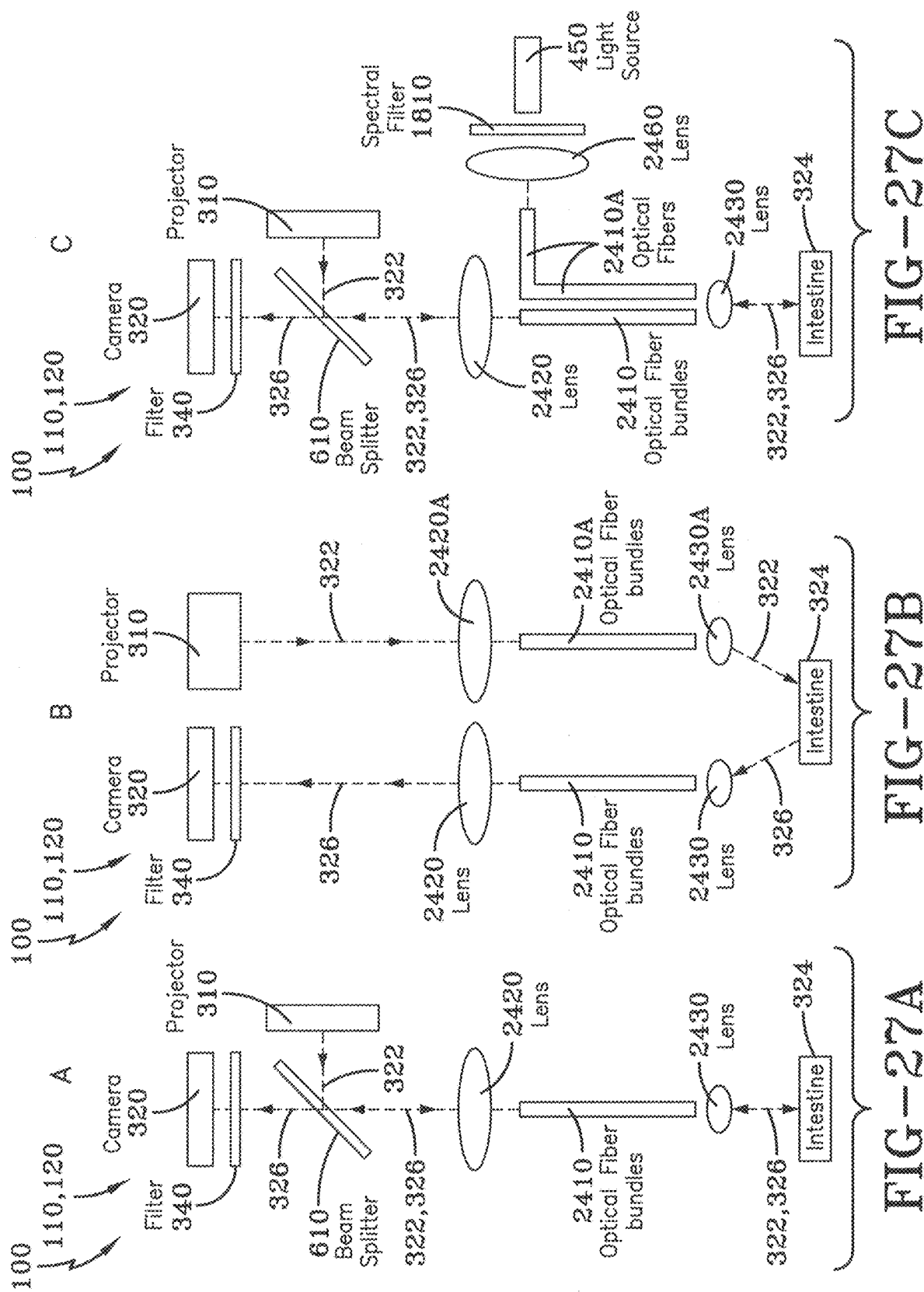

OPTICAL IMAGING SYSTEM AND METHODS THEREOF

CROSS REFERENCE TO RELATED APPLICATION

This application is a continuation application of prior application Ser. No. 16/858,887 filed Apr. 27, 2020, which is a continuation application of prior application Ser. No. 15/547,590 filed Jul. 31, 2017, which is a § 371 application of International application number PCT/US2016/016991 filed Feb. 8, 2016 which claims the benefit of U.S. Provisional application No. 62/112,993 filed Feb. 6, 2015, all of which are incorporated herein by reference.

TECHNICAL FIELD

Generally, the present invention relates to systems and methods of optical imaging. In particular, the present invention relates to a system and method for performing 3D scanning, optical imaging, multi-modal imaging, and image registration and display. More particularly, the present invention relates to a system and method for utilizing 3D scanning in combination with biomedical imaging, such as optical imaging and nuclear imaging modalities, to perform diagnostic functions.

BACKGROUND OF THE INVENTION

Current imaging techniques, such as those used in the medical field, still fail to deliver robust integration of multiple images, as desired by healthcare professionals, such as surgeons. For example, surface topography measurements are currently conducted using 3D scanning methods, such as that utilized by a structured light three-dimensional (3D) scanner, which do not offer advanced optical imaging capabilities, such as that provided by fluorescence imaging or polarization imaging. While 3D scanning based imaging methods provide surface information, topography data, 3D point cloud data, and the ability to track objects and their movements, 3D scanning only provides limited biomedical applications and diagnostic information.

Alternatively, biomedical optical imaging methods typically involve the use of planar imaging methods, and do not provide surface topography information. For example, the planar imaging information acquired by such biomedical optical imaging methods does not present morphology/topography information. In addition, such planar imaging information is difficult to fuse or combine with other imaging information, such as computerized tomography (CT) or magnetic resonance imaging (MRI) data. The lack of 3D shape information from current optical imaging systems, such as a fluorescence imaging system, makes the registration between optical imaging and other imaging modalities difficult.

For example, typical planar fluorescence imaging is not able to acquire adequate depth/topography information from a target of interest, such as a surgical site. Fluorescence tomography is very slow and is unable to be used for intraoperative imaging, and to track tissue deformation. Furthermore, it is difficult to co-register fluorescence imaging with preoperative imaging data from a CT, an MRI, or positron emission tomography (PET).

Therefore, there is a need for an imaging system that utilizes 3D scanning with biomedical optical imaging techniques to generate surface topography images that are integrated with information that is obtained from specialized optical imaging methods, such as fluorescence imaging or polarization imaging. In addition, there is a need for an imaging system that utilizes 3D scanning to provide surface topography information, tracking of movements and deformation of the target object, and the generation of 3D models for data fusion/image registration, in combination with an optical imaging method that provides diagnostic information. Additionally, there is a need for an imaging system that utilizes 3D scanning, which is capable of use in various applications, including but not limited to surgery, therapeutic monitoring, radiotherapy monitoring, wound healing, telemedicine, security check, and medical training. Furthermore, there is a need for an imaging system that combines virtual reality features with 3D scanning imaging and biomedical optical imaging techniques.

SUMMARY OF THE INVENTION

In light of the foregoing, it is one aspect of the present invention to provide an optical imaging system to image a target object comprising: a controller; a light emitter module coupled to the controller to illuminate the target object with light; and an image detection module coupled to the controller, the image detection module having a field of view to image the target object; wherein the controller controls the light emitter and the image detection module, such that in one mode the image detection module captures a three-dimensional (3D) topography image of the target object, and in a second mode the image detection module captures a specific image of the target object.

It is another aspect of the present invention to provide an optical imaging system to image a non-flat target object comprising: a controller; a light emitter module coupled to the controller to illuminate the target object with light; an image detection module coupled to the controller, the image detection module having a field of view to image the non-flat target object; wherein the controller controls the light emitter and the image detection module, such that the image detection module captures a three-dimensional (3D) topography image of the target object, and wherein the controller identifies the relative distance between a plurality of portions of the non-flat surface and the light emitter module to generate a corrected projection image, whereupon the corrected projection image is projected by the light emitter module.

It is another aspect of the present invention to provide a method of registering images of a target object comprising the steps of: acquiring a first specific image of the target object from a first image detection module; acquiring a second specific image of the target object from a second image detection module; acquiring a distance of the target object relative to two or more image detection modules to obtain a topography image of the target object; calculating a transformation matrix based on the first specific image, the second specific image, and the distance; and registering the first specific image to the second specific image based on the transformation matrix.

It is another aspect of the present invention to provide a method of optical scanning of a target object comprising the steps of: illuminating the target object by a polarized light; processing the light returned from the target object by an analyzer as analyzed light; and detecting the analyzed light as a topography image of the target object.

It is another aspect of the present invention to provide an optical imaging system, wherein a controller is configured to perform the steps comprising:

computing transformation matrices between a pre-operative image space, an intra-operative image space and a peripheral image space; and co-registering the pre-operative image spaces, the intra-operative image space, and the peripheral image space.

It is another aspect of the optical imaging system of the present invention oxygen saturation imaging or vasculature imaging of a target object.

It is another aspect of the optical imaging system of the present invention to provide to capture 3D shape, fluorescence imaging, absorption coefficient and scattering coefficient of a target object It is another aspect of the optical imaging system of the present invention to provide gesture recognition.

It is another aspect of the optical imaging system of the present invention to provide cardiac gating.

It is another aspect of the optical imaging system of the present invention to be utilized with a contrast agent that is dual-labeled (e.g. a contrast agent that is both fluorescent and also labeled with radioisotope for PET or SPECT imaging).

It is another aspect of the optical imaging system of the present invention to be configured, whereby fluorescence imaging (such as 5-Aminolevulinic acid or Indocyanine green) is used in conjunction with preoperative surgical navigation (e.g. MRI, CT, PET, SPECT . . . ) for guiding interventions or surgeries.

It is another aspect of the optical imaging system of the present invention to provide, where fluorescence imaging (such as 5-Aminolevulinic acid or Indocyanine green) is being used in conjunction with preoperative surgical navigation (eg. MRI, CT, PET, SPECT . . . ) for guiding interventions or surgeries for the brain.

It is another aspect of the optical imaging system of the present invention to provide deformation compensation using biomechanical modeling and FEM modeling.

It is another aspect of the optical imaging system of the present invention to provide vasculature imaging, where vein imaging is preferred with a light source and a detector positioned on 2 different or opposite sides of tissues to be imaged (transmission geometry).

It is another aspect of the optical imaging system of the present invention to provide vasculature imaging, where vein imaging is performed with a light source and a detector on the same side of tissues to be imaged (reflectance geometry).

It is another aspect of the optical imaging system of the present invention to provide vasculature imaging, where the vein imaging is done with multispectral imaging.

It is another aspect of the optical imaging system of the present invention to provide projection quality monitoring, projection optimization and least-squares errors are implemented, and the accuracy of projection is updated accordingly.

It is another aspect of the optical imaging system of the present invention to provide a method of optical scanning of a target object comprising the steps of illuminating the target object by a polarized light; processing the light returned from the target object by an analyzer as analyzed light; and detecting the analyzed light as a topography image of the target object, wherein the polarized light includes a plurality of wavelengths, whereby each wavelength corresponds to a depth within the target object; and processing the polarized light by a spectral filter having a band-pass for each one of the plurality of wavelengths; processing the analyzed light by a spectral filter having a band-pass for each one of the plurality of wavelengths; detecting the analyzed light of each one of the plurality of wavelengths as a topography image for each depth within the target object.

It is another aspect of the optical imaging system of the present invention to generate images by subtraction reflectance image based on one of the plurality of wavelengths with another reflectance image based on another one of the plurality of wavelengths following normalization.

BRIEF DESCRIPTION OF THE DRAWINGS

These and other features and advantages of the present invention will become better understood with regard to the following description, appended claims, and accompanying drawings wherein:

FIG. 4B is a block diagram of another configuration of the optical imaging system in accordance with the concepts of the present invention;

FIG. 4C is a block diagram of an alternative configuration of the optical imaging system in accordance with the concepts of the present invention;

FIG. 4D is a block diagram of an additional configuration of the optical imaging system in accordance with the concepts of the present invention;

FIG. 4E is a block diagram of a further configuration of the optical imaging system in accordance with the concepts of the present invention;

FIG. 4F is block diagram of yet another configuration of the optical imaging system in accordance with the concepts of the present invention;

FIG. 5B is a block diagram of another configuration of the optical imaging system in accordance with the concepts of the present invention;

FIG. 5C is a block diagram of an alternative configuration of the optical imaging system in accordance with the concepts of the present invention;

FIG. 5D is a block diagram of an additional configuration of the optical imaging system in accordance with the concepts of the present invention;

FIG. 5E is a block diagram of a further configuration of the optical imaging system in accordance with the concepts of the present invention;

FIG. 5F is a another block diagram of yet another configuration of the optical imaging system in accordance with the concepts of the present invention;

FIG. 6A is a block diagram of one configuration of the optical imaging system in accordance with the concepts of the present invention;

FIG. 6B is a block diagram of another configuration of the optical imaging system in accordance with the concepts of the present invention;

FIG. 6C is a block diagram of an alternative configuration of the optical imaging system in accordance with the concepts of the present invention;

FIG. 7A is a block diagram of one configuration of the optical imaging system in accordance with the concepts of the present invention;

FIG. 7B is a block diagram of another configuration of the optical imaging system in accordance with the concepts of the present invention;

FIG. 7C is a block diagram of an alternative configuration of the optical imaging system in accordance with the concepts of the present invention;

FIG. 8A is a schematic diagram of one configuration of the optical imaging system in accordance with the concepts of the present invention;

FIG. 8B is a schematic diagram of another configuration of the optical imaging system in accordance with the concepts of the present invention;

FIG. 14A is a block diagram of one configuration of the optical imaging system in accordance with the concepts of the present invention;

FIG. 14B is a block diagram of another configuration of the optical imaging system in accordance with the concepts of the present invention;

FIG. 15A is a block diagram of one configuration of the optical imaging system in accordance with the concepts of the present invention;

FIG. 15B is a block diagram of another configuration of the optical imaging system in accordance with the concepts of the present invention;

FIG. 15C is a block diagram of an yet another configuration of the optical imaging system in accordance with the concepts of the present invention;

FIG. 15D is a block diagram of an additional configuration of the optical imaging system in accordance with the concepts of the present invention;

FIG. 16A is a block diagram of one configuration of the optical imaging system in accordance with the concepts of the present invention;

FIGS. 18A-I is an image of showing the co-registration of various images in accordance with the concepts of the present invention;

FIG. 20A is a block diagram of one configuration of the optical imaging system in accordance with the concepts of the present invention;

FIG. 20B is a block diagram of another configuration of the optical imaging system in accordance with the concepts of the present invention;

FIG. 20C is a block diagram of an alternative configuration of the optical imaging system in accordance with the concepts of the present invention;

FIG. 20D is a block diagram of an additional configuration of the optical imaging system in accordance with the concepts of the present invention;

FIG. 20E is a block diagram of a further configuration of the optical imaging system in accordance with the concepts of the present invention;

FIG. 20F is a block diagram of yet another configuration of the optical imaging system in accordance with the concepts of the present invention;

FIG. 21A is a block diagram of one configuration of the optical imaging system in accordance with the concepts of the present invention;

FIG. 21B is a block diagram of another configuration of the optical imaging system in accordance with the concepts of the present invention;

FIG. 22A is a block diagram of one configuration of the optical imaging system in accordance with the concepts of the present invention;

FIG. 22B is a block diagram of another configuration of the optical imaging system in accordance with the concepts of the present invention;

FIG. 22C is a block diagram of an alternative configuration of the optical imaging system in accordance with the concepts of the present invention;

FIG. 22D is a block diagram of an additional configuration of the optical imaging system in accordance with the concepts of the present invention;

FIG. 22E is a block diagram of a further configuration of the optical imaging system in accordance with the concepts of the present invention;

FIG. 22F is a block diagram of yet another configuration of the optical imaging system in accordance with the concepts of the present invention;

FIG. 27A is a block diagram of one configuration of the optical imaging system in accordance with the concepts of the present invention;

FIG. 27B is a block diagram of another configuration of the optical imaging system in accordance with the concepts of the present invention; and FIG. 27C is a block diagram of an alternative configuration of the optical imaging system in accordance with the concepts of the present invention.

DETAILED DESCRIPTION OF THE INVENTION

Figure 1:
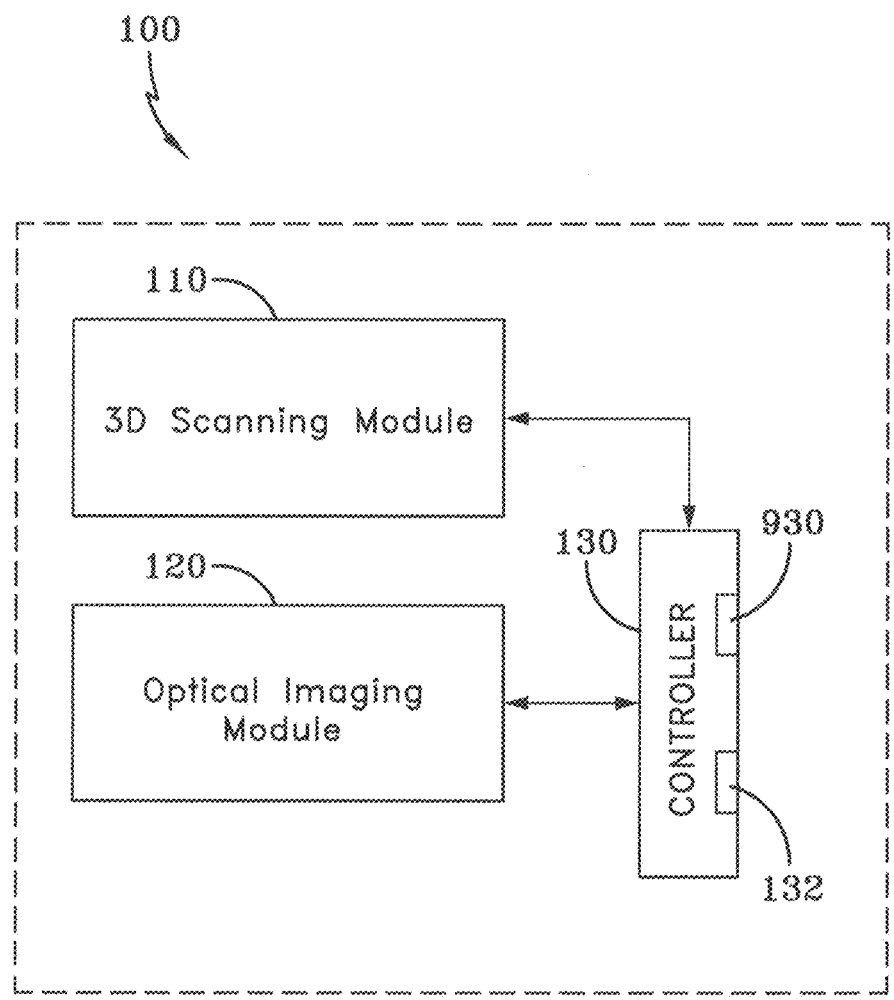
FIG. 1 is a block diagram of an optical imaging system in accordance with the concepts of the present invention.

An optical imaging system of the present invention is generally referred to by numeral 100, as shown in FIG. 1 of the drawings. In particular, the imaging system 100 includes a 3D scanning module 110 and an optical imaging module 120, which are in operative communication with one another via any suitable controller 130.

The 3D scanning module 110 includes one more technologies, including but not limited to laser scanning triangulation, structured light, time-of-flight, conoscopic holography, modulated light, stereo-camera, Fourier 3D scanning, low coherence interferometry, common-path interference 3D scanning, and contact profilometers.

The optical imaging module 120 includes one or more technologies, including but not limited to fluorescence imaging, reflectance imaging, hyperspectral imaging, IR thermal imaging, Cerenkov imaging, polarization imaging, polarization difference/ratio imaging, spectral polarization difference imaging, multiphoton imaging, second harmonic generation imaging, photoacoustic imaging, and fluorescence lifetime imaging.

As such, the system 100 is capable of acquiring both surface topography measurements and optical imaging information, such as fluorescence imaging information.

It should also be appreciated that the controller 130 may include the necessary hardware, software or combination thereof to carryout the functions of the present invention to be discussed. Furthermore, the controller 130 may comprise any suitable portable or standalone computing device that is capable of controlling the operation of the 3D scanning module 110 and the optical imaging module 120. It should also be appreciated that the controller 130 may include a data interface 132 that is capable of outputting data, such as imaging data, to a suitable projector or display coupled to the data interface 132. Several embodiments of such a configuration are provided in detail below. It should also be appreciated that the data interface 132 of the controller 130 may be configured to communicate through a wired or wireless network to the display or projector, as well as to other remote computing devices for transferring image data output by the data interface 132 thereto. In addition, the controller 130 may also be capable of receiving suitable commands through the data interface 130 from input devices, such as a keyboard, or by a computing device in communication with the data interface 130.

Figure 2:
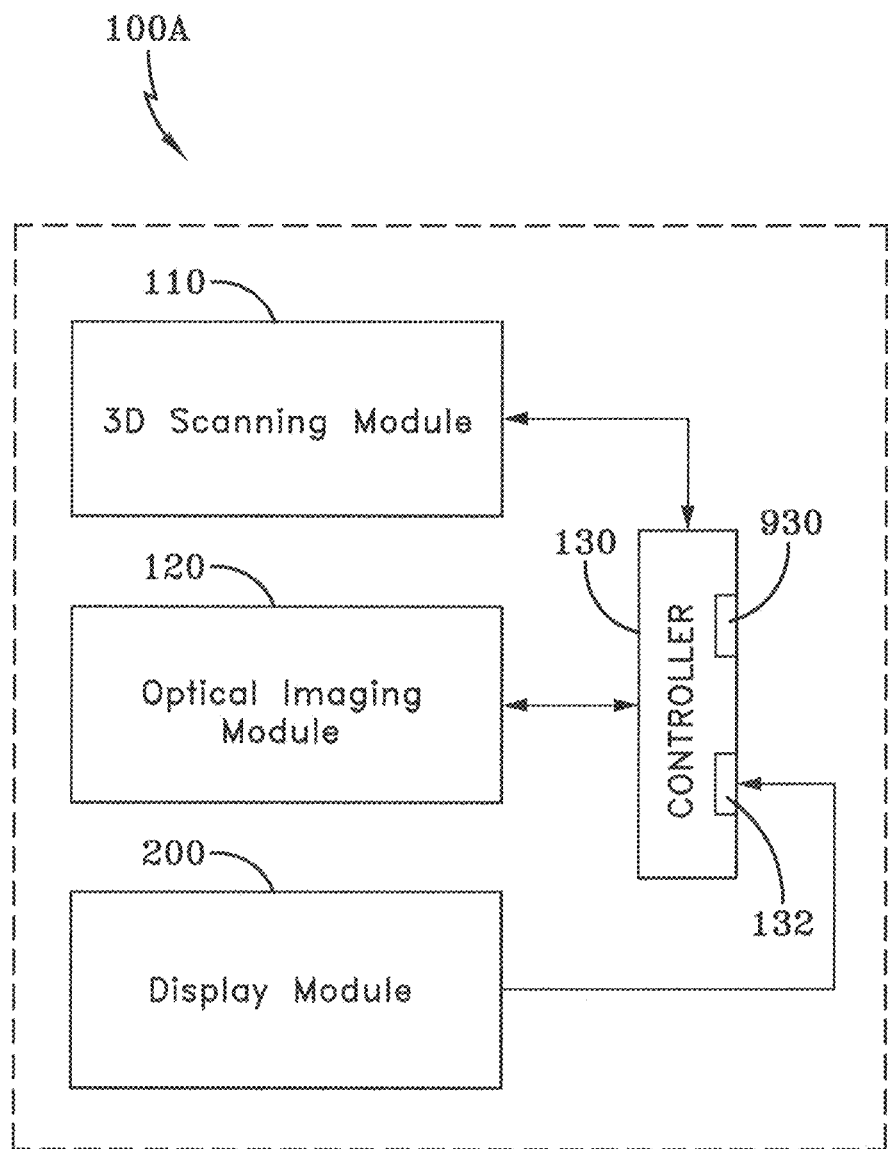
FIG. 2 is a block diagram of another embodiment of the optical imaging system in accordance with the concepts of the present invention.

In another embodiment of the system 100, designated as 100A, may also include a display module 200 in operative communication with the 3D scanning module 110, the optical imaging module 120, and the controller 130 previously discussed, as shown in FIG. 2. Specifically, the display module 200 communicates with the controller 130 through the data interface 132 via a wired or wireless connection. The display module 200 includes any suitable display, such as a liquid crystal display (LCD), or any other display, including but not limited to a two-dimensional (2D) display, a three-dimensional (3D) display, a head-mounted display or a projector.

In another embodiment of the system 100, designated as 100B, the controller 130 of the optical imaging system 100A may be configured with the necessary hardware, software, or combinations thereof, designated as software module 210, to execute a process for registering an optical image and surface topography to other imaging modalities, such as positron emission tomography (PET), single photon emission computed tomography (SPECT), magnetic resonance imaging (MRI), 2D and 3D ultrasound, gamma imaging, optical coherence tomography (OCT), X-ray imaging, and the like. Of course, the software module 210 may be configured so that it is embedded in the controller 130 or may be provided by a remote computing or storage device in communication with the interface 132.

It should be appreciated that the structural features utilized by the embodiments of the optical imaging system 100 and 100A-B discussed above will be presented in detail below.

Figure 4A:
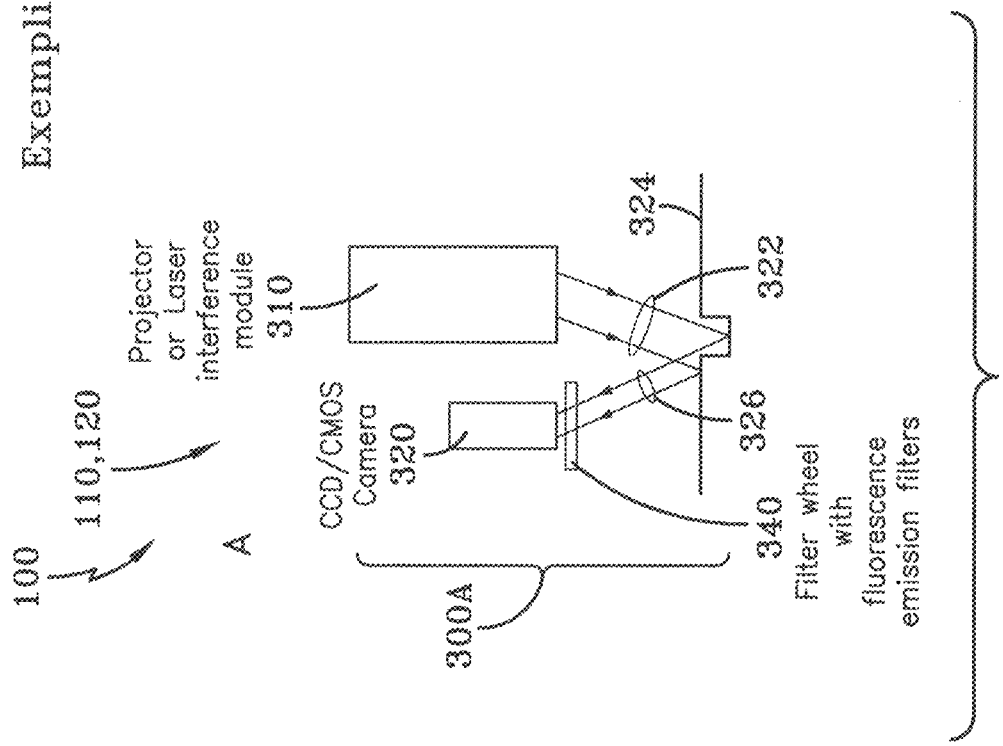
FIG. 4A is a block diagram of one configuration of the optical imaging system in accordance with the concepts of the present invention.

In particular, the functions provided by the 3D scanning module 110 and the imaging module 120 may be embodied in an imaging configuration 300A, as shown in FIG. 4A. In particular, the configuration 300 includes a light emitter module 310 and an image detection module 320, as shown in FIG. 4A. The light emitter module 310 includes any suitable light emitting device for emitting one or more light rays 322, which serves as an excitation/illumination light of a target object 324, and/or for projection of images, such as pattern projection for 3D scanning on a target object 324. In one aspect, the light emitter module 310 may comprise a light projector or laser interference module, which is capable of illuminating the target object 324. The image detection module 320 includes any suitable light detection device configured to detect the light 326 reflected or emitted by the target object 324 in response to being illuminated by the emitted light rays 322 output by the light emitter module 310. In one aspect, the image detection module 320 may comprise a charge coupled imaging device (CCD) or a complementary metal oxide (CMOS) imaging device, however any other suitable imaging device, such as one or more photomultiplier tubes (PMT), one or more avalanche photodiodes (APD), or photodiodes may be used. In addition, an emission filter 340, is operatively positioned in front of the input of the image detection module 320. The emission filter 340 may be configured as a bandpass filter, a long pass filter or a tunable filter, which passes only the wavelengths of light associated with the fluorescence that is emitted by the target object 324 in response to being illuminated by the excitation light 322 that it has absorbed. Furthermore, it should be appreciated that the emission filter 340 blocks the wavelengths of light associated with the excitation light 322. In particular, the emission filter may comprise a filter wheel or other suitable mechanism, which is configured to be selectively actuated so that in a first mode, the light 326 passes through the emission filter 340 before it is captured by the image detection module 320, and in a second mode the filter wheel 340 is rotated or moved so that the light 326 does not pass through the emission filter 340 and is directly detected by the image detection module 320. In one aspect, the emission filter 340 may comprise a fluorescence emission filter. As such, configuration 300 provides that a single imaging device captures topography information of the target object 324 when the filter 340 is not used by the image detection module 320, and captures fluorescence information of the target object 324 when the emission filter 340 is used by the image detection module 320. Thus, during operation of the detection configuration 300, the image detection module 320 captures topography information of the target object 324 when the emission filter 340 is moved out of the detection path of the image detection module 320, and captures fluorescence information of the target object 324 when the emission filter 340 is moved into the detection path of the image detection module 320. In another aspect, the 3D scanning process may be optionally performed without having the emission filter 340 moved out of the detection path of the image detection module 320. For example, the light emitter module 310 may be configured to emit light that is able to pass through the emission filter 340 to enable 3D scanning. One example of this process is that the light emitter module 310 may emit light at a wavelength of about 830 nm, which is able to pass through the band-pass emission filter 340 that is centered at 830 nm, so that 3D scanning is enabled.

In another aspect, the system 100 may capture 3D topography and fluorescence information of the target object 324 sequentially. To achieve this, the system 100 performs 3D scanning first, and then fluorescence imaging second.

In another aspect, the system may capture 3D topography and fluorescence information of the target object 324 concurrently or simultaneously. As such, the image detection module 320 is able to detect both a 3D scanning signal and fluorescence signals during a similar timeframe. Thus, the image frames captured by the image detection module 320 may be designated for the purpose of 3D scanning and fluorescence imaging, respectively. For example, if the frame rate of the image detection module 320 is 30 frames-per-second (FPS), during a one second period 15 frames (e.g. odd frames: 1, 3, 5, 7, 9 . . . ) can be used for capturing 3D topography, while the remaining 15 frames (e.g. 2, 4, 6, 8, 10 . . . ) can be used for fluorescence detection. It should be appreciated that any other combination of image frame designation may be used for concurrent/simultaneous scanning, for example two-thirds of the total image frames may be used for 3D scanning, while one-third of the total image frames are used for fluorescence imaging.

It should also be appreciated that the operation of the light emitter 310 and the image detection module 320 are coordinated by the operation of frame synchronization by the controller 130. For example, if the image detection module 320 is operating at 30 frames-per-second (FPS), the light emitter 310 is able to emit a fringe pattern for capturing 3D topography in 15 frames (e.g. odd frames 1, 3, 5, 7, 9 . . . ) in synchronization with the image detection module 320. The light emitter module 310 is configured to emit a fluorescence excitation light for fluorescence imaging of the remaining 15 frames (e.g. even frames 2, 4, 6, 8, 10 . . . ) in synchronization with the detector 320.

It is also contemplated that the filter wheel may be provided as part of the synchronization if desired, so that the emission filter 340 is moving in and out of the light path, in accordance with the operation mode of the light emitter 310 and the image detection module 320. It should also be appreciated that the synchronization and control of different components of the system 100, including the light emitting module 310 and the image detection module and fluorescence detection module 510 are controlled by the controller 130, where the synchronizing clock signal is generated by the controller 130.

In one aspect, the system 300A is configured to enable color reflectance imaging in addition to 3D scanning and fluorescence imaging of the target object 324. Specifically, if the image detection module 320 is a color imager (e.g. with filter arrays disposed at the imaging sensor level, such as a Bayer pattern filter array), the image detection module 320 is able to detect color information by itself.

In another aspect, if the image detection module 320 may comprise a monochromatic imager, whereby the color image of the target object 324 may be captured, such that the light emitter module 310 projects a red, green and blue wavelength sequentially, and the image detection module 320 captures 3 monochromatic images for red, green and blue reflectance, respectively. In addition, the color image is able to be digitally synthesized. It should also be appreciated that color imaging, fluorescence imaging and 3D scanning can be performed sequentially or concurrently. In the concurrent or simultaneous mode, the image frames are able to be divided for color imaging, fluorescence imaging and 3D scanning, respectively. For example, one-half of the total imaging frames may be used for 3D scanning, one-quarter of the total imaging frames may be used for fluorescence imaging, and one-quarter of the total imaging frames may be used color imaging. It should be appreciated that the light emitter module 310, the image detection module 320 and the filter wheel embodying the emission filter 340 operates in a synchronized manner with the assistance of the controller 130 for the concurrent/simultaneous mode of operation.

In yet another embodiment, the emission filter 340 may comprise a tunable filter. The use of the tunable filter allows hyperspectral imaging to be performed by the configuration 300A to capture multiple light wavelengths. In yet another embodiment, the emission filter 340 may comprise a filter wheel that includes a plurality of narrow-band filters. As such, the configuration 300A is able to capture multiple light wavelengths of reflectance images or absorption images.

In yet another embodiment, the filter wheel embodying the emission filter 340 comprises filters that are suitable for imaging oxygen saturation. For example, images of tissue oxygen saturation (STO2) or venous oxygen saturation (SVO2) may be measured. For example, 660 nm and 950 nm filters may be used to capture the oxygen saturation image. The oxygen saturation can be calculated using the equation: StO2=value of oxygen-saturated hemoglobin/total hemoglobin value (unsaturated+saturated). It should also be appreciated that Cerenkov imaging may also be enabled by using the appropriate filter 340.

It should also be appreciated that polarizers can be used instead of spectral filters, and also another polarizer may be placed in from of the light emitter module 310 to enable polarization imaging, and polarization difference/ratio imaging. It should be appreciated that the different imaging modalities previously discussed may be obtained along with 3D scanning either sequentially or concurrently using the interleaved methods, previously described. It should be appreciated that a plurality of imaging modalities may be enabled by the invention. For example, oxygen saturation imaging, color reflectance imaging, auto-fluorescence imaging and near infrared (NIR) imaging based on extrinsic contrast may be enabled simultaneously at the same time.

In another embodiment, the 3D scanning module 110 and the imaging module 120 may be embodied in an imaging configuration 300B, as shown in FIG. 4B. Specifically, the configuration 300B includes the light emitter module 310, the image detection module 320, the emission filter 340, as previously discussed, with the addition of a fluorescence excitation filter 410. In particular, the fluorescence excitation filter 410 is used in conjunction with the light emitter module 310, and is positioned so that the light emitted from the light emitter module 310 passes through the excitation filter 410 before illuminating the target object 324 being imaged. The fluorescence excitation filter 410 is configured as a bandpass filter, a short pass filter, or a tunable filter that only allows light 322 having rays that are within a range of excitation wavelengths (i.e. excitation light) that are readily absorbable by the target object 324 to pass therethrough. In particular, the fluorescence excitation filter 410 may comprise a filter wheel or other suitable mechanism, which is configured to be selectively actuated so that in a first mode, the light 322 passes through the excitation filter 410, so as to be processed by the emission filter 410, before it is incident on the target object 324, and in a second mode the filter wheel 340 is rotated or moved so that the light 322 does not pass through the excitation filter 340 and is directly emitted from the light emitter module 310 to be incident on the target object 324. In response to the absorption of the light, the target object 324 is able to emit light 326 in the form of fluorescence. As such, in one aspect, during operation of the detection configuration 300B, the image detection module 320 captures topography information of the target object 324 when the excitation filter 410 is moved out of the path of the emitted light 322 and the emission filter 340 is moved out of the detection path of the image detection module 320, and captures fluorescence information of the target object 324 when the excitation filter 410 is moved into the path of the emitted light 322 and the emission filter 340 is moved into the detection path of the image detection module 320. In another aspect, during operation of the detection configuration 300B, the image detection module 320 captures topography information of the target object 324 when the excitation filter 410 is moved out of the path of the emitted light 322, while the emission filter 340 remains in the light path. Alternatively, the image detection module 320 captures topography information of the target object 324 when the emission filter 340 is moved out of the detection path of the image detection module 320, while the excitation filter 410 remains in the light path. In addition, the detection configuration 300B captures fluorescence information of the target object 324 when the excitation filter 410 is moved into the path of the emitted light 322 and the emission filter 340 is moved into the detection path of the image detection module 320.

In another aspect, the system 300B may also capture color images, in addition to 3D topography and fluorescence images.

It should be appreciated that 3D scanning may be performed with either the emission filter 340 or the excitation filter 410 out of the light detection or light emission path.

In a further embodiment, the 3D scanning module 110 and the imaging module 120 may be embodied in an imaging configuration 300C, as shown in FIG. 4C. Specifically, the imaging configuration 300C includes the light emitter module 310, the image detection module 320, the emission filter wheel 340, as previously discussed, with the addition of an excitation light source 450 which operates in conjunction with the fluorescence excitation filter 410. The excitation light source 450 may be configured to generate any suitable light, which then passes through the excitation filter 410. In particular, the fluorescence excitation filter 410 is positioned so that the light 322 emitted from the excitation light source 450 passes therethrough before striking the target object 324 being imaged. In one aspect, during operation of the detection configuration 300C, the image detection module 320 captures topography information of the target object 324 when the emission filter 340 is optionally moved out of the light 326 detection path of the image detection module 320 and the light emitter module 310 is used to generate light 322 to illuminate the target object 324. Alternatively, the image detection module 320 captures fluorescence information from the target object 324 when the emission filter 340 is moved into the detection path of the image detection module 320 and the excitation filter 410 is moved into the path of the light 322 emitted from the light source 450 to illuminate the target object 324. In the concurrent mode, the topography scanning frames and fluorescence imaging frames may be interleaved sequentially, with the light emitter module 310, excitation light source 450 and image detection module 320 being synchronized. In another aspect, the filters 340 and 410 may also be synchronized with the light emitter module 310, excitation light source 450 and detection module to enable concurrent scanning.

It should also be appreciated that the excitation light source 450 may comprise a laser light; a light emitting diode (LED), such as a white LED; an incandescent light; a projector lamp; an arc-lamp, such as xenon, xenon mercury, or metal halide lamp; as well as coherent or in-coherent light sources.

The excitation light source 450 may also comprise a digital (LED-based) projector, and additionally the light source may project spatial frequencies for patterned illumination. For example, a digital projector in conjunction with spectral filters may be used as the light source. In addition, the excitation light source 450 may emit a continuous or pulsed output, and may generate light that is within any desired spectral window of electromagnetic waves.

It should also be appreciated that the excitation light source 450 may also include a light diffuser.

In a further embodiment, the 3D scanning module 110 and the imaging module 120 may be embodied in another imaging configuration 300D, as shown in FIG. 4D. Specifically, the imaging configuration 300D includes the light emitter module 310, the image detection module 320, the emission filter 340, as previously discussed, with the addition of another image detection module 320A and another emission filter 340A. It should be appreciated that the emission filters 340 and 340A are configured as filter wheels, which may be moved into and out of the optical detection path of the respective imaging detection modules 320 and 320A. As such, during operation of the detection configuration 300D, the light emitter module 310 illuminates the target object 324 of the target object with light 322. In addition, to capture topography information of the target object 324 by the image detection modules 320 and 320A, the emission filters 340 and 340A are optionally moved out of the light 326 detection path of the respective image detection modules 320 and 320A. Furthermore, to capture fluorescence information of the target object 324 by the image detection modules 320 and 320A, the emission filters 340 and 340A are moved into the light 326 detection path of the respective image detection modules 320 and 320A. As such, because the configuration 300D utilizes multiple image detection modules 320 and 320A light path obstructions are avoided.

In a further embodiment, the 3D scanning module 110 and the imaging module 120 may be embodied in an imaging configuration 300E, as shown in FIG. 4E. Specifically, the imaging configuration 300E includes the light emitter module 310, the image detection module 320, the emission filter 340, the image detection module 320A and the emission filter 340A, as previously discussed, with the addition of the excitation filter 410. It should be appreciated that the excitation filter 410 may be configured as a filter wheel so as to be selectively moved into and out of the output path of the light emitter 310. As such, during operation of the detection configuration 300E, the image detection modules 320 and 320A capture topography information of the target object 324 when the excitation filter 410 is optionally moved so that the light 322 emitted by the light emitter module 310 to illuminate the target object 324 is not processed by the excitation filter 410, and the emission filters 340 and 340A are optionally moved out of the detection path of the respective image detection modules 320 and 320A to capture the light 326. In addition, the image detection modules 320 and 320A capture fluorescence information of the target object 324 when the excitation filter 410 is moved into the detection path so that the light is processed by the excitation filter 410, and the emission filters 340 and 340A are moved into the detection path of the respective image detection modules 320 and 320A to capture the light 326. As such, because the configuration 300E utilizes multiple image detection modules 320 light path obstructions are avoided. It should be appreciated that in another aspect, the excitation filter 410 may be embodied as a stationary filter without using a filter wheel, and as such the filter 410 need not move in and out of the detection pathway, similar to embodiments previously discussed.

In a further embodiment, the 3D scanning module 110 and the imaging module 120 may be embodied in an imaging configuration 300F, as shown in FIG. 4F. Specifically, the imaging configuration 300F includes the light emitter module 310, the image detection module 320, the emission filter 340, the image detection module 320A and the emission filter 340A, previously discussed, with the addition of the excitation light source 450 which operates in conjunction with the fluorescence excitation filter 410. It should be appreciated that the emission filters 340 and 340A are configured as filter wheels, which may be moved into and out of the optical detection path of the respective imaging detection modules 320 and 320A. As such, during operation of the detection configuration 300F, the image detection modules 320 and 320A capture topography information of the target object 324 when the light emitter 310 is used to emit light 322 to illuminate the target object 324, and the emission filters 340 and 340A are optionally moved out of the detection path of the respective image detection modules 320 and 320A to detect the reflected light 326 from the target object 324. Alternatively, to capture fluorescence information of the target object 324, the light source 450 is used to emit light 322, which is processed by the fluorescence excitation filter 410 that illuminates the target object 324, and the emission filters 340 and 340A are moved into the detection path of the respective image detection modules 320 and 320A to detect the emitted light 326 from the target object 324.

In one aspect, the configuration 300F may capture 3D topography and fluorescence information sequentially. As such, during the collection of topography information the excitation light source 450 and fluorescence excitation filter 410 are not used, while during collection of fluorescence information the light emitter module 310 is not used. In another aspect, the configuration 300F can capture 3D topography and fluorescence information concurrently or simultaneously. As such, the detection modules 320 and 320A may detect both a 3D scanning signal and a fluorescence signal during a similar timeframe. As such, the frames of detection modules 320 and 320A' may be designated for the purposes of 3D scanning and fluorescence imaging, respectively. For example, if the frame rate is 30 frames-per-second (FPS), during a one second period, 15 frames (e.g. odd frames: 1, 3, 5, 7, 9 . . . ) may be used for capturing 3D topography, while the remaining 15 frames (e.g. even frames: 2, 4, 6, 8, 10 . . . ) may be used for fluorescence detection. It should also be appreciated that the any other combination of the frame designation may be used for concurrent scanning (e.g. two-thirds of the total image frames are used for 3D scanning, and one-third of the total image frames are used for fluorescence imaging).

In another aspect, one detection modules 320 can be designated for fluorescence imaging while the other detection modules 320A can be designated for 3D scanning. As such, simultaneous 3D scanning and fluorescence imaging can be enabled.

Figure 5A:
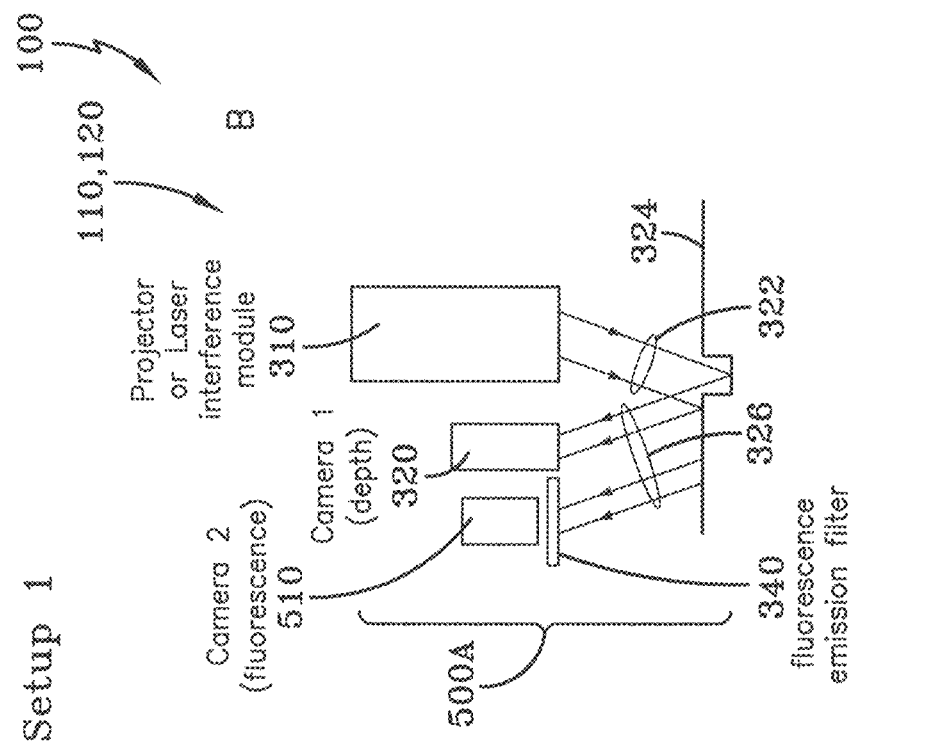
FIG. 5A is a block diagram of one configuration of the optical imaging system in accordance with the concepts of the present invention.

In a further embodiment, the 3D scanning module 110 and the imaging module 120 may be embodied in an imaging configuration 500A, as shown in FIG. 5A. In particular, the configuration 500A includes the light emitter module 310 an image detection module 320, as previously discussed with regard to FIG. 4A, with the addition of a fluorescence detection module 510 that is used in conjunction with the fluorescence emission filter 340. As such, the fluorescence detection module 510 and the emission filter 340 are operatively arranged, such that the light 326 emitted from the target object 324 in response to being illuminated by the light 322 from the light emitter module 310 passes through the emission filter 340 before being detected by the fluorescence detection module 510. In addition, the fluorescence detection module 510 may be configured as any suitable imaging device sensitive to fluorescent light wavelengths, and may comprise in some embodiments a charge coupled imaging device (CCD) or a complementary metal oxide (CMOS) imaging device. As such, during operation of the detection configuration 500A, the light emitter module 310 emits light 322 to illuminate the target object 324, whereupon the image detection module 320 captures topography information, such as depth information, of the target object 324 from the light 322 reflected from the target object 324. In addition, the fluorescence detection module 510 captures fluorescence information of the target object 324 from the light 322 emitted from the target object 324 in response to being illuminated by the light 322 of the light emitter module 310. Thus, the configuration 500A utilizes 2 cameras/sensors/detectors, the image detection module 320 and the fluorescence detection module 510, whereby the image detection module 320 captures topography information of the target object 324, and the fluorescence detection module 510 captures fluorescence information of the target object 324. It should be appreciated that the light emitter module 310 may divide the alternating frames for topography and fluorescence imaging, respectively. For example, odd imaging frames can be used for topography scanning and even imaging frames may be used for fluorescence imaging. In another aspect, the system 500A can also capture color images using the fluorescence detector module 510 or image detection module 320, in addition to 3d topography and fluorescence images.

In a further embodiment, the 3D scanning module 110 and the imaging module 120 may be embodied in an imaging configuration 500B, as shown in FIG. 5B. In particular, the configuration 500B includes the light emitter module 310 an image detection module 320, the fluorescence detection module 510 and the fluorescence emission filter 340, as previously discussed with regard to FIG. 5A, in addition to the fluorescence excitation filter 410. Specifically, the fluorescence excitation filter 410 is configured to be used in conjunction with the light emitter module 310, and is operatively arranged therewith. As such, excitation filter 410 is positioned so that the light emitted from the light emitter module 310 passes through the excitation filter 410 before illuminating the target object 324 being imaged. It should also be appreciated that the excitation filter 410 comprises a filter wheel, which can be selectively moved into or out of the output path of the light emitter module 310. As such, during operation of the detection configuration 500B, the image detection module 320 captures topography information of the target object 324 when the excitation filter 410 is optionally moved out of the light output path of the light emitter module 310 so that the emitted light 322 is not processed by the excitation filter 410 before illuminating the target object 324, whereupon the image detection module 320 detects the light 326 reflected by the target object 324. In addition, the fluorescence detection module 510 captures fluorescence information of the target object 324 when the excitation filter 410 is moved into the light output path of the light emitter 310 so that the emitted light 322 is processed by the excitation filter 410 before illuminating the target object 324, whereupon the fluorescence detection module 510 detects the light 326 emitted from the target object 324 that has been processed by the emission filter 340 as fluorescence information of the target object 324.

In a further embodiment, the 3D scanning module 110 and the imaging module 120 may be embodied in an imaging configuration 500C, as shown in FIG. 5D. Specifically, the imaging configuration 500C includes the light emitter module 310, the image detection module 320, the fluorescence detection module 510, and the emission filter 340, as previously discussed in FIG. 5A, in addition to the excitation light source 450 and the fluorescence excitation filter 410. In particular, the fluorescence excitation filter 410 operates in conjunction with the light source 450, and are operatively positioned so that the light emitted 322 from the light source 450 passes through the excitation filter 410 before illuminating the target object 324 being imaged. As such, during operation of the detection configuration 500C, the image detection module 320 captures topography information of the target object 324 when the light emitter module 310 emits light 322 to illuminate the target object 324, whereupon the image detection module 320 detects the reflected light 326 from the target object 324. Alternatively, the fluorescence detection module 510 captures fluorescence information of the target object 324 when excitation light source 450 generates light 322 that has been processed by the excitation filter 410 to illuminate the target object 324, whereupon the light 326 emitted by the target object 324 in response to being illuminated is processed by the emission filter 340 before being detected by the fluorescence detection module 510 as fluorescence information.

In a further embodiment, the 3D scanning module 110 and the imaging module 120 may be embodied in an imaging configuration 500D, as shown in FIG. 5D. Specifically, the imaging configuration 500D includes the light emitter module 310, the image detection module 320, the image detection module 320A, the fluorescence imaging module 510, and the emission filter 340, as previously discussed in FIG. 5A, with the addition of the image detection module 320A. As such, during operation of the detection configuration 500D to detect topography information of the target object 324, the light emitter module 310 emits light 322 to illuminate the target object 324, whereupon the image detection modules 320 and 320A capture topography information, such as depth information, of the target object 324 from the light 322 reflected from the target object 324. In addition, the fluorescence detection module 510 captures fluorescence information of the target object 324 from the light 326 emitted from the target object 324 in response to being illuminated by the light 322 of the light emitter module 310. Thus, the configuration 500D utilizes multiple cameras/sensors/detectors, including the image detection module 320 and 320A and the fluorescence detection module 510, whereby the image detection modules 320 and 320A capture topography information of the target object 324, and the fluorescence detection module 510 captures fluorescence information of the target object 324. Thus, because the configuration 500D utilizes multiple image detection modules 320 light path obstructions are avoided. It should be appreciated that one of the detection modules 320, 320A may be optionally designated to perform other specific imaging, such as color reflectance imaging.

In a further embodiment, the 3D scanning module 110 and the imaging module 120 may be embodied in an imaging configuration 500E, as shown in FIG. 5E. Specifically, the imaging configuration 500E includes the light emitter module 310, the image detection module 320, the fluorescence imaging module 510, the image detection module 320A, as previous discussed with regard to FIG. 5D, in addition to the excitation filter 410. In particular, the excitation filter 410 is configured to operate in conjunction with the light emitter module 310, and is operatively positioned so that the light emitted from the light emitter module 310 passes through the excitation filter 410 before illuminating the target object 324 being imaged. In particular, the excitation filter 410 may comprise a filter wheel or other suitable mechanism, which is configured to be selectively actuated so that in a first mode, the light 322 passes through the excitation filter 410, so as to be processed by the emission filter 410, before it illuminates the target object 324, and in a second mode the filter wheel 340 is rotated or moved so that the light 322 does not pass through the excitation filter 340 and is directly emitted from the light emitter module 310 to illuminate the target object 324. As such, during operation of the detection configuration 300E, the image detection modules 320 and 320A capture the reflected light 326 as topography information of the target object 324 when the excitation filter 410 is optionally moved so that the light 322 emitted by the light emitter module 310 to illuminate the target object 324 is not processed by the excitation filter 410. In addition, the fluorescence detection module 510 captures fluorescence information of the target object 324 from the light 326 emitted from the target object 324 in response to being illuminated by the light 322 of the light emitter module 310 that has been processed by the excitation filter 410. As such, because the configuration 300E utilizes multiple image detection modules 320 light path obstructions are avoided. It should be appreciated that the controller 130 synchronizes and actuates the light emitter module 310, the image detection module 320, the fluorescence imaging module 510, the image detection module 320A, and the excitation filter wheel 410. It should be also appreciated that the system 500E may use the interleaved method previously described to split the projection and image frames, with the aid of the controller 130.

In a further embodiment, the 3D scanning module 110 and the imaging module 120 may be embodied in an imaging configuration 500F, as shown in FIG. 5F. Specifically, the imaging configuration 500F includes the light emitter module 310, the image detection module 320, the image detection module 320A, the fluorescence imaging module 510, the emission filter 340, the light source 450 and the excitation filter 410, as previously discussed with regard to FIG. 5C, with the addition of the image detection module 320A. As such, during operation of the detection configuration 500F, the image detection modules 320 and 320A capture topography information of the target object 324 when the light emitter module 310 emits light 322 to illuminate the target object 324, whereupon the image detection modules 320 and 320A detect the reflected light 326 from the target object 324. It should be appreciated during the topography information collection process, the excitation light source 450 is not used, while the excitation filter 410 is not used. Alternatively, the fluorescence detection module 510 captures fluorescence information of the target object 324 when excitation light source 450 generates light 322 that has been processed by the excitation filter 410 to illuminate the target object 324, whereupon the light 326 emitted by the target object 324 in response to being illuminated is processed by the emission filter 340 before being detected by the fluorescence detection module 510 as fluorescence information. It should be appreciated that the light emitter module 310 is not used during the fluorescence information collection process.

In further embodiments, the 3D scanning module 110 and the imaging module 120 may be embodied in another imaging configuration 600A, as shown in FIG. 6A. Specifically, the imaging configuration 600A includes the light emitter module 310, the image detection module 320, the fluorescence imaging module 510, and the emission filter 340, as previously discussed with regard to FIG. 5A, in addition to a beam splitter 610. In one aspect, the beam splitter 610 may comprise a dichroic filter or any suitable device capable of reflecting light of one range of wavelengths, and passing light of another range of wavelengths. The image detection module 320 and the fluorescence imaging module 510 are positioned at an angle to each other, such as a substantially right angle, while the beam splitter 610 is positioned at an oblique angle, such as about a 45-degree angle, relative to the image detection module 320 and the fluorescence imaging module 510. As such, during operation of the detection configuration 600A, the light emitter module 310 emits light 322 to illuminate the target object 324, whereupon the light 326 reflected and emitted by the target object 324 in response to being illuminated is received by the beam splitter 610, where a portion 620 of the light 326 is permitted to pass through the beam splitter 610 for receipt by the image detection module 320 to capture topography data of the target object 324. In addition, another portion 622 of the light 326 is reflected by the beam splitter 610, whereupon it is directed to pass through the emission filter 340 for receipt by the fluorescence imaging module 510 to capture fluorescence information of the target object 324. In another aspect, the beam splitter 610 may be splitting light based on polarization. It should be appreciated that the beam splitter 610 may include, but is not limited to a plate beam splitter, a cube beam splitter, a non-polarizing beam splitter, a lateral displacement beam splitter, a pent-prism beam splitter, a wire grid polarizing beam splitter, or a polarizing beam splitter. It should also be appreciated that color image can also be captured by either detector module 510 or the image detection module 320.

In further embodiments, the 3D scanning module 110 and the imaging module 120 may be embodied in another imaging configuration 600B, as shown in FIG. 6B. Specifically, the imaging configuration 600B includes the light emitter module 310, the image detection module 320, the fluorescence imaging module 510, the emission filter 340, and the beam splitter 610, as previously discussed with regard to FIG. 6A, in addition to the excitation filter 410. In particular, the excitation filter 410 is operatively arranged relative to the light emitter 310, so that light 622 output thereby is processed by the excitation filter 410. It should be appreciated that the excitation filter 410 is configured as a filter wheel or other movable device, which can be moved so that the light output by the light emitter 310 is selectively processed or not processed by the excitation filter 410. As such, during operation of the configuration 600B, the excitation filter 410 is moved so that the light 322 emitted by the light emitter 310 is not processed by the excitation filter 410 to illuminate the target object 324, whereupon the light 326 reflected by the target object 324 in response to being illuminated is received by the beam splitter 610. Next, the reflected and emitted light 326 from the target object 324 is received by the beam splitter 610, where the portion of the light 620 is permitted to pass through the beam splitter 610 for receipt by the image detection module 320 to capture topography data of the target object 324. In order to detect fluorescence information, the excitation filter 410 is moved so that the light emitted by the light emitter 310 is processed by the excitation filter 410 to illuminate the target object 324, whereupon the light 326 emitted from the target object 324 in response to being illuminated is received by the beam splitter 610. Next, the portion 622 of the light emitted light 326 is reflected by the beam splitter 610, whereupon it is directed to pass through the emission filter 340 for receipt by the fluorescence imaging module 510 to capture fluorescence information of the target object 324.

In further embodiments, the 3D scanning module 110 and the imaging module 120 may be embodied in an imaging configuration 600C, as shown in FIG. 6C. Specifically, the imaging configuration 600C includes the light emitter module 310, the image detection module 320, the fluorescence imaging module 510, the emission filter 340, and the beam splitter 610, as previously discussed in FIG. 6A, in addition to the light source 450 and excitation filter 410. In particular, the fluorescence excitation filter 410 is configured for use in conjunction with the excitation filter 410, and is operatively positioned so that the light 322 emitted from the light emitter module 310 passes therethrough before illuminating the target object 324 being imaged. As such, during operation of the detection configuration 600C, the light emitter module 310 emits light 322 to illuminate the target object 324, whereupon the light 326 reflected by the target object 324 in response to being illuminated is received by the beam splitter 610, where a portion 620 of the light 326 is permitted to pass through the beam splitter 610 for receipt by the image detection module 320 to capture topography data of the target object 324. Alternatively, to detect fluorescence information from the target object 324, the excitation light source 450 is operated to generate light 322 that is processed by the excitation filter 410 to illuminate the target object 324. As such, the light 326 emitted from the target object 324 in response to being illuminated is received by the beam splitter 610. Next, the portion 622 of the light emitted light 326 is reflected by the beam splitter 610, whereupon it is directed to pass through the emission filter 340 for receipt by the fluorescence imaging module 510 to capture fluorescence information of the target object 324.

In further embodiments, the 3D scanning module 110 and the imaging module 120 may be embodied in an imaging configuration 700A, as shown in FIG. 7A. Specifically, the imaging configuration 700A includes the light emitter module 310, the image detection module 320, the fluorescence imaging module 510, the emission filter 340, as previously discussed with regard to FIG. 6A, with the addition of the beam splitter 610A, the image detection module 320A, the fluorescence imaging module 510A and the emission filter 340A. As such, the image detection module 320 and the fluorescence imaging module 510 are positioned at a substantially right angle to each other, while the image detection module 320A and the fluorescence imaging module 510A are also positioned at a substantially right angle to each other. In addition, the beam splitter 620 is positioned at an oblique angle, such as about 45 degrees, relative to the image detection module 320 and the fluorescence imaging module 510. Similarly, the beam splitter 620A is positioned at an oblique angle, such as about 45 degrees, relative to the image detection module 320A and the fluorescence imaging module 510A. As such, during operation of the detection configuration 700A, the light emitter module 310 emits light 322 to illuminate the target object 324, whereupon the light 326 reflected and emitted by the target object 324 in response to being illuminated is received by the beam splitters 610 and 610A, where a portion 620 of the light 326 is permitted to pass through the beam splitters 610 and 610A for receipt by the image detection modules 320 and 320A to capture topography data of the target object 324. In addition, another portion 622 of the light 326 received by the beam splitters 610 and 610A is reflected by the beam splitters 610 and 610A, whereupon it is directed to pass through the emission filters 340 and 340A for receipt by the fluorescence imaging modules 510 and 510A to capture fluorescence information of the target object 324.

In further embodiments, the 3D scanning module 110 and the imaging module 120 may be embodied in an imaging configuration 700B, as shown in FIG. 7B. Specifically, the imaging configuration 700B includes the light emitter module 310, the image detection module 320, the fluorescence imaging module 510, the emission filter 340, the beam splitter 610A, the image detection module 320A, the fluorescence imaging module 510A and the emission filter 340A, as previously discussed in FIG. 7A, in addition to the excitation filter 410. In particular, the excitation filter 410 is operatively arranged relative to the light emitter 310, so that light output thereby is processed by the excitation filter 410. It should be appreciated that the excitation filter 410 is configured as a filter wheel or other movable device, which can be moved so that the light output by the light emitter 310 is selectively processed or not processed by the excitation filter 410. As such, during operation of the configuration 700B, the excitation filter 410 is optionally moved out of the light output path of the light emitter module 310 so that the light 322 emitted by the light emitter 310 is not processed by the excitation filter 410, whereupon light 326 reflected from the target object 324 in response to being illuminated by the light 322 emitted by the light emitter 310 is received by the beam splitters 610 and 610A, where the portion 620 of the light 326 is permitted to pass through the beam splitters 610 and 610A for receipt by the respective image detection modules 320 and 320A to capture topography information of the target object 324. In addition, to collect fluorescence information from the target object 324, the excitation filter 410 is moved into the light output path of the light emitter so that light emitted thereby is processed by the excitation filter 410. As such, the light 326 emitted from the target object 324 in response to being illuminated by the processed light 322 is received by the beam splitters 610 and 610A, whereupon it is directed or reflected to pass through the emission filters 340 and 340A for receipt by the fluorescence imaging modules 510 and 510A to capture fluorescence information of the target object 324. It should be appreciated that in another aspect of the present invention, the excitation filter 410 may be embodied as a stationary filter without using a filter wheel, and as such the filter 410 need not move in and out of the detection pathway, similar to the embodiments previously discussed.

In further embodiments, the 3D scanning module 110 and the imaging module 120 may be embodied in an imaging configuration 700C, as shown in FIG. 7C. Specifically, the imaging configuration 700C includes the light emitter module 310, the image detection module 320, the fluorescence imaging module 510, the emission filter 340, the beam splitter 610, the image detection module 310A, the fluorescence imaging module 510A, the emission filter 340A, and the beam splitter 610A, as previously discussed with regard to FIG. 7A, with the addition of the excitation light source 450 and excitation filter 410. As such, during operation of the detection configuration 700C, the light emitter module 310 emits light 322 to illuminate the target object 324, whereupon the light 326 reflected by the target object 324 in response to being illuminated is received by the beam splitters 610 and 610A, where a portion 620 of the light 326 is permitted to pass through the beam splitters 610 and 610A for receipt by the image detection modules 320 and 320A to capture topography data of the target object 324. In addition, to collect fluorescence information from the target object 324, the excitation light source 450 is activated so that light 322 emitted therefrom is processed by the excitation filter 410. As such, the light 326 emitted from the target object 324 in response to being illuminated by the processed light output through the excitation filter 410 is received by the beam splitters 610 and 610A. The received light 326 is then reflected by the beam splitters 610 and 610A, whereupon the portion 622 of the light 326 is directed, or otherwise reflected, to pass through the emission filters 340 and 340A for receipt by the fluorescence imaging modules 510 and 510A to capture fluorescence information of the target object 324.

In further embodiments, the 3D scanning module 110 and the imaging module 120 may be embodied in an imaging configuration 800A, as shown in FIG. 8A. In particular, the configuration 800A includes the light emitter module 310, and the image detection module 320, previously discussed, with regard to FIG. 4A, with the addition of a filter wheel 810, and a filter wheel 820. In particular, the filter wheel 810 is configured to be used in conjunction with the light emitter module 310, and includes the excitation filter 410 and a polarizer 830 carried thereon. In addition, the filter wheel 820 includes both the emission filter 340 and an analyzer 840 carried thereon. In particular, the filter wheel 810 may be selectively moved relative to the light emitter module 310, such that in one state, the excitation filter 410 processes the light 322 emitted by the light emitter module 310 that is used to illuminate the target object 324, and such that in another state the polarizer 830 processes the light 322 emitted from the light emitter module 310 that is used to illuminate the target object 324. Similarly, the filter wheel 820 may be selectively moved relative to the image detection module 320, such that in one state, the emission filter 340 processes the light 326 emitted from the target object 324 in response to being illuminated, and such that in another state the analyzer 840 processes the light 326 reflected from the target object 324 in response to being illuminated. As such, during operation of the detection configuration 800A, when topography information of the target object 324 is desired to be captured, the polarizer portion 830 of the filter wheel 810 is moved into a position to process the light 322 emitted by the light emitter module 310, such that the processed light 322 illuminates that target object 324. In addition, the analyzer portion 840 of the filter wheel 820 is moved into the detection path of the image detection module 320 so that light 326 reflected by the target object 324 in response to being illuminated is processed by the analyzer 840 before being detected by the image detection module 320. In one aspect, the analyzer 840 and the polarizer 830 may be arranged in a co-polarization configuration to detect photons reflected off of the surface of the target object 324 and to minimize the detection of photons diffused into the target object 324. Alternatively, when fluorescence information of a target object 324 is desired to be captured, the excitation filter 410 of the filter wheel 810 is moved to a position to process the light 322 emitted by the light emitter module 310, such that the processed light 322 illuminates the target object 324. In addition, the emission filter 340 is moved into the detection path of the image detection module 320 so that light 326 emitted by the target object 324 in response to being illuminated by the processed light 322 light emitter 310 passes through the emission filter 340 before being detected by the image detection module 320. In one aspect, during fluorescence detection, the analyzer 840 and the polarizer 830 may remain in the illumination and detection path, such that the analyzer 840 and the polarizer 830 are arranged in a cross-polarization configuration to reduce specular reflection of the target object 324.

In further embodiments, the 3D scanning module 110 and the imaging module 120 may be embodied in an imaging configuration 800B, as shown in FIG. 8B. In particular, the configuration 800B includes the light emitter module 310, the image detection module 320, the filter wheel 810 that includes both the excitation filter 410 and the polarizer 830 carried thereon, as previously discussed with regard to FIG. 8B, with the addition of the analyzer 840 that is used in conjunction with the image detection module 320 and the fluorescence detection module 510 that is used in conjunction with the image detection module 320 and the emission filter 340 that is used in conjunction with the fluoresce detection module 510. That is, the analyzer 840 is positioned relative to the detection path of the image detection module 320, while the emission filter 340 is positioned relative to the detection path of the fluorescence imaging module 510. As such, during operation of the detection configuration 800B, the image detection module 320 captures topography information of the target object 324 when the polarizer portion 830 of the filter wheel 810 is moved into a position to process the light 322 emitted by the light emitter module 310. In one aspect, the analyzer 840 and the polarizer 830 may be arranged in a co-polarization configuration to detect photons reflected off of the surface of the target object 324 and to minimize the detection of photons diffused into the target object 324. Next, the light 326 reflected from the target object 324 in response to being illuminated is processed by the analyzer 840 before being detected by the image detection module 320 as topography information. In addition, to capture fluorescence information of the target object 324, the excitation filter 410 of the filter wheel 810 is moved to a position to process the light 322 emitted by the light emitter 310. As such, the light 326 emitted from the target object 322 in response to being illuminated by the light 322 emitted from the light emitter module 310 is processed by the emission filter 340 before being detected by the fluorescence imaging module 510.

Thus, the use of the polarizer and analyzer pair of the configurations 800A and 800B, shown in FIGS. 8A-B, allows the process of polarization gating to be performed, so as remove diffused photons that may travel in the target object 324 as it is illuminated by the light emitter 310 during the imaging process. This ensures that the surface topography scan is performed accurately. That is, when incoming structured light is linearly polarized, a portion of the photons are reflected at the surface of the target object 324 with a well preserved polarization state, while the polarization states of the diffused photons will be more randomly distributed. As such, the polarizer/analyzer pair used by the present invention allows polarization gating to be performed, thereby allowing the surface reflected photons to be separated from the diffused photons during the collection to topography information of the target object 324.

Measurement Data Representation

It should be appreciated that topography measurements that are obtained by the present invention are represented as a map of depth z, and as a function of spatial position x and y, which may be expressed as $fz_{ij}=\{(x_i, y_j); i=1, 2 \ldots L, j=1, 2 \ldots M\}$. In the present invention, 3D (three-dimensional) surface topography information combined with fluorescence imaging information is able to identify a scalar value that is associated with each point on a surface being imaged of the target object 324. This association of values is referred to as "point clouds," which are expressed as $P_i=x_i, y_i, I_i$; where ($i=1, 2, 3 \ldots N$), and $I_i$ represents the fluorescence imaging value at the ith surface point in the data set. Similarly, if both color reflectance information is also captured from the target object 324 and integrated with fluorescence and topography information also captured from the target object 324, the point clouds are expressed as $P_i=(x_i, y_i, z_i, I_i, R_i, G_i, B_i)$, where i=1, 2, 3 ... N, with vector ($R_i, G_i, B_i$) representing red, green, and blue color components. If multiple channels of fluorescence information are captured along with color reflectance from the target object 324, the point clouds are expressed as $P_i=x_i, y_i, z_i, I_i, R_i, G_i, B_i$), where i=1, 2, 3 ... N, with $I_i$ representing the fluorescence channel 1, and $F_i$ representing the fluorescence channel 2, with each channel having a different wavelength.

In another embodiment, the topography data may be represented by polygon meshes in lieu of point clouds, as meshes reduce computational time. The mesh faces may comprise triangles, quadrilaterals, or any other convex polygons. For example, the mesh faces may comprise vertex-vertex meshes, face-vertex meshes, winged-edge meshes and render dynamic meshes.

In other embodiments of the present invention, active illumination of the scene or target object 324 being imaged may be achieved by configuring the light emitter module 310 to use a spatially varying light intensity pattern. For example, the light emitter module 310 may be configured as a digital projector or a light source that is modulated by a spatial light modulator to provide structured illumination. The structured illumination can be either 2D (two-dimensional) or 3D (three-dimensional). The relationship between the image detection module 320 that captures topography information, the light emitter module 310, and the target object 324 can be expressed by a triangulation equation.

Figure 8C:
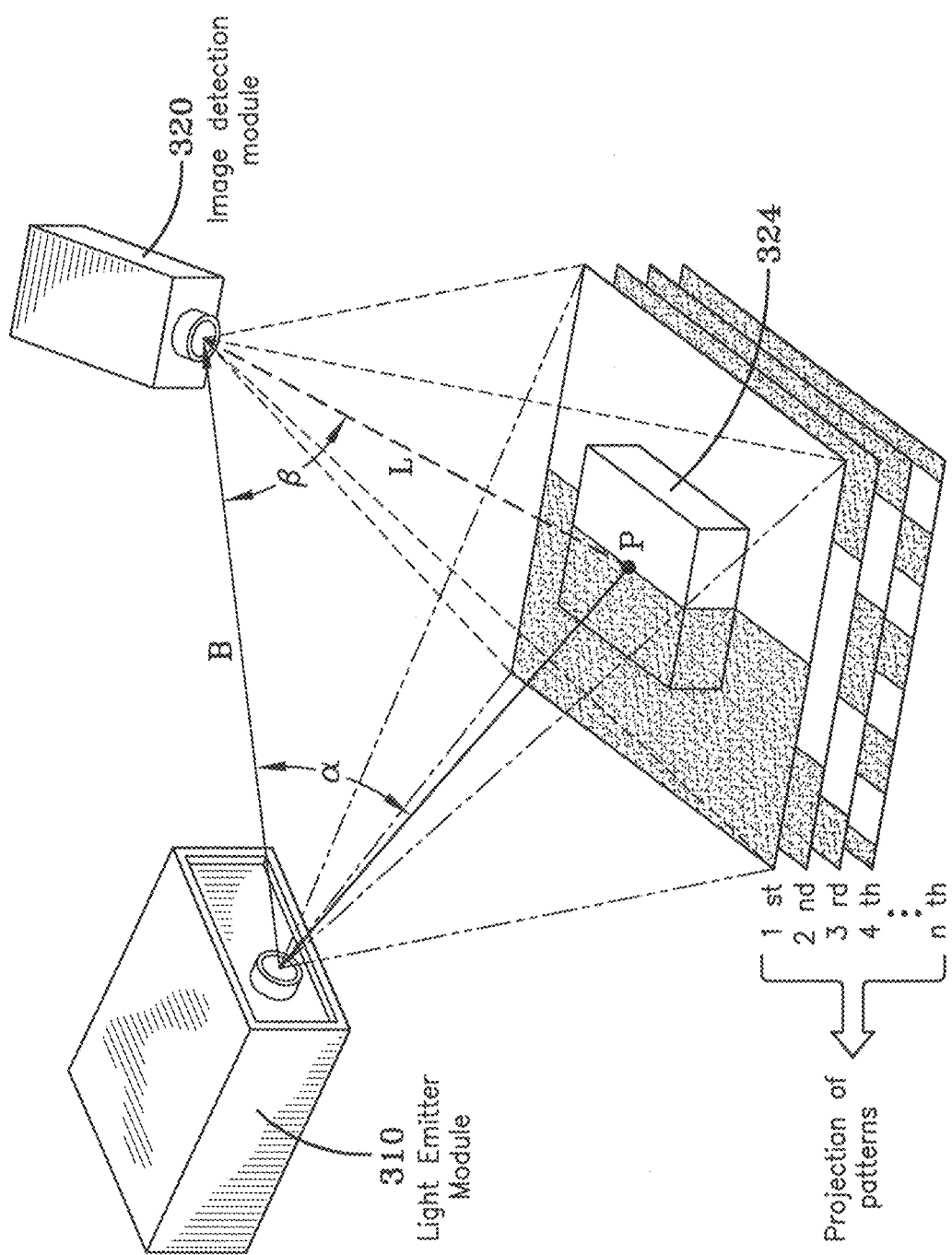
FIG. 8C is a schematic diagram showing the triangulation process utilized by a configuration of the optical imaging system in accordance with the concepts of the present invention.

With reference to FIG. 8C, the geometric relationship between the image detection module 320, the light emitter module 310, and an object surface point on the target object 324 may be expressed by the triangulation principle using the following equation:

$$L = B \frac{\sin(\alpha)}{\sin(\alpha + \beta)}.$$

In particular, the light emitter module 310 may utilize various algorithms or techniques to generate structured light illumination of the target object 324. For example, the techniques or methods for projecting structured illumination that may be utilized by the light emitter module 310 may include, but are not limited to: 1.) sequential projection techniques, such as binary patterns and gray coding, gray-level patterns, phase shift, photometric stereo techniques, and a hybrid method of phase shifting and gray coding; 2.) full-frame spatially varying color patterns, such as that provided by a rainbow 3D camera, continuously varying color coding, stripe indexing (single shot), stripe indexing using colors, stripe indexing using segment patterns, stripe indexing using repeated gray-scale patterns, stripe indexing based on a De Bruijn sequence; and 3.) grid indexing (2D spatial grid patterns), such as a pseudo-random binary array (PRBA), mini-patterns used as code words, color-coded grids, a 2D array of color-coded dots; and 4.) hybrid methods that combine the methods presented above.

The light emitter module 310 and the image detection module 320 may be calibrated to establish the relationship between depth and the spatial location of a pixel on the image of the target object 324 captured by the image detection module 320. In one aspect, the light emitter module 310 may be calibrated for both intensity and geometry, using any suitable target, such as a checkerboard pattern or an array of dots, for example.

Imaging and Co-Registration I

Figure 9:
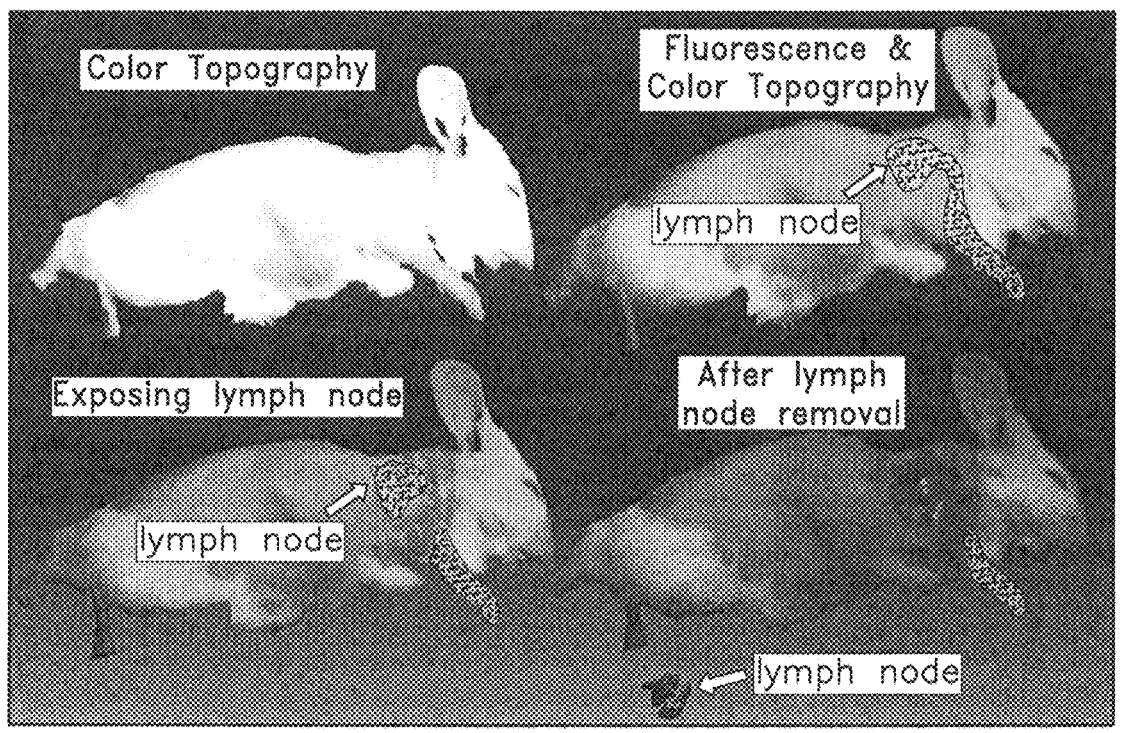
FIG. 9 is an image showing the co-registration of various images as performed by the optical imaging system in accordance with the concepts of the present invention.
Figure 10:
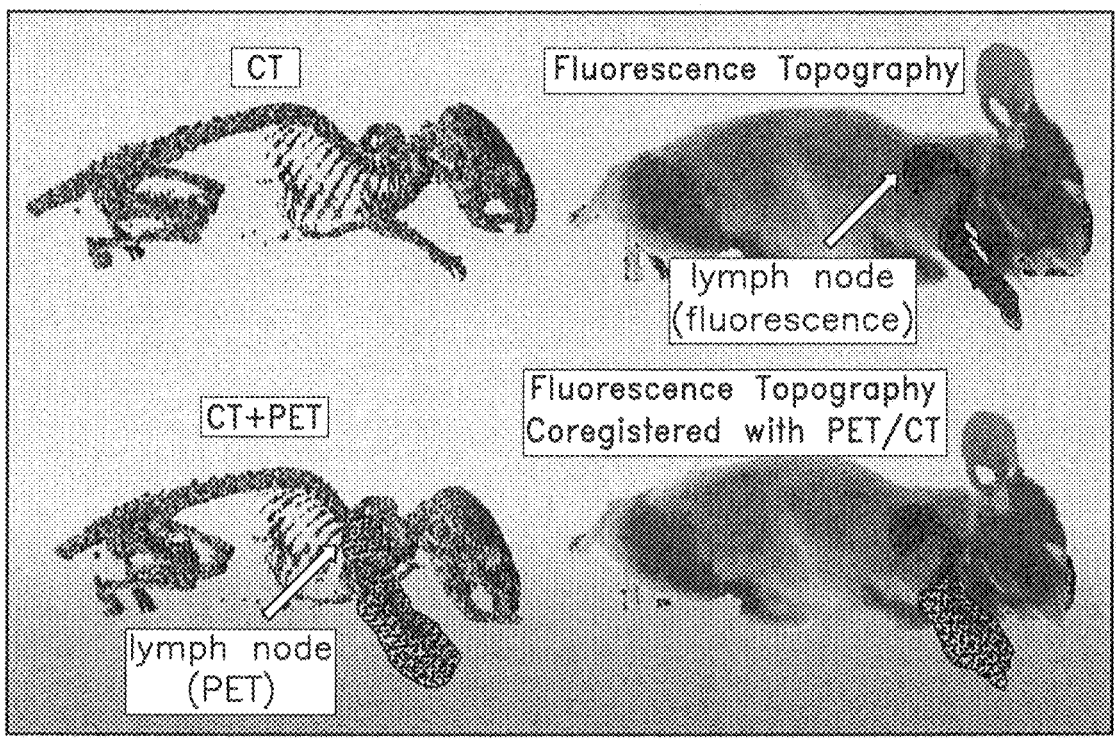
FIG. 10 is another image showing the co-registration of various images as performed by the optical imaging system in accordance with the concepts of the present invention.

Thus, the embodiments of the present invention are able to intraoperatively capture, and combine through co-registration, surface topography information and fluorescence imaging information of the target object 324, as shown in FIG. 9. For example, in some embodiments, the light source 310 may comprise a NIR (near-infrared) light source to provide fluorescence excitation of the target object 324, while a white light source may also be integrated into the embodiments of the present invention to provide surgical illumination. Additionally, the image detection module 320 may comprise a CCD (charge coupled device) imaging sensor or CMOS (complementary metal oxide) imaging sensor, which is capable of capturing color or grayscale images. Furthermore, in other embodiments, the present invention is capable of co-registration between intraoperative fluorescence imaging information and/or color reflectance imaging information, and any other preoperative imaging data/information, such as positron emission tomography (PET) data, computerized tomography (CT) data, or magnetic resonance imaging (MRI) data of the target object 324, as shown in FIG. 10. In addition, such embodiments of the present invention have been utilized to combine, through co-registration, intraoperative fluorescence imaging and/or color reflectance imaging data, with preoperative PET/CT data, along with fluorescence imaging data to facilitate guided surgery and surgical planning. In addition, the image data from each of the imaging modalities may be represented using different colors. For example, CT data may be represented in a blue color, PET data may be represented in a red color, and fluorescence data may be represented in a green color. In one aspect, the 3D model with the multimodal image data may be rotated upon user input to facilitate visualization.

In another embodiment, preoperative MRI data captured by an MRI scanner, and intraoperative fluorescence data, color reflectance data and topography data that is generated by the system 100 may be registered together in an image to facilitate brain surgery. In one aspect, contrast agents, such as indocyanine green (ICG) or 5-aminolevulinic acid (5-ALA) may be used to guide brain surgery. The preoperative MRI data can enable surgical navigation using tracking technologies, such as optical tracking or electromagnetic tracking, and intraoperative fluorescence imaging, color reflectance and topography data can provide accurate image guidance. The system 100 is also enabled to integrate surgical navigation and intraoperative imaging with visualization of co-registered data. In one aspect, 5-ALA fluorescence can be used to image the brain tumor in order to correlate with images that are detected by surgical navigation based on preoperative MRI data. In another aspect, ICG fluorescence can image vascularity of tissues to provide useful information in addition to the preoperative MRI. In one aspect, the light source of system 100 may be operated at a predetermined frequency for a predetermined duration (eg. 10 ms per exposure, 12 exposures per second) to minimize the photo-bleach or photo-toxicity of contrast agents. The registration algorithm comprises surface-based registration, feature-based registration, point-based registration, intensity-based registration, or combinations thereof. The registration can be performed using point cloud representation, or polygon mesh representation, or combinations thereof. In one aspect, the deformation of the brain can be calculated with biomechanical modeling using finite element method (FEM) to facilitate the registration process.

In other embodiments, the visual data may be clearly visualized by making each type of data "transparent" for representation on any suitable display. Furthermore, the transparency level of each type of image data may be tuned and changed for improved visualization.

In yet another embodiment, a contrast agent that is dual-labeled (e.g. a contrast agent that is both fluorescent and also labeled with a radioisotope for PET or SPECT imaging) may be used with the system 100. For instance, an antibody can be labeled with both positron-emitting radioisotopes and fluorescent moieties. The dual labeled contrast agent may be injected into a human target 324 for imaging purposes. As the contrast agent produces both positrons and fluorescence, the location of the target 324 can be imaged with both PET and fluorescence imaging, with a source of the signal for both imaging modalities coming from the same source. This facilitates correlation between the PET data and the fluorescence data. It should be appreciated the contrast agents may be labeled to be used for more than 2 modalities (e.g. MRI, PET and fluorescence). It should be further appreciated that contrast agents can be dual-labeled for other combinations of imaging modalities (e.g. MRI and fluorescence, SPECT and fluorescence, etc.).

Imaging and Co-Registration II

In other embodiments of the system 100, the image detection module 320 may comprise a high-speed CMOS (complementary metal-oxide sensor) sensor, while an amplitude-splitting technique may be utilized to increase the imaging speed of the embodiments of the present invention. For example, the image detection module 320 may comprise a high-speed CMOS color sensor, while the fluorescence imaging module 510 may comprise a NIR (near infrared) sensitive CMOS sensor that is utilized in conjunction with a NIR beam splitter, such as beam splitter 610. For topography imaging or scanning, the image detection module 320 may comprise a fast CMOS sensor (LUPA1300-2, ON Semiconductor, Inc.) that has a frame rate of about 500 frame-per-second (fps). As such, the present invention is able to reduce the amount of time needed to perform topography imaging or scanning over that of past generation imaging systems. For fluorescence imaging, the fluorescence detection module 510 may comprise a NIR-sensitive CMOS sensor (MT9V032, Aptina). This sensor offers a high quantum efficiency of about 40% at 800 nm, and a high frame rate of about 60 fps. In addition, this sensor uses a NIR-sensitive monochrome sensor, which improves the detection limit to reach a pM level ICG (indocyanine green) concentration applied to the target object 324, which is used to facilitate fluorescence imaging. In addition, the beam splitter 610 used by the embodiments of the present invention may comprise a short-pass dichroic beam splitter (FF756-SDi01-25x36, Semrock) to separate the visible light component reflected from the target object 324 and the NIR component (fluorescence) emitted from the target object 324 after being illuminated. In addition, the emission filter 340 used by the embodiments of the present invention may comprise an NIR (near infrared) emission filter (#84-123, Edumund Optics, 832 nm CWL with 37 nm bandwidth, OD 6) to minimize cross-talk.

The embodiments of the system 100 of the present invention are advantageous, as they enable concurrent topography imaging/scanning and NIR fluorescence imaging/scanning, while shortening the total overall imaging time. For example, the NIR fluorescence sensor comprising the fluorescence detection module 510 is capable of capturing fluorescence information, such as NIR fluorescence, from the target object 324, so as to provide real-time 2D (two-dimensional) fluorescence guidance during a surgical procedure, while a color imaging sensor, such as that provided by the image detection module 310, captures 3D (three-dimensional) topography information and color reflectance information.

In addition, the embodiments of the present invention may use an image detection sensor 320 having an f-number, such as F/4, to provide a large depth of field and high light collection efficiency. The image detection sensor 320 may utilize a CMOS light detector. For topography scanning of the target object 324, as performed by the system 100 of the present invention, high-resolution imaging at a fast frame rate is desired to reduce imaging or scanning time of the target object 324. With regard to standard CCD imaging sensors, its read-out rate is intrinsically limited by the charge-shifting mechanisms and the pixel numbers; and binning is typically needed to achieve faster frame rates, which substantially reduces the effective resolution. Compared to CCD sensors, the CMOS sensor utilized by the image detection sensor 320 of the present invention offers high resolution imaging with faster frame rates and direct access to each pixel, without the need for binning. In addition, the low power consumption and low cost of CMOS sensors are also desirable.

Furthermore, some embodiments of the present invention are configured, whereby the excitation light source 450 includes a filtered LED (light emitting diode) array, while the light emitter module 310 comprises a compact digital projector. The customized LED array of the excitation light source 450 is used for illuminating a region of the target object 324 that is well defined and uniform, such that in some embodiments only a specific surgical field will be illuminated, therefore reducing the background noise. In some embodiments, the excitation light source 450 of the present invention may use a high power 780 nm LED array. In addition, in some embodiments, the excitation filter 410 (#84-106, Edmund Optics, 775 nm CWL with 46 nm bandwidth, OD 6) is used to block light emitted by the excitation light source 450 that is over 800 nm. The compact digital projector (Barco F50), which is used in some embodiments as the light emitting module 310 provides fast structured illumination at 120 Hz of the target object 324 for topography scanning. In other embodiments, the emission filter 340 may comprise a 700 nm low-pass filter (#84-727, Edmund Optics, OD 4), which removes any NIR (near infrared) light component that may interfere with fluorescence emission detection. Alternatively, the emission filter 340 may comprise a band-pass filter instead of the low-pass filter, so as to create a narrow band structured light illumination by use of the light emitter module 310.

The polarizer 830 and the analyzer 840 used by the embodiments of the present invention may be used together as a pair to remove photons that are diffused into the biological tissues of the target object 324 being imaged, leaving only photons reflected off of the surface of the target object 324, so as to ensure accurate surface topography acquisition of the target object 324. The structured light illumination of the target object 324 utilized by the present invention is more advantageous than traditional laser point scanning technologies, as the present invention is capable of operating at a much faster speed and does not have any moving parts.

The control module or controller 130 utilized by the embodiments of the present invention is configured to communicate with the various components of the configurations to enable their synchronized operation. In one aspect, the controller 130 may comprise a compact digital processing unit that comprises a FPGA (field programmable gate array) with a suitable computing unit, such as a laptop computer. The FPGA may be programmed using any suitable programming language and utilizes the parallel processing capabilities of the FPGA to implement real-time imaging and displaying of the results on a computer monitor, or any other suitable display. The FPGA board receives data from the image detection module 310 and the fluorescence imaging module 510, which is transmitted via any suitable data connection, such as a camera-link data bus or USB for example, to any suitable remote computing device. The laptop computer will receive the image information from the FPGA board for storage, processing and display purposes, and operates to directly control the structured light illumination from the digital projector provided by the light emitter 310 and excitation light source 450. It should be appreciated that other embedded systems, such as an embedded computer using ARM architecture and using a Linux operating system may be used instead of the FPGA as the controller 130. It should be further appreciated that the controller 130 may comprise any suitable computing system, such as a standalone or portable computing system.

Gesture Recognition

Because the system 100 has the capacity to perform 3D scanning and depth sensing, a depth map of what is being seen through the system 100 can be generated, whereupon this depth data can be used for detection of postures or gestures such as hand gestures. 3D model-based algorithms, skeletal-based algorithms, or appearance-based models may be used in the gesture recognition algorithm. For example, the gesture recognition may assist the user in controlling the system 100.

Cardiac Gating

Cardiac gating may be performed, where the electrocardiogram (ECG) signal may be acquired and used as a reference signal to correlate with the imaging data acquired by the system 100. As such, the data may be assigned to the different phases of respiratory cycles, so that the motion artifact can be reduced and the physiology of each cycle can be studied. I n one aspect, pulsed oximetry sensor or mechanical force sensors (placed on patient's thoracic cavity) may also be used to generate the gate signal.

Projecting Fluorescence Information onto Tissue Surface of Target Object

Furthermore, the various embodiments of the present invention have overcome several drawbacks of typical planar displays, which have been used in the past to display fluorescence information. For example, such planar displays typically utilized to present fluorescence imaging, may disturb or distract a surgeon or other individual, and in some cases affect his or her coordination, as they must continuously glance between the display and the subject being operated on. Furthermore, typical planar displays, such as a planar projector display, does not resolve depth/topography information, which can lead to erroneous projections of fluorescence information. Additionally, such planar displays make it difficult for the surgeon to track tissue deformation of the target object 324, as he or she is operating.

Figure 11:
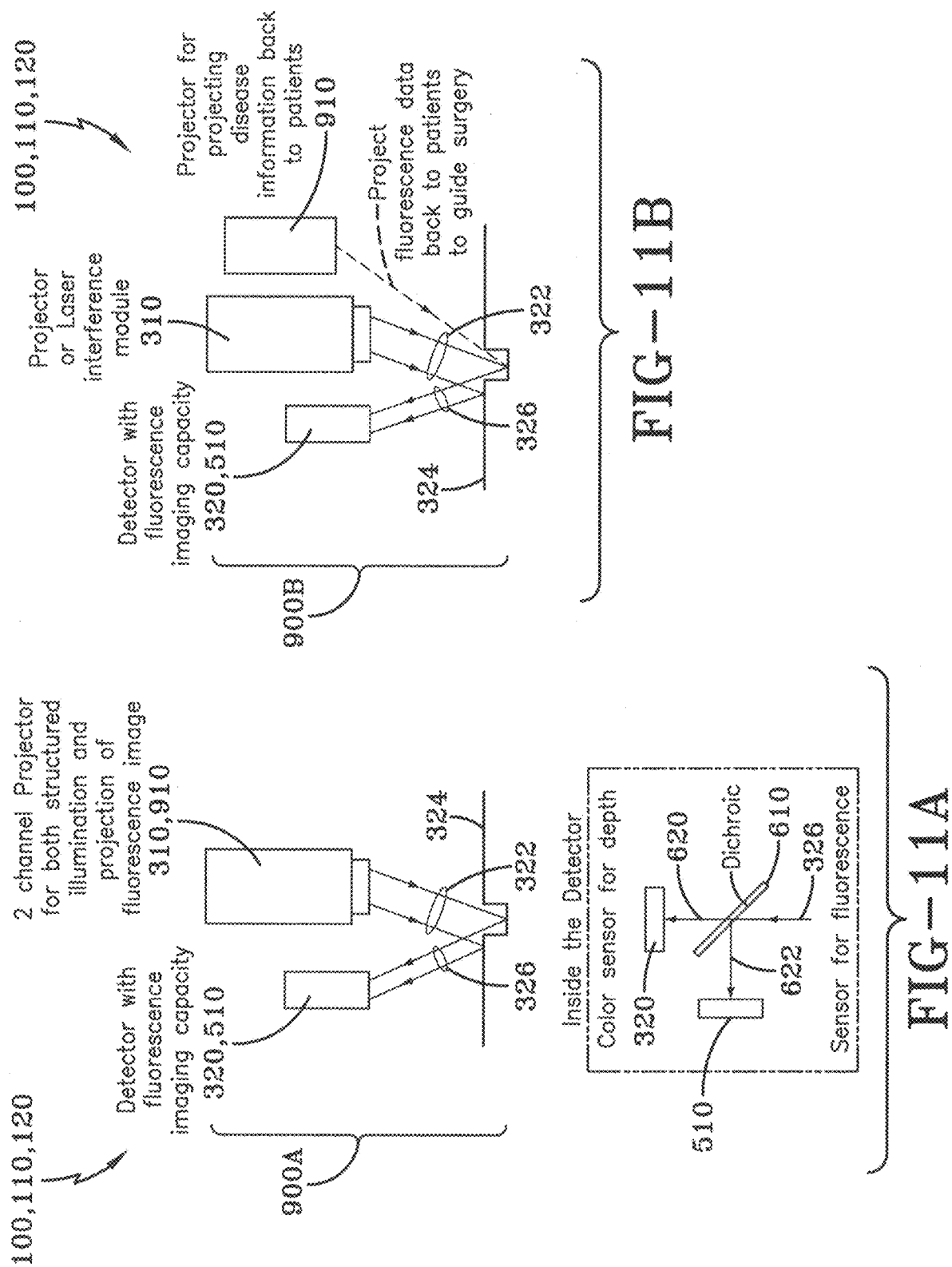
FIG. 11A is a block diagram of one configuration of the optical imaging system in accordance with the concepts of the present invention.
FIG. 11B is a block diagram of another configuration of the optical imaging system in accordance with the concepts of the present invention.

Accordingly, to overcome the drawbacks of current planar displays, which have been used to present fluorescence imaging information, another embodiment of the present invention 100, configuration 900A, may be utilized, as shown in FIG. 11A. Specifically, the configuration 900A includes an image projection system 910 that is incorporated into the imaging system 100, as shown in FIG. 11. In particular, the image detection sensor 310, the fluorescence detection sensor 510, the projection system 910, and the image detection module 310 are coupled to the controller 130. Additionally, the beam splitter 610 may be used, as shown in FIG. 11A, to allow the fluorescence imaging module 510 and the image detection module 310 to detect topography information and fluorescence information in response to being illuminated by the light emitter module 310, as previously discussed. As such, during operation of the configuration 900A, the light emitter module 310 generates light 322 to illuminate the target object 324. In addition, the fluorescence detection module 510 receives the reflected light 326 in response to being illuminated and processes it as fluorescence information. In addition, the image detection module 320 receives the emitted light 326 from the target object 324 in response to being illuminated and processes it as topography information. Next, after the system processes the detected fluorescence information according to the topography/depth information identified from the target object 324, the projection system 910 projects the fluorescence information back onto the target object 324, such as the patient. It should be appreciated that the projection system 910 and the light emitter module 310 can either be two separate devices, or may comprise one device performing both roles. In one aspect, one projector can serve as both the projection system 910 and the light emitter module 310, using the interleaving method previously described. As such, 2 channels may be created, with one for topography scanning and the other one for projection of image information back onto the surface of the object 324. It should be further appreciated that, using the interleaving method previously described, it is possible for the projector 910 to also create fluorescence excitation of the target object 324. Thus, this feature of the present invention provides the advantageous benefits of simultaneously providing both topography and fluorescence information to the surgeon. In addition, the present invention utilizes the topography information of the patient or target object 324 to enable the projection of the fluorescence information back onto the patient or target object with reduced latencies in space misalignment. The configuration 900A takes the depth profile and 3D shape of the target object 324 into account, and using projection mapping techniques based on the topography data of the target object 324 calculates and processes the appropriate projection images for the projector 910. Furthermore, the present invention uses a 3D surface profile to track tissue movements of the target object 324 during an operating procedure to reduce motion artifacts in the projected fluorescence image.

It should also be appreciated that in additional embodiments, the projection system 910 may be provided in an imaging configuration 900B, as a separate component apart from the light emitter module 310, as shown in FIG. 11B. As such, the topography information and fluorescence information captured by the image detection module 310 and the fluorescence detection module 510 of the configuration 900B are transmitted to the projector system 900, which projects the fluorescence data back to the target object 324 to guide surgery.

In particular, the projection system 910, as shown in FIGS. 11A-B, may be used with any of the embodiments of the present invention. In particular, the projection system 910 is capable of receiving image data from multiple data input channels, including the image detection module 320, the fluorescence detection module 510, and any other image data source or peripheral, such as a data source containing preoperative CT/PET image data, MRI data, SPECT data or ultrasound data. Once the multiple data inputs have been received, the projection system 910 simultaneously projects the image data from the multiple data input channels back onto the target object 324. For example, one data input channel may contain fluorescence information, another data input channel may contain color reflectance data, and another data input channel may contain preoperative CT/PET data. In one embodiment, the projection system 910 may include a 2-channel projector that is capable of both structured illumination of the target object 324 and the projection of fluorescence images back onto the target object 324, as in FIG. 11A. In one aspect, the image projection and structured illumination processes may be interleaved to use alternating frames (e.g. 1st, $3^{rd}$, $5^{th}$ . . . frames for image projection, and 2nd, 4th, 6th . . . frames for structured illumination).

Thus, topography information is used to calculate the manner in which the fluorescence information or other image data is projected back to the patient or target object 324 by the projection system 910. For example, the projection system 910 of the present invention can project topography-correlated fluorescence information back to the patient or target object 324, or can project topography-corrected fluorescence and PET/CT information back to the patient or target object 324 to guide surgery. It should also be appreciated that any other type of image data, including but not limited to MRI (magnetic resonance imaging) data, ultrasound image data, gamma imaging data, CT imaging data, and X-ray imaging data, may be delivered to the input channels of the projection system 910, for projection onto the patient or target object 324 based on the topography data captured and projection mapping methods.

Figure 3:
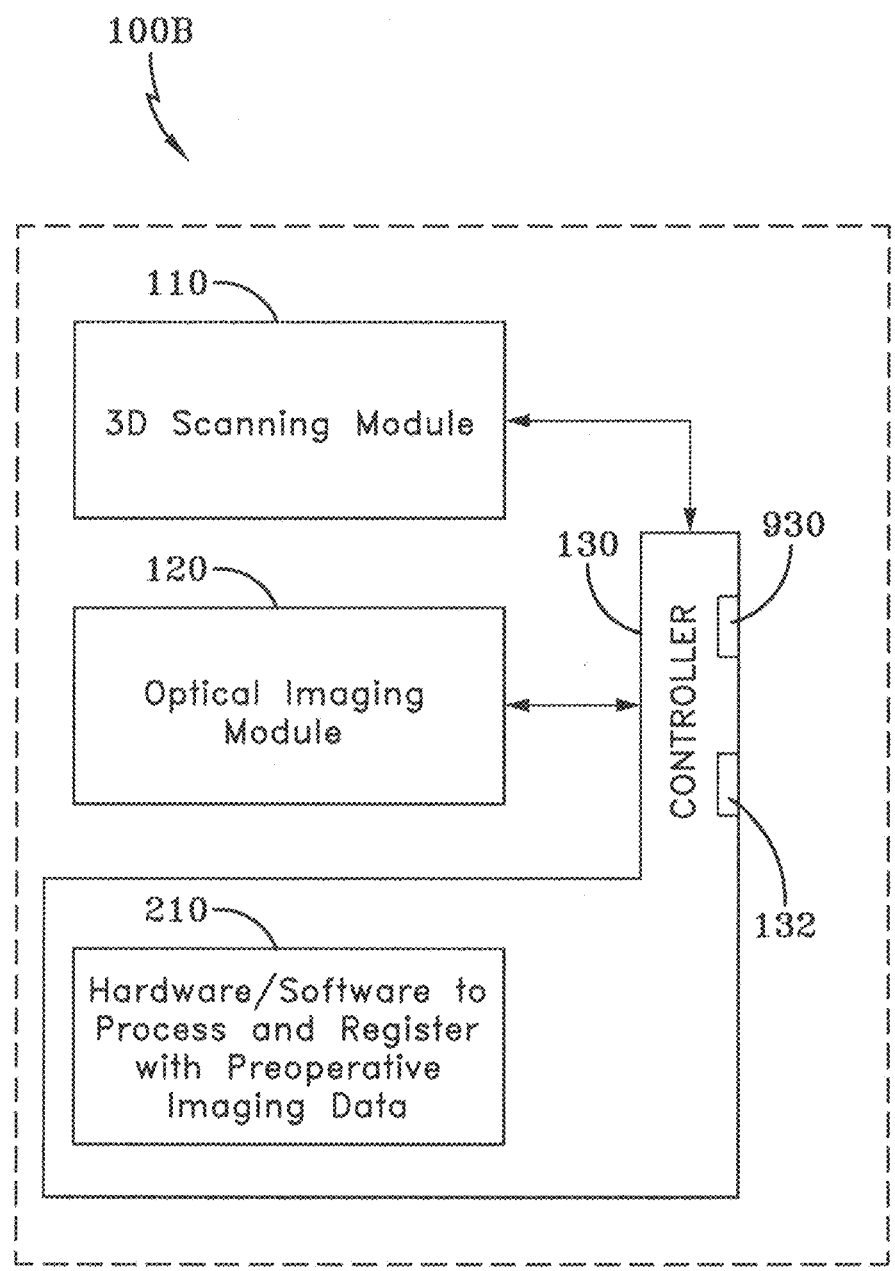
FIG. 3 is a block diagram of an alternative optical imaging system in accordance with the concepts of the present invention.

In another aspect, the present invention may include a peripheral interface 930 provided by the controller 130, as shown in FIGS. 1-3, which may comprise a wired or wireless interface, which allows the addition of one or more peripherals to be selectively incorporated, attached, or otherwise placed into communication with the imaging and detection system 100. For example, the peripherals may include, but are not limited to, one or more sensors and detectors, including a vital sign sensor module, which is configured to monitor various attributes of a patient, including but not limited to temperature, blood pressure, pulse, respiratory rate, ECG, EEG, pulse oximetry, and blood glucose. The peripherals may also include, but are not limited to an ultrasound module, a spectroscopy module (e.g. Raman spectroscopy, absorption spectroscopy, and reflectance spectroscopy), a GPS (global positioning system) module, a microscope module (e.g. a handheld microscope, a fiber-based in-vivo microscope, and a traditional microscope), and a non-microscopic imaging module (hyperspectral imaging, photoacoustic imaging, optical coherence imaging).

In still another aspect, the peripheral may comprise a probe-based instrument, such as a hand-held probe used to acquire or sense any in-vivo target of interest. As such, the hand-held probe may be used for any desired type of microscopy, such as in-vivo microscopy. Furthermore, the peripheral probe may utilize any suitable detection method, including but not limited to color microscopy, reflectance microscopy, fluorescence microscopy, oxygen-saturation microscopy, polarization microscopy, infrared microscopy, interference microscopy phase contrast microscopy, differential interference contrast microscopy, hyperspectral microscopy, total internal reflection fluorescence microscopy, confocal microscopy, non-linear microscopy, 2-photon microscopy, second-harmonic generation microscopy, super-resolution microscopy, photoacoustic microscopy, structured light microscopy, 4Pi microscopy, stimulated emission depletion microscopy, stochastic optical reconstruction microscopy, ultrasound microscopy, and combinations thereof.

In another aspect, the handheld probe comprising the peripheral may comprise an imaging device that does not have microscopic resolution. Thus, in some embodiments, the non-microscopic imaging probe peripheral of the present invention may utilize various imaging techniques, including but not limited to reflectance imaging, fluorescence imaging, Cerenkov imaging, polarization imaging, ultrasound imaging, radiometric imaging, oxygen saturation imaging, optical coherence tomography, infrared imaging, thermal imaging, photoacoustic imaging, spectroscopic imaging, hyper-spectral imaging, fluoroscopy, gamma imaging, and X-ray computed tomography. The physical form of the handheld probe peripheral may comprise an endoscope, a laparoscope, a bronchoscope, and angioscope, and a catheter for angiography.

Furthermore, the handheld probe may be a non-imaging device or a sensing device, such as a fiber-based spectrophotometer. In addition, different spectroscopies may be realized by the peripherals, such as various optical spectroscopies, absorption spectroscopy, fluorescence spectroscopy, Raman spectroscopy, coherent anti-Stokes Raman spectroscopy (CARS), surface-enhanced Raman spectroscopy, Fourier transform spectroscopy, Fourier transform infrared spectroscopy (FTIR), multiplex or frequency-modulated spectroscopy, X-ray spectroscopy, attenuated total reflectance spectroscopy, electron paramagnetic spectroscopy, electron spectroscopy, gamma-ray spectroscopy, acoustic resonance spectroscopy, auger spectroscopy, cavity ring down spectroscopy, circular dichroism spectroscopy, cold vapour atomic fluorescence spectroscopy, correlation spectroscopy, deep-level transient spectroscopy, dual polarization interferometry, EPR spectroscopy, force spectroscopy, Hadron spectroscopy, Baryon spectroscopy, meson spectroscopy, inelastic electron tunneling spectroscopy (IETS), laser-induced breakdown spectroscopy (LIBS), mass spectroscopy, Mossbauer spectroscopy, neutron spin echo spectroscopy, photoacoustic spectroscopy, photoemission spectroscopy, photothermal spectroscopy, pump-probe spectroscopy, Raman optical activity spectroscopy, saturated spectroscopy, scanning tunneling spectroscopy, spectrophotometery, ultraviolet photoelectron spectroscopy (UPS), video spectroscopy, vibrational circular dichroism spectroscopy, X-ray photoelectron spectroscopy (XPS), and combinations thereof.

Algorithms for Co-Registration of Optical Data, and Other Image Data (PET/CT and MRI Data)

Figure 12:
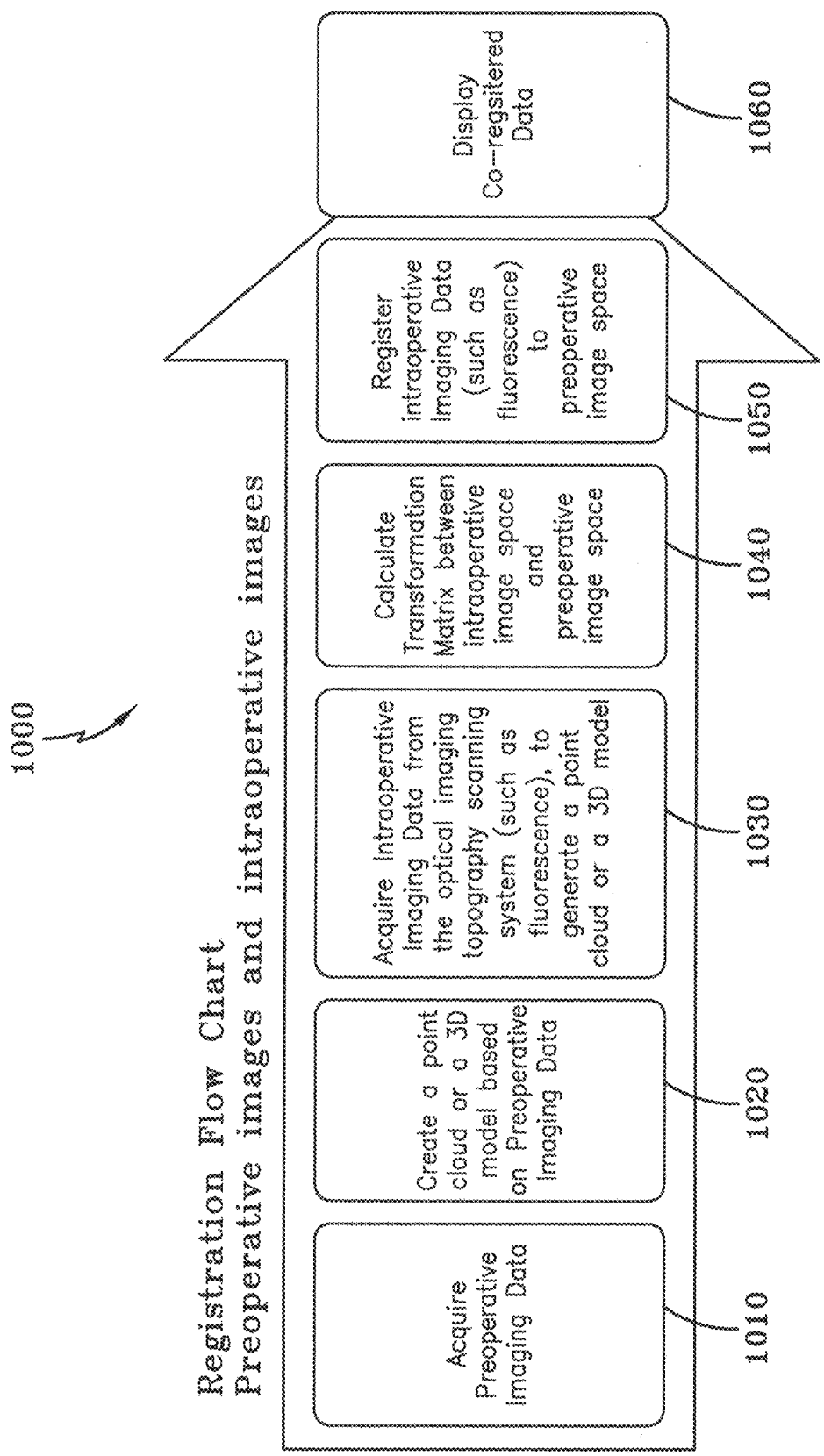
FIG. 12 is a flow diagram showing the steps taken by the optical imaging system to co-register images in accordance with the concepts of the present invention.

A process 1000 executed by the controller 130 for co-registration of the intraoperative optical data captured by the imaging system 100 of the present invention with other image data is shown in FIG. 12. In one embodiment of the present invention, data from a preoperative PET/CT scan may be acquired prior to performing intraoperative imaging using the system 100 of the present invention. Surface-based registration will be carried out using an iterative closest point algorithm, with the use of k-d dimensional trees to minimize processing time, in accordance with the process discussed in detail below. Initially, at step 1010, the controller 130 acquires preoperative imaging data, such as PET/CT image data. Next, at step 1020, the process creates a point cloud or 3D mesh model, which is based on the preoperative imaging data. In addition, intraoperative imaging data is acquired from the optical imaging topography scanning system 100 of the present invention, such as fluorescence imaging data, in order to generate a point cloud or 3D model, as indicated at step 1030. Continuing, at step 1040, the process 1000 calculates a transformation matrix between the intraoperative image space and the preoperative image space. Next, at step 1050 the intraoperative imaging data, such as fluorescence image data and color reflectance data, is registered to the preoperative image space. Finally, at step 1060, the co-registered image data is displayed via the projection system 910 onto the patient or target object 324, as previously discussed, or onto any suitable display, such as an LCD (liquid crystal display).

Thus, the process 1000 provides that the image registration may be either surface based or point based. In addition, the image registration can be based on point clouds or on the surface models that are rendered from the image data, or combinations thereof. Optionally, the registration process may utilize finite element modeling or biomechanical modeling algorithms to compensate for movement and deformation of the surgical site. It should also be appreciated that the 3D topography data may be represented using point clouds, or polygon meshes. Furthermore, the registration may be performed with point cloud representation, or polygon mesh representation, or combinations thereof.

It should also be appreciated that in addition to the registration techniques discussed above, other registration techniques may be used by the present invention, such as point-based registration, surface-based registration, and combinations thereof. The registration may comprise either intensity-based or feature-based registration. The transformation models used may comprise linear transformation, or non-rigid/elastic transformation. Spatial or frequency domain methods may be used, as well as automatic or interactive methods. In addition, machine learning algorithms may be used to facilitate image registration. For example, the machine learning algorithm may include, but is not limited to decision tree learning, association rule learning, artificial neural networks, inductive logic programming, support vector machines, clustering, Bayesian networks, reinforcement learning, representation learning, similarity and metric learning, sparse dictionary learning, genetic algorithms, deep learning, and combinations thereof.

It should also be appreciated that in addition to the techniques described above, other tracking techniques may be used, such as optical tracking, magnetic tracking, radio frequency tracking, gyroscope tracking, video tracking (pattern recognition), acoustic tracking, mechanical tracking, and combinations thereof. In addition, the tracking methods utilized by the present invention may utilize a rigid body, flexible body or digitizer methods. Furthermore, the tracking technique may be used either independently or in conjunction with registration algorithms, such as surface-based registration. It should also be appreciated that the previously discussed peripheral modules may be tracked using the tracking techniques for registration with preoperative imaging data and intraoperative imaging data. For example, an ultrasound probe may be optically tracked to document its spatial locations.

Figure 13A:
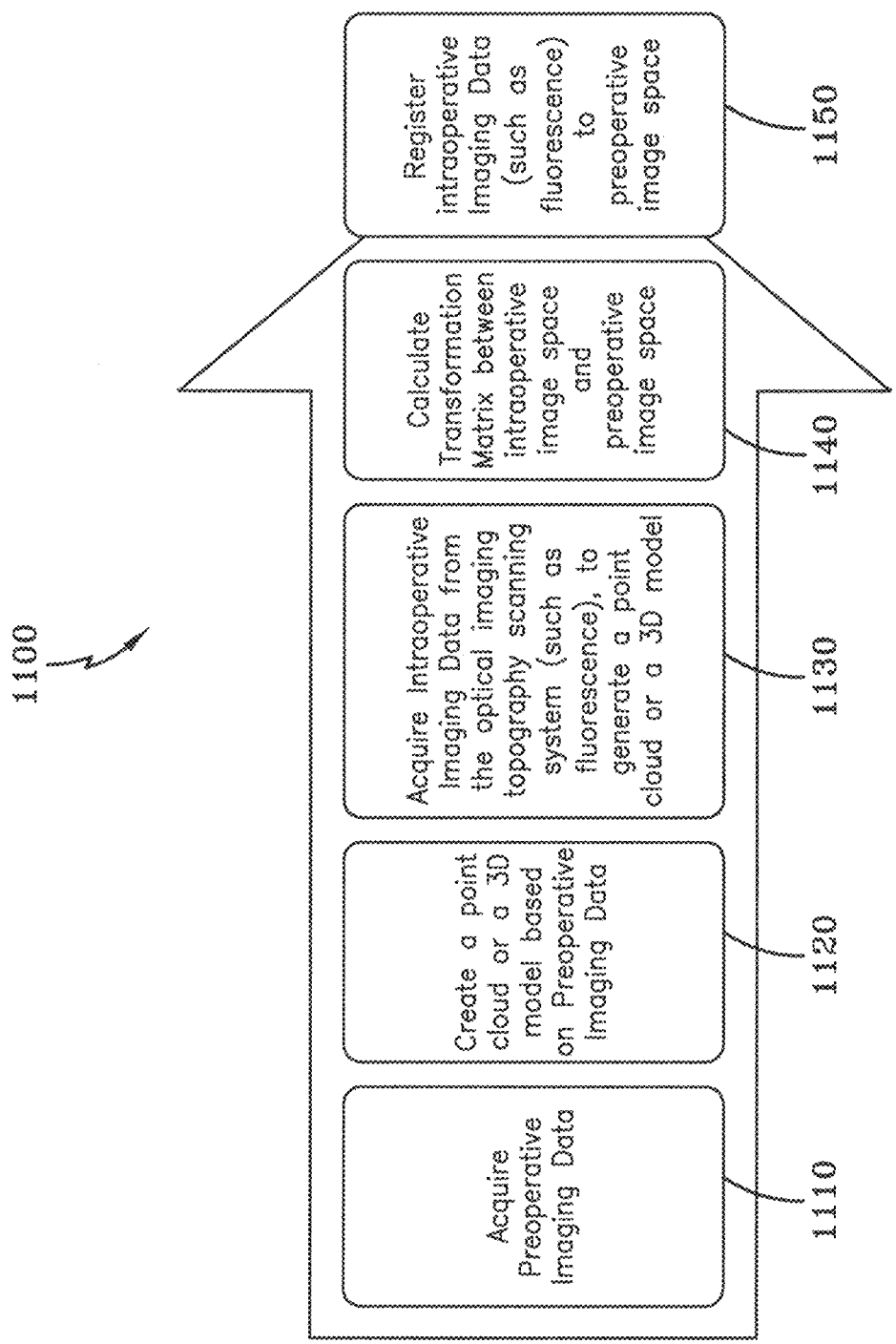
FIGS. 13A-B is an alternative flow diagram showing the steps taken by the optical imaging system to co-register images in accordance with the concepts of the present invention.
Figure 13B:
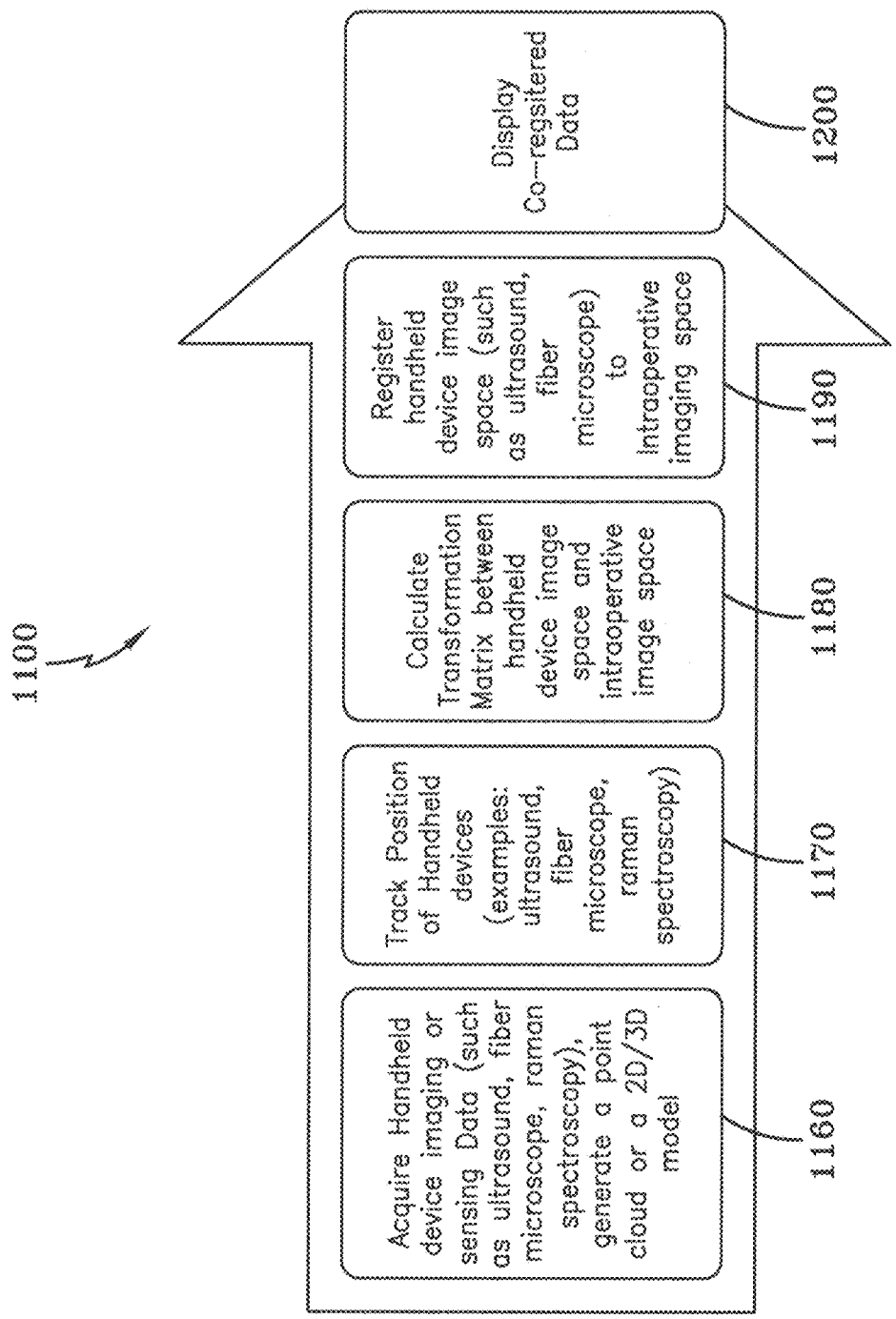

If the peripheral placed in communication with the peripheral interface 930, such as ultrasound or handheld microscope, is used an alternative registration process 1100 is executed by the controller 130, as shown in FIGS. 13A-B. Initially, at step 1110 of the process 1100, preoperative imaging data is acquired by the peripheral interface 930 of the control system 130. Next, a point cloud or 3D model that is based on preoperative imaging data is created, as indicated at step 1120. The process 1100 then acquires, at step 1130, intraoperative imaging data from the optical imaging system 100, such as fluorescence information, to generate a point cloud or 3D model. At step 1140, the process 1100 calculates a transformation matrix between the intraoperative image space and the preoperative image space. Next, the intraoperative imaging data, such as fluorescence image data, is registered to the preoperative image space, as indicated at step 1150. Continuing to step 1160, a moveable peripheral device, such as a hand-held imaging device, or sensing data is acquired, such as ultrasound, fiber microscope, and Raman spectroscopy to generate a point cloud, a polygon mesh or 2D/3D model. Next, at step 1170, the position of the hand-held imaging device is tracked using tracking technologies such as optical tracking, while a transformation matrix between the hand-held device image space and intraoperative image space is calculated at step 1180. Next, the hand-held image space, such as the ultrasound fiber microscope, is registered to the intraoperative imaging space, as indicated at step 1190. Finally, at step 1200 the co-registered data of step 1190 is displayed by the projection system 910 onto the patient or target object 324, as previously discussed, or may be displayed on any other display unit.

Fluorescence Imaging with Laser Triangulation for Topography Scanning

In another embodiment, the present invention may utilize a triangulation based method to perform topography scanning of the target object 324, whereby laser light is used to probe the depth information for topography. As such, a triangulation laser emits a laser spot on the target object 324 and a camera or imaging sensor is used to search for the location of the laser dot. Depending on the depth in which the laser strikes a given target object 324, the laser dot appears at a different place in the depth of the field of view of the camera or imaging sensor. Therefore, the depth information of the target object 324 can be inferred. Raster scanning the laser dot will generate a point cloud with depth information on the target object 324. Optionally, a laser stripe may be used instead of a single laser dot, whereupon the laser stripe is swept across the target object 324 to speed up the topography scanning process.

Thus, to carry out the triangulation topography scanning process, the imaging system 100 may be embodied as another configuration 1300A, as shown in FIG. 14A may be used. Specifically, the configuration 1300A includes the image detection module 320, which may comprise a CCD (charge-coupled device) or CMOS (complementary metal oxide) camera or other imaging sensors. In addition, the configuration 1300A includes the light emitter module 310, which is configured to emit one or more laser beams, which are used to illuminate the target object 324. It should be appreciated the light emitter module 310 may also be configured to emit laser beams of one or more center wavelengths, so that one wavelength is used for 3D scanning and another wavelength is used for fluorescence imaging. In addition, the image detection module 320 includes the emission filter 340, which is configured as a moveable filter wheel, as previously discussed. As such, to capture fluorescence information of the target object 324, the target object 324 is illuminated by the laser beam 322 emitted by the light emitter module 310. In addition, the filter wheel is moved so that the emission filter 340 processes the light 326 emitted by the target object 324 in response to being illuminated by the laser beam 322 of the light emitter module 310, whereupon the processed light detected by the image detection module 320 comprises fluorescence information of the target object 324. In another mode of operation to capture topography information, the light emitter module 310 emits one or more laser beams 322, which are used to illuminate the target object 324. In addition, the filter wheel is moved so that the emission filter 340 does not process the light 326 reflected by the target object 324 in response to being illuminated by the laser beam 322 of the light emitter module 310, whereupon the processed light detected by the image detection module 320 comprises topography information of the target object 324.

In a further embodiment, the alternative imaging system 100, may be embodied in an imaging configuration 1300B, as shown in FIG. 14B. Specifically, the imaging configuration 1300B includes the image detection module 320, which may comprise a CCD (charge-coupled device) or CMOS (complementary metal oxide) camera or imaging sensor, the light emitter module 310, which is configured to emit one or more laser beams used to illuminate the target object 324, and the emission filter 340, as previously discussed with regard to FIG. 14A, with the addition of the fluorescence imaging module 510. The fluorescence imaging module 510 is configured for use in conjunction with the emission filter 340. As such, to capture fluorescence information of the target object 324, the target object 324 is illuminated by the laser beam 322 emitted by the light emitter module 310. In response to being illuminated by the laser beam 322 of the light emitter module 310, the target object 324 emits light 326 that is processed by the emission filter 340 before being detected by the fluorescence imaging module 510 as fluorescence information of the target object 324. In another mode of operation to capture topography information, the light emitter module 310 emits one or more laser beams 322, which are used to illuminate the target object 324, whereupon the light 326 reflected from the target object 324 is detected by the image detection module 320 as topography information of the target object 324. It should be appreciated the light emitter module 310 may be configured to emit laser beams of one or more center wavelengths, so that one wavelength is used for 3D scanning and another wavelength is used for fluorescence imaging.

It should also be appreciated that in various embodiment, a fluorescence light source may be used. Furthermore, in various embodiments, laser diodes or a laser can be used for triangulation purposes. In other embodiments, multiple channels of fluorescence can be acquired, as well as color reflectance information can be acquired.

In further embodiments, the 3D scanning module 110 and the imaging module 120 may be embodied in an imaging configuration 1350A, as shown in FIG. 15A. Specifically, the imaging configuration 1350A includes, the image detection module 320, the emission filter 340, the image detection module 320A and the emission filter 340A, and the excitation light source 450 which operates in conjunction with the fluorescence excitation filter 410, as previously discussed with regard to FIG. 4F, with the addition of the light emitter module 310 being configured as a triangulation laser. Specifically, the triangulation laser 310 is configured to emit a plurality of laser beams 322 suitable for carrying out a triangulation process of the target object 324. It should be appreciated that the emission filters 340 and 340A are configured as filter wheels, which may be moved into and out of the optical detection path of the respective imaging detection modules 320 and 320A. As such, during operation of the detection configuration 1350A, the image detection modules 320 and 320A capture topography information of the target object 324 when the light emitter 310 is used to emit laser beams 322 to illuminate the target object 324, and the emission filters 340 and 340A are moved out of the detection path of the respective image detection modules 320 and 320A to detect the reflected light 326 from the target object 324. In another aspect, the 3D scanning process may be optionally performed without having the emission filter 340 and 340A moved out of the detection path of the image detection modules 320 and 320A. For example, the light emitter module 310 may be configured to emit light that is able to pass through the emission filters 340 and 340A to enable 3D scanning. One example of this process is that the light emitter module 310 may emit light at a wavelength of about 830 nm, which is able to pass through the band-pass emission filters 340 and 340A that are centered at 830 nm, so that 3D scanning is able to be performed. Alternatively, to capture fluorescence information of the target object 324, the light source 450 is used to emit light 322, which is processed by the fluorescence excitation filter 410 that illuminates the target object 324, and the emission filters 340 and 340A are moved into the detection path of the respective image detection modules 320 and 320A to detect the emitted light 326 from the target object 324. It should also be appreciated that 3D scanning and fluorescence imaging may also be performed concurrently, or sequentially.

In yet another embodiment, the emission filters 340 and 340A may comprise tunable filters. The use of the tunable filters allows hyperspectral imaging to be performed by the configuration 1350A to capture multiple light wavelengths. In yet another embodiment, the emission filters 340 and 340A may comprise a filter wheel that includes a plurality of narrow-band filters. As such, the configuration 1350A is able to capture multiple light wavelengths of reflectance images or absorption images.

In yet another embodiment, the filter wheel embodying the emission filters 340 and 340A may include filters that are suitable for imaging oxygen saturation. For example, images of tissue oxygen saturation (STO2) or venous oxygen saturation (SVO2) may be measured. For example, 660 nm and 950 nm filters may be used to capture an oxygen saturation image. The oxygen saturation may be calculated using the equation: StO2=value of oxygen-saturated hemoglobin/total hemoglobin value (unsaturated+saturated). It should also be appreciated that Cerenkov imaging may also be enabled by using the appropriate filters 340 and 340A.

It should be appreciated that the different imaging modalities previously discussed may be obtained along with 3D scanning either sequentially or concurrently using the interleaved methods, previously described. It should be appreciated that a plurality of imaging modalities may be enabled by the present invention. For example, oxygen saturation imaging, color reflectance imaging, auto-fluorescence imaging and near infrared (NIR) imaging based on extrinsic contrast may be performed simultaneously at the same time. It should also be appreciated that filter 340A and 340 may have different configurations to enable different imaging modalities. For example, the filter 340 may be configured to capture fluorescence image and the filter 340A may be configured to capture multispectral reflectance images.

Furthermore, to perform the triangulation process, the laser module 310 emits a laser spot on the target object 324 and the detector 320 is used to search for the location of the laser dot on the target object 324. Depending on the depth in which the laser strikes the target object 324, the laser dot appears at a different place in the depth of the field of view of the camera or imaging sensor 320. Therefore, the depth information of the target object 324 can be inferred based on the corresponding pixel location on the sensor 320. Raster scanning the laser dot will generate a point cloud with depth information on the target object 324. Optionally, the light emitter module 310 can output a laser stripe instead of a single laser dot, whereupon the laser stripe is swept across the target object 324 to speed up the topography scanning process.

In a further embodiment, the 3D scanning module 110 and the imaging module 120 may be embodied in an imaging configuration 1350B, as shown in FIG. 15B. Specifically, the imaging configuration 1350B includes the image detection module 320, the image detection module 320A, the fluorescence imaging module 510, the emission filter 340, the light source 450 and the excitation filter 410, as previously discussed with regard to FIG. 5F, with the addition of the light emitter module 310 being configured as a triangulation laser. Specifically, the triangulation laser 310 is configured to emit a plurality of laser beams 322 suitable for carrying out a triangulation process of the target object 324. As such, during operation of the detection configuration 1350B, the light emitter module 310 emits laser beams 322 to illuminate the target object 324, whereupon the image detection modules 320 and 320A detect the reflected laser light 326 from the target object 324 as topography information. Alternatively, the fluorescence detection module 510 captures fluorescence information of the target object 324 when the excitation light source 450 that have been processed by the excitation filter 410 to illuminate the target object 324, whereupon the light 326 emitted by the target object 324 in response to being illuminated is processed by the emission filter 340 before being detected by the fluorescence detection module 510 as fluorescence information. It should be appreciated that the 3D scanning and fluorescence imaging processes may be performed concurrently, or sequentially.

Furthermore, to perform the triangulation process, the laser module 310 emits a laser spot on the target object 324, and the detector 320 is used to search for the location of the laser dot on the target object 324. Depending on the depth in which the laser strikes a given target object 324, the laser dot appears at a different place in the depth of the field of view of the camera or imaging sensor 320. Therefore, the depth information of the target object 324 can be inferred based on the corresponding pixel location on the sensor 320. Raster scanning the laser dot will generate a point cloud with depth information on the target object 324. Optionally, the light emitter module 310 may output a laser stripe instead of a single laser dot, whereupon the laser stripe is swept across the target object 324 to speed up the topography scanning process.

In further embodiments, the 3D scanning module 110 and the imaging module 120 may be embodied in an imaging configuration 1350C, as shown in FIG. 15C. Specifically, the imaging configuration 1350C includes the image detection module 320, the fluorescence imaging module 510, the emission filter 340, and the beam splitter 610, the excitation light source 450 and the excitation filter 410, as previously discussed with regard to FIG. 6C, with the addition of the light emitter module 310 being configured as a triangulation laser. Specifically, the triangulation laser 310 is configured to emit a plurality of laser beams 322 suitable for carrying out a triangulation process of the target object 324. In particular, the fluorescence excitation filter 410 is configured for use in conjunction with the excitation filter 410, and is operatively positioned so that the light 322 emitted from the light emitter module 310 passes therethrough before illuminating the target object 324 being imaged. As such, during operation of the detection configuration 1350C, the light emitter module 310 emits laser beams 322 to illuminate the target object 324, whereupon the light 326 reflected by the target object 324 in response to being illuminated is received by the beam splitter 610, where a portion 620 of the reflected light 326 is permitted to pass through the beam splitter 610 for receipt by the image detection module 320 to capture topography data of the target object 324. Alternatively, to detect fluorescence information from the target object 324, the excitation light source 450 is operated to generate light 322 that is processed by the excitation filter 410 to illuminate the target object 324. As such, the light 326 emitted from the target object 324 in response to being illuminated is received by the beam splitter 610. Next, the portion 622 of the light emitted light 326 is reflected by the beam splitter 610, whereupon it is directed to pass through the emission filter 340 for receipt by the fluorescence imaging module 510 to capture fluorescence information of the target object 324.

For triangulation, the laser module 310 emits a laser spot on the target object 324 and the detector 320 is used to search for the location of the laser dot on the target object 324. Depending on the depth in which the laser strikes a given target object 324, the laser dot appears at a different place in the depth of the field of view of the camera or imaging sensor 320. Therefore, the depth information of the target object 324 may be inferred based on the corresponding pixel location on the sensor. Raster scanning the laser dot will generate a point cloud with depth information on the target object 324. Optionally, the light emitter module 310 may output a laser stripe instead of a single laser dot, whereupon the laser stripe is swept across the target object 324 to speed up the topography scanning process.

In further embodiments, the 3D scanning module 110 and the imaging module 120 may be embodied in an imaging configuration 1350D, as shown in FIG. 15D. Specifically, the imaging configuration 1350D includes the image detection module 320, the fluorescence imaging module 510, the emission filter 340, the beam splitter 610A, the image detection module 320A, the fluorescence imaging module 510A and the emission filter 340A, as previously discussed with regard to FIG. 7A, with the addition of the light emitter module 310 being configured as a triangulation laser. Specifically, the triangulation laser 310 is configured to emit a plurality of laser beams 322 suitable for carrying out a triangulation process of the target object 324. As such, the image detection module 320 and the fluorescence imaging module 510 are positioned at a substantially right angle to each other, while the image detection module 320A and the fluorescence imaging module 510A are also positioned at a substantially right angle to each other. In addition, the beam splitter 620 is positioned at an oblique angle, such as about 45 degrees, relative to the image detection module 320 and the fluorescence imaging module 510. Similarly, the beam splitter 620A is positioned at an oblique angle, such as about 45 degrees, relative to the image detection module 320A and the fluorescence imaging module 510A. As such, during operation of the detection configuration 1350D, the light emitter module 310 emits laser beams 322 to illuminate the target object 324, whereupon the light 326 reflected and emitted by the target object 324 in response to being illuminated is received by the beam splitters 610 and 610A, where a portion 620 of the light 326, as light reflected by the target object 324, is permitted to pass through the beam splitters 610 and 610A for receipt by the image detection modules 320 and 320A to capture topography data of the target object 324. In addition, another portion 622 of the light 326, as light emitted by the target object 324, is received by the beam splitters 610 and 610A is reflected by the beam splitters 610 and 610A, whereupon it is directed to pass through the emission filters 340 and 340A for receipt by the fluorescence imaging modules 510 and 510A to capture fluorescence information of the target object 324.

Fluorescence Imaging with Time-of-Flight Scanner/Range Finder for Topography Scanning In other embodiments, a time-of-flight laser range finder, or Lidar, or laser scanner may be integrated or utilized in conjunction with the optical imaging capabilities of the present invention previously discussed. Various optical imaging modalities including but not limited to fluorescence, color reflectance, polarization, multispectral, hyperspectral, absorption and oxygen saturation can also be implemented. For example, in some embodiments, the time-of-flight laser range finder or scanner identifies the distance of the target object 324 by identifying the round-trip time that it takes for a pulse of light emitted by the range finder to reach the target object 324 and return back to the ranger finder. That is, a pulsed laser range finder emits a pulse of light and the amount of time before the light reflected by the target object 324 is captured by the detector is measured as the time-of-flight time.

In a further embodiment, the 3D scanning module 110 and the imaging module 120 may be embodied in an imaging configuration 1400A, as shown in FIG. 16A. Specifically, the imaging configuration 1400A includes the image detection module 320, the emission filter wheel 340, the excitation light source 450 and the fluorescence excitation filter 410 as previously discussed with regard to FIG. 4C, with the addition of the light emitter module 310 being configured as a ranger finder. Specifically, the light emitter module 310 may be configured as a time-of-flight laser range finder, or any other suitable range finder, such as a laser range finger. In one embodiment, the laser 310 is configured to emit a plurality of laser beams 322 suitable for carrying out a range-finder process to identify the distance to the target object 324. Additionally, the excitation light source 450 may be configured to generate any suitable light, which then passes through the excitation filter 410. In particular, the fluorescence excitation filter 410 is positioned so that the light 322 emitted from the excitation light source 450 passes therethrough before striking the target object 324 being imaged. As such, during operation of the detection configuration 1400A, the image detection module 320 captures topography information of the target object 324 when the emission filter 340 is moved out of the light 326 detection path of the image detection module 320 and the light emitter module 310 is used to generate laser beams 322 to illuminate the target object 324. In another aspect, the 3D scanning process may be optionally performed without having the emission filter 340 moved out of the detection path of the image detection module 320. For example, the light emitter module 310 may be configured to emit light that is able to pass through the emission filter 340 to enable 3D scanning. One example of this process is that the light emitter module 310 may emit light at a wavelength of about 830 nm, which is able to pass through the band-pass emission filters 340 that are centered at 830 nm, so that 3D scanning is enabled. Alternatively, the image detection module 320 captures fluorescence information from the target object 324 when the emission filter 340 is moved into the detection path of the image detection module 320, and the excitation filter 410 is moved to process the light 322 emitted from the light source 450 to illuminate the target object 324. As such, the light 326 emitted by the target object 324 in response to being illumined by the processed light 322 from the light source 450 is then processed by the emission filter 340 before being detected by the image detection module 320 as fluorescence information of the target object 324.

Figure 16B:
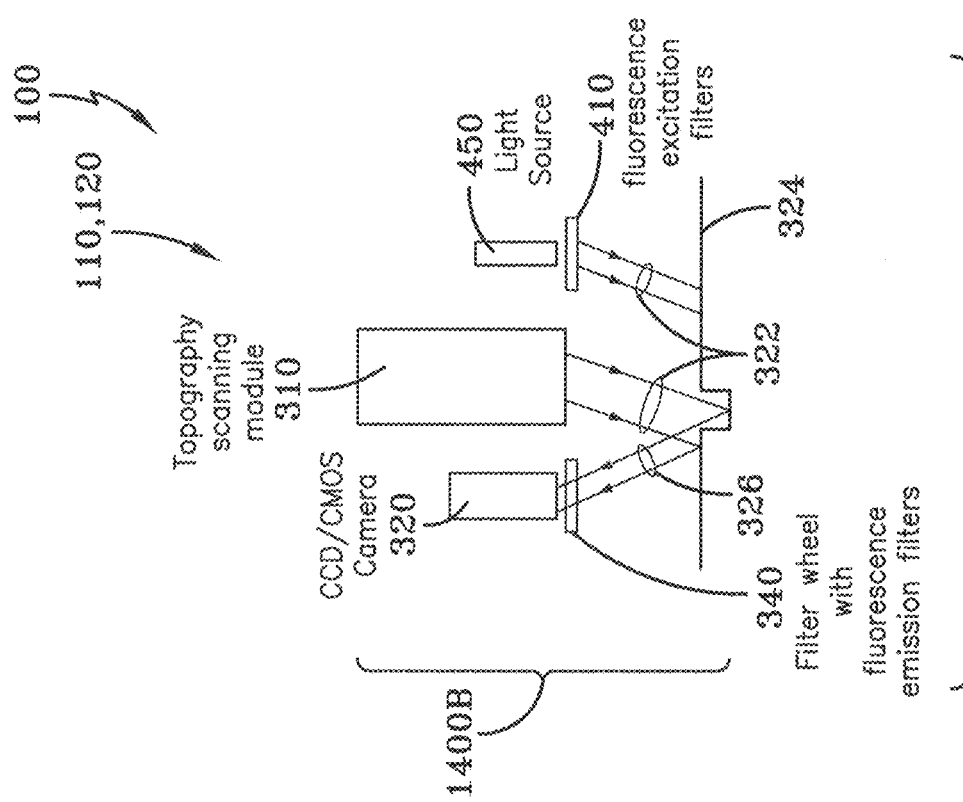
FIG. 16B is a block diagram of another configuration of the optical imaging system in accordance with the concepts of the present invention.

In a further embodiment, the 3D scanning module 110 and the imaging module 120 may be embodied in an imaging configuration 1400B, as shown in FIG. 16B. Specifically, the imaging configuration 1400B includes the image detection module 320, the emission filter wheel 340, the excitation light source 450 and the fluorescence excitation filter 410 as previously discussed with regard to FIG. 4C, with the addition of the light emitter module 310 being configured as a topography scanning module. Specifically, the topography scanning module forming the light emitter module 310 may be configured to utilize various topography scanning methods, including but not limited to conoscopic holography, modulated light, stereo camera, Fourier 3D scanning, low coherence interferometry, common-path interference 3D scanning, contact profilometers. The light emitter 310 may comprise the commercial depth sensing camera, such as the Microsoft Kinect™. In addition, such techniques can be integrated with advanced optical imaging methods, such as fluorescence imaging to produce both topography scanning and optical imaging data. It should also be appreciated that the excitation light source 450 may be configured to generate any suitable light, which then passes through the excitation filter 410. In particular, the fluorescence excitation filter 410 is positioned so that the light 322 emitted from the excitation light source 450 passes therethrough before striking the target object 324 being imaged. As such, during operation of the detection configuration 1400B, the image detection module 320 captures topography information of the target object 324 when the emission filter 340 is moved out of the light 326 detection path of the image detection module 320 and the light emitter module 310 is used to generate light beams 322 to illuminate the target object 324. In another aspect, the 3D scanning process may be optionally performed without having the emission filter 340 moved out of the detection path of the image detection module 320. For example, the light emitter module 310 may be configured to emit light that is able to pass through the emission filter 340 to enable 3D scanning. One example of this process is that the light emitter module 310 may emit light at a wavelength of about 830 nm, which is able to pass through the band-pass emission filters 340 that are centered at 830 nm, so that 3D scanning is enabled. Alternatively, the image detection module 320 captures fluorescence information from the target object 324 when the emission filter 340 is moved into the detection path of the image detection module 320, and the excitation filter 410 is moved to process the light 322 emitted from the light source 450 to illuminate the target object 324. As such, the light 326 emitted by the target object 324 in response to being illuminated by the processed light 322 from the light source 450 is then processed by the emission filter 340 before being detected by the image detection module 320 as fluorescence information of the target object 324.

In yet another embodiment, the emission filter 340 may comprise a tunable filter. The use of the tunable filter allows hyperspectral imaging to be performed by the configuration 1400B to capture multiple light wavelengths. In yet another embodiment, the emission filter 340 may comprise a filter wheel that includes a plurality of narrow-band filters. As such, the configuration 14006 is able to capture multiple light wavelengths of reflectance images or absorption images.

In yet another embodiment, the filter wheel embodying the emission filter 340 may comprise filters that are suitable for imaging oxygen saturation. For example, images of tissue oxygen saturation (STO2) or venous oxygen saturation (SVO2) may be measured. For example, 660 nm and 950 nm filters may be used to capture the oxygen saturation image. The oxygen saturation can be calculated using the equation: StO2=value of oxygen-saturated hemoglobin/total hemoglobin value (unsaturated+saturated). It should also be appreciated that Cerenkov imaging may also be enabled by using the appropriate filter 340.

It should also be appreciated that polarizers may be used instead of spectral filters, and also another polarizer may be placed in front of the light emitter module 310 to enable polarization imaging, and polarization difference/ratio imaging. It should be appreciated that the different imaging modalities previously discussed may be obtained, along with 3D scanning, either sequentially or concurrently using the interleaved methods, previously described. It should be appreciated that a plurality of imaging modalities may be enabled by the present invention. For example, oxygen saturation imaging, color reflectance imaging, auto-fluorescence imaging and near infrared (NIR) imaging based on extrinsic contrast may be enabled or performed simultaneously, at the same time, by the present invention.

Color-Encoded Stripe Indexing and Wavelength-Splitting Techniques

Figure 17:
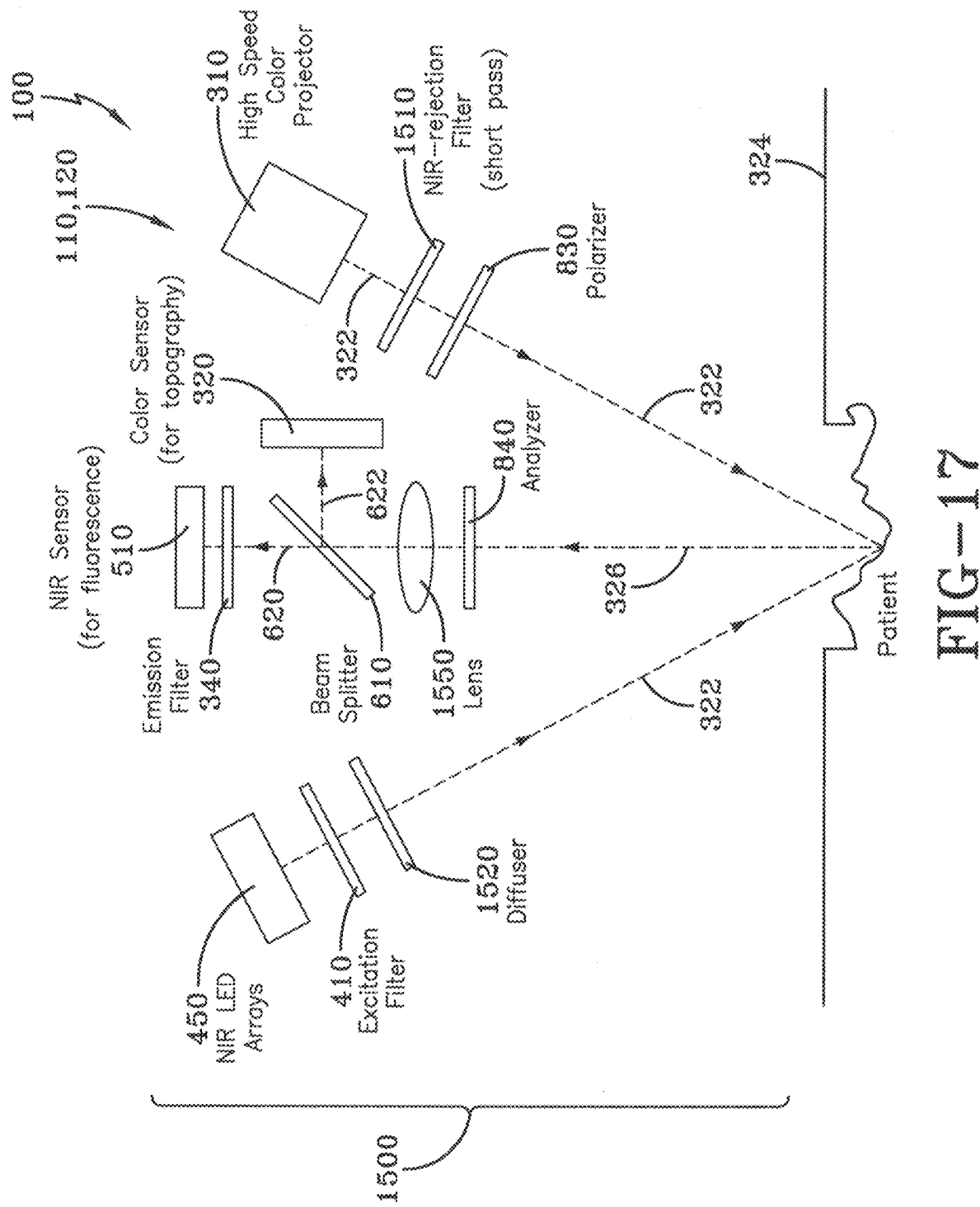
FIG. 17 is a block diagram of one configuration of the optical imaging system in accordance with the concepts of the present invention.

In further embodiments, the 3D scanning module 110 and the imaging module 120 may be embodied in an imaging configuration 1500, as shown in FIG. 17. Specifically, the imaging configuration 1500 includes the light emitter module 310, which is configured as a high-speed color projector. In operative arrangement with the light emitter module 310 is a near-infrared (NIR) rejection filter 1510 and the polarizer 830. It should be appreciated that in some embodiments the filter 1510 may comprise a short-pass filter. As such, during operation of the light emitter module 310, the light 322 emitted by the light emitter module 310 is processed by the NIR rejection filter 1510 and the polarizer 830, whereupon the processed light 322 illuminates the target object 324. The imaging configuration 1500 also includes the light source 450, which comprises a near-infrared LED (light emitting diode) array 450. The light source 450 is in operative arrangement with the excitation filter 410, and a light diffuser 1520. Furthermore, the image detector module 320, the light emitting module 310, the light source 450, and the fluorescence imaging module 510 are coupled to the controller 130 so that the components may communicate with each other using suitable communication techniques. As such, during operation of the light source 450, the light 322 emitted by the light source 450 is processed by the excitation filter 410 and the light diffuser 1520, whereupon the processed light 322 illuminates the target object 324. In addition, the imaging configuration 1500 includes the beam splitter 610, which may comprise a dichroic filter or any suitable device capable of reflecting light of one range of wavelengths, and passing light of another range of wavelengths. In addition, the imaging configuration 1500 includes the image detection module 320, the fluorescence imaging module 510, and the emission filter 340, such that the image detection module 320 is positioned at an angle, such as a substantially right angle, to the fluorescence imaging module 510 and emission filter 340. In addition, the beam splitter 610 is positioned at an oblique angle, such as about a 45 degree angle, relative to the image detection module 320 and the fluorescence imaging module 510/emission filter 340. It should be appreciated that the image detection module 320 is configured as a color sensor for capturing topography information of the target object 324, while the fluorescence imaging module 510 is configured as a near-infrared (NIR) sensor for capturing fluorescence information of the target object 324. In addition, an optical lens 1550 and the analyzer 840 are operatively arranged relative to the beam splitter 610, such that the optical lens 1550 is placed proximate to the beam splitter 610 and the analyzer 840 is placed distal to the beam splitter 610. In addition, the optical lens 1550 and the analyzer 840 are positioned parallel to the fluorescence imaging module 510 and at a substantially right angle to the image detection module 320, while the beam splitter 610 is positioned at an oblique angle, such as about a 45-degree angle, relative to the optical lens 1550 and the analyzer 840. Thus, light 326 that is reflected or emitted from the target object 324 in response to being illuminated by the light 322 emitted from the emitting module 310 or the light 322 emitted from the excitation light source 450 is processed by the analyzer 840 and the optical lens 1550 before being received by the beam splitter 610, whereupon the processed light 326 is directed to the image detection module 320 and the emission filter 340 and the fluorescence imaging module 510 in the manner to be discussed.

As such, during operation of the detection configuration 1500 to detect topography information of the target object 324, the light emitter module 310 emits light 322, which is processed by the NIR rejection filter 1510 and the polarizer 830 to illuminate the target object 324, whereupon the light 326 reflected by the target object 324 in response to being illuminated is received by the beam splitter 610. Upon receipt of the light 326 at the beam splitter 610, the beam splitter 610 reflects the light 326 as light rays 622 for receipt by the image detection module 320 to capture color topography data of the target object 324. In addition, to detect fluorescence information of the target object 324, the excitation light source 450 emits light 322, which is processed by the excitation filter 410 and the light diffuser 1520 to illuminate the target object 324, whereupon the light 326 that is emitted by the target object 324 in response to being illuminated is received by the beam splitter 610 for receipt by the beam splitter 610. Upon receipt of the light 326 at the beam splitter 610, the beam splitter 610 allows the emitted light 326 to pass through the emission filter 340 as light rays 620 for receipt by the fluorescence imaging module 510 as fluorescence information of the target object 324.

It should be appreciated that the configuration 1500 of the present invention overcomes the limitations of past generation imaging systems that have slow scanning speeds and reduced near-infrared (NIR) detection sensitivity. In particular, the configuration 1500 of the present invention, as shown in FIG. 17 uses a color-encoded stripe indexing single shot technique and a wavelength-splitting 2-sensor configuration that is based on high-speed CMOS imaging sensors 320 and 510. In particular, the image detector module 320, the light emitting module 310, the light source 450, and the fluorescence imaging module 510 and the controller 130 are coupled together so that the modules may communicate with each other using suitable communication techniques.

With regard to the image detection module 320 it may comprise a high-speed color CMOS sensor (LUPA 1300-2, ON Semiconductor) for real-time topography scanning. In some embodiments, the image detection module 320 may have a frame rate of about 500 frames per second.

In addition, the fluorescene imaging module 510 may comprise a NIR-sensitive CMOS sensor (MT9V032, Aptina), which may have a quantum efficiency of about 40% at about 800 nm. In addition, the emission filter 340 may comprise an 832 nm bandpass emission filter (#84-123, Edmund Optics) for fluorescence imaging with high sensitivity. In addition, the beam splitter 610 may comprise a short-pass dichroic beam splitter (FF756-SDi01-25x36, SEMROCK), which is used to separate the visible and NIR light components, as shown in the FIG. 17. The wavelength-splitting, 2-sensor configuration 1500 of the present invention enables the concurrent or simultaneous acquisition of topography and fluorescence information of the target object 324. The image detection module 320 comprising the color CMOS sensor may also be configured to capture reflectance images as needed. A F/4 imaging system may be implemented by the image detection module 320 and fluorescence imaging module 510 to achieve a large depth of field and high fluorescence collection efficiency.

The light source 450 may comprise a filtered NIR LED (light emitting diode) array and the light emitting module 310 may comprise a filtered high-speed color projector. The color projector (Barco F50) comprising the light emitting module 310 provides fast, single-shot, color-encoded, structured illumination at 120 Hz for real-time topography scanning of the target object 324. The color-encoded stripe indexing projection technique that is utilized by the configuration 1500 of the present invention is implemented using the techniques previously discussed. In addition, the NIR-rejection filter 1510 may comprise a 700 nm short-pass filter (#84-727, Edmund Optics) in order to remove any NIR component that hinders fluorescence detection. A polarizer/analyzer pair (#89-602, Edmund Optics) 830 and 840 are provided to remove photons diffused into the tissues or other material forming the target object 324 that are depolarized, and as such, operates to capture photons that are reflected off of the surface to ensure that an accurate topography acquisition of the target object 324 is performed. In addition, the light source 450 may comprise a 780 nm LED array (Roithner Lasertechnik LED 780-66-60), which has 60 LEDs and a 4 watt optical output power to provide uniform illumination over an area of about 30×24 cm at a 0.5 m working distance. In addition, in some embodiments only a defined field of interest, such as a surgical field, of the target object 324 will be illuminated to reduce the background. Additionally, the excitation filter 410 may comprise a 775 nm bandpass excitation filter (#840106, Edmund Optics) to block the emitted excitation light that is over 800 nm.

The controller 130 communicates with the image detector module 320, the light emitting module 310, the light source 450, and the fluorescence imaging module 510 to ensure their synchronized operation. In one aspect, the controller 130 may comprise a FPGA (field programmable gate array) with any suitable memory, such as a 1 GB external memory that is implemented on the board (Opakelly), together with any suitable computer system, such as a Dell precision Tower 7810 Workstation for control and image processing. The FPGA may be programmed using any suitable programming language, such as Verilog, and in some embodiments may utilize the parallel processing capabilities of the FPGA to implement real-time imaging. The FPGA is configured to receive data from the CMOS image sensors 320 and 510, which are transmitted via Camera-Link data buses. As such, the workstation forming the controller 130 receives the image from the FPGA board for storage, processing and display, and directly controls the structured light illumination from the digital projector.

Image Co-Registration Process

Figures 18G, 18H, 18I:
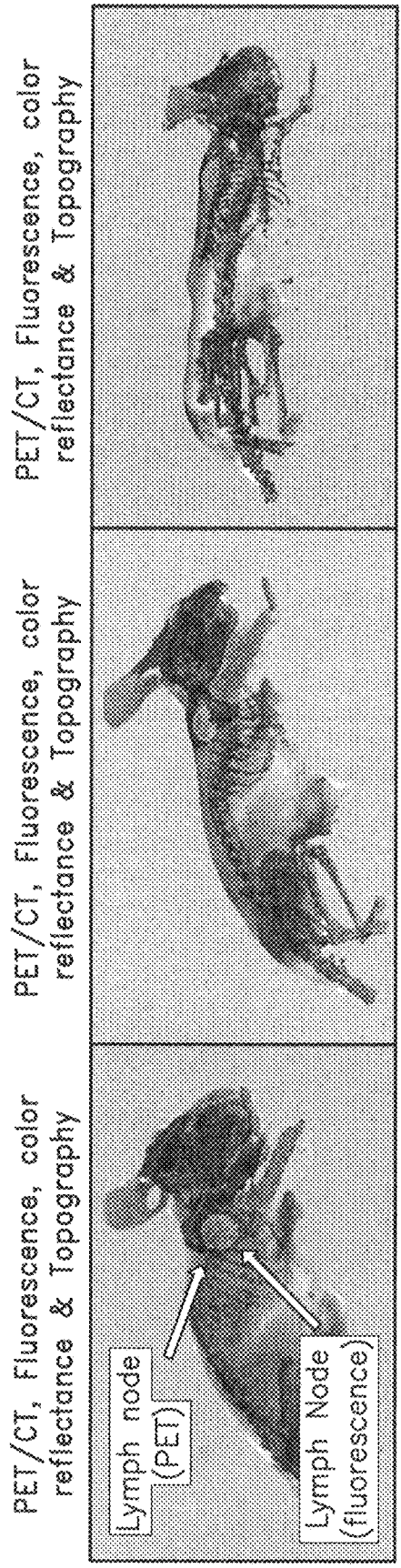

In addition, the present invention also provides a surface-based image co-registration algorithm for PET/CT (positron emission tomography) and/or CT (x-ray computerized tomography) with fluorescence imaging of the target object 324, as shown in FIG. 18. As such, the algorithm allows image data from individual modalities, as well as co-registered data to be displayed upon command based on user preferences. For example, preoperative PET/CT images, as shown in FIGS. 18D,E, and fluorescence imaging, as shown in FIGS. 18B,C of lymph nodes in mice have been captured. As such, the present invention uses the topography information, shown in FIG. 18A, of the target object 324 to allow accurate co-registration between intraoperative fluorescence imaging and color reflectance imaging, with preoperative PET/CT data, as shown in FIGS. 18F-I. As such, the present invention enables multimodal 3D (three-dimensional) image guidance to be provided that is based on preoperative PET/CT surgical navigation and intraoperative fluorescence imaging, as shown in FIGS. 18F-I. That is image data from individual modalities shown in FIGS. 18A-E and co-registered images of FIGS. 18C and 18F-I may be presented based on a user's preferences. The co-registered images of FIGS. 18G-I may be rotated to facilitate surgical planning and intraoperative decision making.

Figure 19:
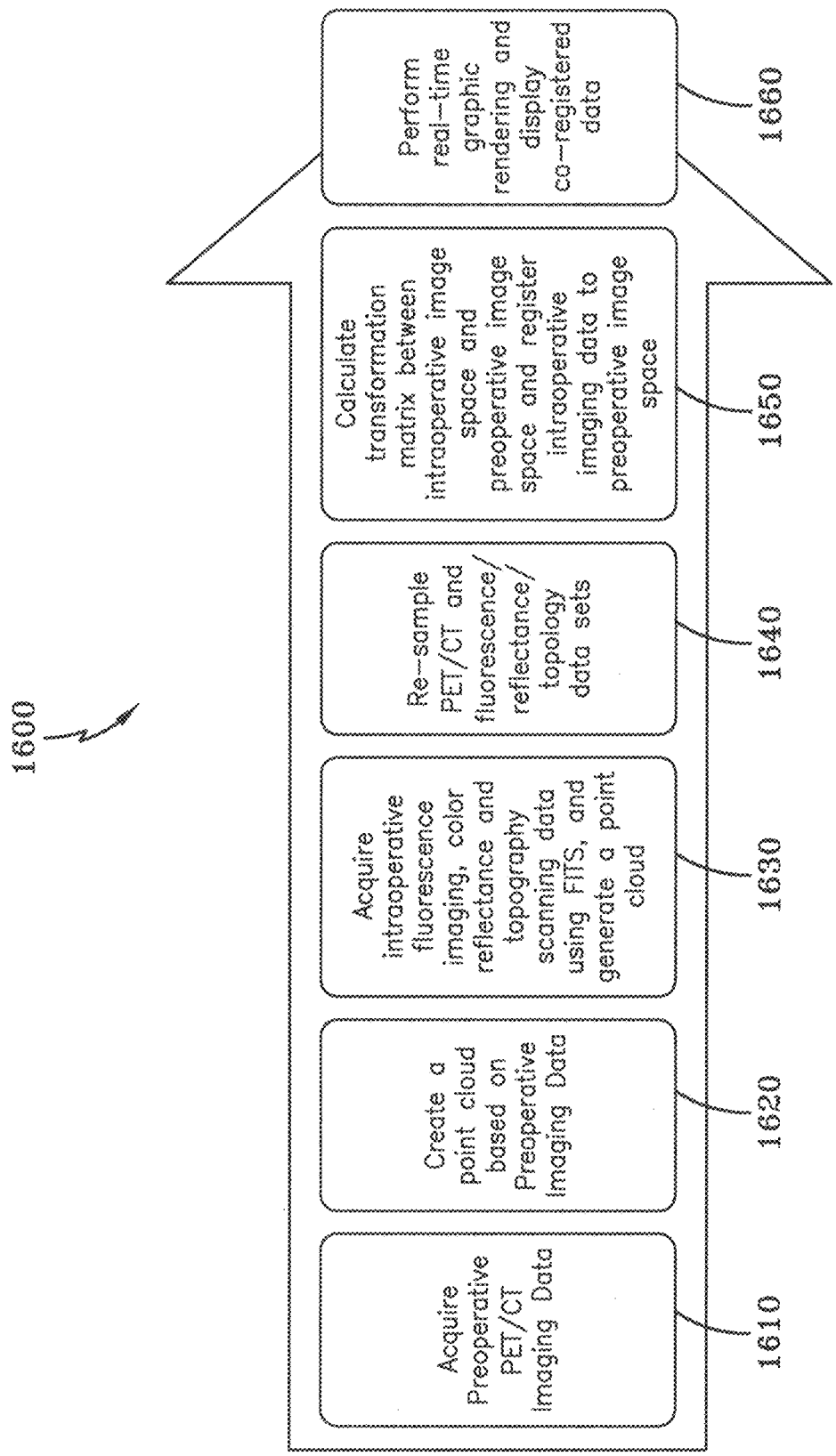
FIG. 19 is a flow diagram showing the steps taken by the optical imaging system to display co-registered images in accordance with the concepts of the present invention.

Furthermore, the present invention overcomes the limitations of prior art systems that utilize offline manual co-registration by implementing a fast image co-registration algorithm or process 1600 at the control system 130 to offer multimodal image guidance intraoperatively. The steps performed by the algorithm or process 1600 are shown in FIG. 19. Initially, at step 1610, prior to surgery, the surgical target object 324 will undergo a PET/CT scan to acquire preoperative image data. Next, at step 1620, a point cloud $\{P_i=(x_i, y_i, z_i, f_i, r_i, g_i, b_i), i=1, 2, \ldots, N\}$ is then obtained, where the vector $(f_i, r_i, g_i, b_i)$ represents the fluorescence, red, green and blue data associated with individual surface points. At step 1630, the imaging configuration 1500 of the present invention acquires intraoperative imaging data, including topography, fluorescence and color reflectance data, as previously discussed. After re-sampling of the optical and PET/CT data sets at step 1640, the process 1600 continues to step 1650 where the surface-based registration is carried out using the iterative closest point (ICP) algorithm with k-d dimensional trees for minimizing processing time as previously described. It should be appreciated that in some embodiments, the co-registration algorithm may be implemented using any suitable programming language, such as MATLAB or Python. After co-registration, the preoperative PET/CT volumetric data will be incorporated, and the updated point cloud will become $\{P_i=(x_i, y_i, z_i, f_i, r_i, g_i, b_i, p_i, c_i), i=1, 2, N\}$, where the vector $(f_i, r_i, g_i, b_i, p_i, c_i)$ represents the fluorescence, red, green, blue, PET and CT data associated with individual points in the 3D volume. Finally, at step 1660 the co-registered preoperative image data and intraoperative image data is displayed, and in some embodiments displayed in real-time. During the display step 1660, the fluorescence, PET and CT signals will be assigned different pseudocolor schemes in the composite image. It should also be appreciated that the registration process may also be optionally performed based on a polygon mesh representation instead of a point cloud representation. The graphic user interface (GUI) of the present invention is optimized to be suitable for both traditional keyboard/mouse input devices, as well as a touchscreen interface, gesture recognition, voice recognition or any other suitable interface device, thereby providing physicians extended flexibility in how to use the imaging system or configuration 1500 in the clinical settings.

Imaging Goggles with 3D Scanning and Medical Imaging Capabilities In particular, the functions provided by the 3D scanning module 110 and the imaging module 120 may be embodied in an imaging configuration 1700A, as shown in FIG. 20A. In particular, the configuration 1700A includes the light emitter module 310, the image detection module 320, and the emission filter 340, previously discussed with regard to FIG. 4A, with the addition of a wearable display 1710. In particular, the wearable display 1710 is coupled to an output of the controller 130, which is coupled to the light emitter module 310 and the image detection module 320. As such, the topography information and the fluorescence information captured by the imaging configuration 1700A is presented on the wearable display 1710, in the manner to be discussed.

Furthermore, in another embodiment, the 3D scanning module 110 and the imaging module 120 may be embodied in an imaging configuration 1700B, as shown in FIG. 20B. Specifically, the configuration 1700B includes the light emitter module 310, the image detection module 320, the emission filter 340, and the fluorescence excitation filter 410, as previously discussed with regard to FIG. 4B, in addition to the wearable display 1710. In particular, the wearable display 1710 is coupled to an output of the controller 130, which is coupled to the light emitter module 310 and the image detection module 320. As such, the topography information and the fluorescence information captured by the imaging configuration 1700A is presented on the wearable display 1710, in the manner to be discussed. In one aspect, the emission filter 340 and the fluorescence excitation filter 410 are provided as movable filter wheels, as previously discussed.

In a further embodiment, the 3D scanning module 110 and the imaging module 120 may be embodied in an imaging configuration 1700C, as shown in FIG. 20C. Specifically, the imaging configuration 1700C includes the light emitter module 310, the image detection module 320, the emission filter wheel 340, the excitation light source 450 and the fluorescence excitation filter 410, as previously discussed with regard to FIG. 4C, in addition to the wearable display 1710. In particular, the wearable display 1710 is coupled to an output of the controller 130, which is coupled to the image detection module 320. As such, the topography information and the fluorescence information captured by the imaging configuration 1700A is presented on the wearable display 1710, in the manner to be discussed.

In a further embodiment, the 3D scanning module 110 and the imaging module 120 may be embodied in an imaging configuration 1700D, as shown in FIG. 20D. In particular, the configuration 1700D includes the light emitter module 310 the image detection module 320, the fluorescence detection module 510, and the fluorescence emission filter 340, as previously discussed with regard to FIG. 5A, in addition to the wearable display 1710. In particular, the wearable display 1710 is coupled to an output of the controller 130, which is coupled to the light emitter module 310, the image detection module 320 and the fluorescence module 510. As such, the topography information and the fluorescence information captured by the imaging configuration 1700A is presented on the wearable display 1710, in the manner to be discussed.

In a further embodiment, the 3D scanning module 110 and the imaging module 120 may be embodied in an imaging configuration 1700E, as shown in FIG. 20E. In particular, the configuration 1700E includes the light emitter module 310, an image detection module 320, the fluorescence detection module 510, the fluorescence emission filter 340, and the fluorescence excitation filter 410, as previously discussed with regard to FIG. 5B, in addition to the wearable display 1710. In particular, the wearable display 1710 is coupled to an output of the controller 130, which is coupled to the light emitter module 310, the image detection module 320, and the fluorescence imaging module 510. As such, the topography information and the fluorescence information captured by the imaging configuration 1700A is presented on the wearable display 1710, in the manner to be discussed.

In a further embodiment, the 3D scanning module 110 and the imaging module 120 may be embodied in an imaging configuration 1700E, as shown in FIG. 20F. Specifically, the imaging configuration 1700E includes the light emitter module 310, the image detection module 320, the fluorescence detection module 510, the emission filter 340, the excitation light source 450 and the fluorescence excitation filter 410, as previously discussed with regard to FIG. 5C, in addition to the wearable display 1710. In particular, the wearable display 1710 is coupled to an output of the controller 130, which is coupled to the light emitter module 310 and the image detection module 320. As such, the topography information and the fluorescence information captured by the imaging configuration 1700A is presented on the wearable display 1710, in the manner to be discussed.

As such, the imaging configurations 1700A-F of the present invention include the wearable display 1710, which may comprise any suitable display, such as a wearable display that is configured for being attached to and worn by a user. For example, the wearable display 1710 may be included as part of a goggle-type wearable device, which includes a wearable goggle or eye-piece frame that carries the display 1710.

In one aspect, the display 1710 may comprise a single display element suitable for providing a single, continuous display that provides a single display surface that encompasses the totality of the user's field of view, or portion thereof. Alternatively, the display 1710 may include multiple separate display elements, such as a dedicated right display and a dedicated left display, such as in the case of a stereoscopic display, which provides independent displays, to provide a field of view for each user's eye.

Furthermore, the display 1710 may comprise a Liquid crystal on silicon (LCoS) display, an LCD (liquid crystal display) display, an OLED (organic light emitting diode) display, a projection display, a head-mounted display (HMD), a head-mounted projection display (HMPD), an optical-see through display, a switchable optical see-through display, a selective occlusion see-through head-mounted display, and a video see-through display. Furthermore, the display may comprise an augmented reality window, augmented monitors, a projection on the patient/projective head-mounted display, selective occlusion see-through head-mounted display, a retinal scanning display, or any other suitable display. In another aspect, the display 1710 may be configured to display any static or moving image. The display 1710 may also comprise a picture-in-picture (PIP) display that can display images from multiple independent image sources simultaneously. In one example, the ultrasound image and intraoperative merged fluorescence & topography image may be displayed in a picture-in-picture fashion. In another example, preoperative tomographic images, and intraoperative color images may be merged with topography and displayed in a picture-in-picture fashion.

In some embodiments, the preoperative tomographic images (e.g. MRI, CT, SPECT, and PET) may be co-registered with intraoperative color image, fluorescence images and topographic data, and shown in the display 1710.

In other embodiments, the display 1710 may comprise a stereoscopic display that is capable of displaying stereoscopic images with depth perception. In further embodiments, the display 1710 may be capable of displaying 3-dimensional (3D) images with depth perception. In still other embodiments, the display 1710 may be configured to provide overlaid or superimposed images of various opacity/transparency to allow simultaneous viewing of multiple images on the display 1710 at one time. In yet another embodiment, the display 1710 may be at least partially light transparent to allow a user to view the image being displayed by the display 1710, while simultaneously allowing the user to directly see with their eyes or natural vision through the display 1710 to also view the user's surrounding environment.

In other embodiments, the fluorescence imaging module 510 comprises a camera that is configured to capture red, green, and blue color information, as well as depth information or data and fluorescence imaging information.

In another aspect, the system 100 may capture 3D topography and fluorescence information of the target object 324 sequentially. To achieve this, the system 100 performs 3D scanning first, and then fluorescence imaging second.

In another aspect, the system may capture 3D topography and fluorescence information of the target object 324 concurrently or simultaneously. As such, the image detection module 320 is able to detect both a 3D scanning signal and fluorescence signals during a similar timeframe. Thus, the image frames captured by the image detection module 320 may be designated for the purpose of 3D scanning and fluorescence imaging, respectively. For example, if the frame rate of the image detection module 320 is 30 frames-per-second (FPS), during a one second period 15 frames (e.g. odd frames: 1, 3, 5, 7, 9 . . . ) can be used for capturing 3D topography, while the remaining 15 frames (e.g. 2, 4, 6, 8, 10 . . . ) can be used for fluorescence detection. It should be appreciated that any other combination of image frame designation may be used for concurrent/simultaneous scanning, for example two-thirds of the total image frames may be used for 3D scanning, while one-third of the total image frames are used for fluorescence imaging.

It should also be appreciated that the operation of the light emitter 310 and the image detection module 320 are coordinated by the operation of frame synchronization by the controller 130. For example, if the image detection module 320 is operating at 30 frames-per-second (FPS), the light emitter 310 is able to emit a fringe pattern for capturing 3D topography for 15 frames (e.g. odd frames 1, 3, 5, 7, 9 . . . ) in synchronization with the image detection module 320. The light emitter module 310 is also configured to emit a fluorescence excitation light for fluorescence imaging the remaining 15 frames (e.g. odd frames 1, 3, 5, 7, 9 . . . ) in synchronization with the detector 320.

The imaging configurations 1700A-F of the present invention can enable various optical imaging techniques. In yet another embodiment, the emission filter 340 may comprise a tunable filter. The use of the tunable filter allows hyperspectral imaging to be performed by the configurations 1700A-F to capture multiple light wavelengths. In yet another embodiment, the emission filter 340 may comprise a filter wheel that includes a plurality of narrow-band filters. As such, the configurations 1700A-F are able to capture multiple light wavelengths of reflectance images or absorption images. In yet another embodiment, the filter wheel embodying the emission filter 340 may comprise filters that are suitable for imaging oxygen saturation. For example, images of tissue oxygen saturation (STO2) or venous oxygen saturation (SVO2) may be measured. For example, 660 nm and 950 nm filters may be used to capture the oxygen saturation image. The oxygen saturation can be calculated using the equation: StO2=value of oxygen-saturated hemoglobin/total hemoglobin value (unsaturated+saturated). It should also be appreciated that Cerenkov imaging may also be enabled by using the appropriate filter 340. It should also be appreciated that polarizers may be used instead of spectral filters, and also another polarizer may be placed in from of the light emitter module 310 to enable polarization imaging, and polarization difference/ratio imaging. It should be appreciated that the different imaging modalities previously discussed may be obtained along with 3D scanning, either sequentially or concurrently using the interleaved methods previously described. It should be appreciated that a plurality of imaging modalities may be enabled by the present invention. For example, oxygen saturation imaging, color reflectance imaging, auto-fluorescence imaging and near infrared (NIR) imaging based on extrinsic contrast may be enabled simultaneously, at the same time.

In the system, the connection between the wearable display 1710 and the controller 130 that is coupled to the imaging module 320, the light emitter module 310, the light source, and the fluorescence imaging module 510 may comprise a wired or wireless connection. In some embodiments, the wearable display 1710, imaging module 320 and the light emitter module 310 are enclosed in a uni-body design to be worn by the user. In other embodiments, the imaging module 320, fluorescence imaging module 510, the light emitter 310 and the light source 450 may be mounted on a tripod, while the wearable display 1710 is worn by the user. In some embodiments, the excitation light source 450 for fluorescence excitation may be worn by the user or mounted on a stationary non-moving support.

It should also be appreciated that the controller 130 may comprise a built-in computing device or may be connected to an external computer/tablet computer/smartphone for system control and data processing.

In another example, gyroscopic tracking may be performed using a tracking module that is provided by the system 100. An inertial measurement unit (IMU) may be used for tracking purposes. It should also be appreciated that in addition to the tracking techniques described above, other tracking techniques may be used, such as radio frequency tracking, optical tracking, electro-magnetic tracking, video tracking (pattern recognition), acoustic tracking, mechanical tracking, and/or a combination thereof. In addition, the tracking method employed may utilize rigid body, flexible body or digitizer methods.

It should be appreciated that during the tracking and registration processes the controller 130 performs computations and executes the necessary steps to enable the accurate tracking and registration. In one aspect, the complete registration process may be performed by the following steps. Initially, the process obtains the position of the patient or target object 324, the wearable imaging and display system 100, and a handheld probe as a peripheral coupled to the interface. Next, the system acquires pre-operative imaging data. Next, a 3D model is created based on the pre-operative imaging data. In the next step, the position of the patient is tracked intra-operatively using any suitable technique, such as fiducial markers for example. Next, a transformation matrix is calculated between the pre-operative image space and the intra-operative object space (i.e. patient space). Continuing, the pre-operative image data is registered to the intra-operative object space (i.e. patient space). Next, the intra-operative imaging data is acquired from the imaging system 100, such as fluorescence or color imaging for example. Continuing, the position of the wearable imaging and display system 100 is obtained, using any suitable technique, such as optical tracking or magnetic tracking). Next, the transformation matrix between the intra-operative imaging space (i.e. wearable imaging and display system) and the intraoperative object space (patient space) is calculated. The intra-operative imaging space (such as fluorescence image data) is then registered to the intra-operative object space (i.e. patient space). In addition, the process acquires handheld device imaging or sensing data, such as ultra-sound fiber microscope, and Raman spectroscopy for example. In addition, the position of the hand-held probe, such as an ultrasound fiber, a microscope, and Raman spectroscopy probe is tracked. Next, a transformation matrix is calculated between the hand-held imaging/sensing probe image space and the intra-operative object space (i.e. patient space). Continuing, the hand-held device image space (i.e. ultrasound or microscope) is registered to the intra-operative object space (i.e. patient space). Finally, the co-registered image data is presented on the display 1710 of wearable imaging system 100.

In another aspect, the process may be configured, such that the tracking and registration process is performed without the image data acquired from the hand-held probe. As a result, the process only uses the intra-operative image data acquired by the imaging and display system 100 (i.e. goggle system) and the pre-operative surgical navigation image data.

In yet another aspect, the process may also be configured, such that the tracking and registration process is performed without the pre-operative surgical navigation image data. As a result, the process only uses the intra-operative image data acquired by the imaging and display system 100 (i.e. goggle system) and the image data acquired by the hand-held probe.

It should also be appreciated that in addition to the registration techniques discussed above, other registration techniques may be used, such as point-based registration, surface-based registration, and/or a combination thereof. The registration may comprise either intensity-based, landmark-based registration or feature-based registration. The transformation models used may comprise linear transformation, or non-rigid/elastic transformation. Spatial or frequency domain methods may be used, as well as automatic or interactive methods. The registration process can be performed based on the point cloud representation, the mesh representation, or a combination thereof.

Polarization-Based and Wavelength-Based Optical Scanning at Different Depths

Light of different wavelengths penetrate into the target object 324, such as biological tissues, with different wavelengths. For example, near infrared (NIR) light at 800 nm can penetrate into biological tissues deeper than blue light at 450 nm. Also, when linearly polarized light is used, the outer surface of tissues or target object 324 will reflect the light with polarization state being preserved. In contrast, light that penetrates deeper into tissues of the target object will lose its linear polarization due to the scattering events as photons travel into tissues. These properties can be used to configure the system 100 as a 3D scanning system that can generate topography at different depths (e.g. most outer surface, 0.5 mm under surface, 1 mm under surface).

Thus, in some embodiments the 3D scanning module 110 and the imaging module 120 may be embodied in an imaging configuration 1800A, as shown in FIG. 21A. Specifically, the imaging configuration 1800A includes the light emitter module 310 and the image detection module 320, as previously discussed with regard to FIG. 4A, with the addition of the polarizer 830 and the analyzer 840. In particular, the polarizer 830 is operatively arranged for use in conjunction with the light emitter module 310, while the analyzer 840 is operatively arranged for use with the image detection module 320. Accordingly, during operation of the imaging configuration 1800A, the light emitter module 310 generates light 322 that is processed by the linear polarizer 830 to illuminate the target object 324. In addition, the light reflected by the target object 324 in response to being illuminated is then processed by the analyzer 840 before being detected as topography information of the target object 324. As such, the use of the polarizer 830 and the analyzer 840 by the imaging configuration 1800A allows depth-resolved topography of the target object 324 to be captured. Thus, when the polarization state of the linear polarizer 830 and the analyzer 840 are aligned (i.e. co-polarization) with each other, the image detection module 320 is able to detect the photons that reflected off the most outer surface of the target object 324 to obtain an outer surface topography. Additionally, when the polarization state of the linear polarizer 830 and the analyzer 840 are orthogonal (i.e. cross-polarization) to each other, the image detection module 320 is able to detect the photons that travel into the inner portion of the target object 324 in order to obtain surface topography at a slightly deeper depth within the target object 324.

Furthermore, in other embodiments, the 3D scanning module 110 and the imaging module 120 may be embodied in an imaging configuration 1800B, as shown in FIG. 21B. Specifically, the imaging configuration 1800B includes the light emitter module 310 and the image detection module 320, the linear polarizer 830 and the analyzer 840, as previously discussed with regard to FIG. 21A, with the addition of a pair of spectral filters 1810 and 1810A. In particular, the spectral filter 1810A and the polarizer 830 are operatively arranged for use in conjunction with the light emitter module 310, while the spectral filter 1810 and the analyzer 840 are operatively arranged for use with the image detection module 320. Accordingly, during operation of the imaging configuration 1800A, the light emitter module 310 generates light 322 that is processed by spectral filter 1810A and the linear polarizer 830 to illuminate the target object 324. In addition, the light reflected by the target object 324 in response to being illuminated is then processed by the analyzer 840 and spectral filter 1810 before being detected as topography information of the target object 324. Thus, when the spectral filters 1810 and 1810A are used in combination with polarizer 830 and analyzer 840, depth resolved topography of the target object 324 in a layered fashion can be achieved. For example, band-pass filters centered at about 400 nm, 500 nm, 600 nm, 700 nm, 800 nm can be placed in 2 filter wheels, whereby each filter wheel has a set of filters of 400 nm, 500 nm, 600 nm, 700 nm, 800 nm, such that one filter wheel is in operative arrangement with the image detection module 320 and the other filter wheel is in operative arrangement with the light emitter module 310. When the analyzer 840 and the polarizer 830 are in a cross-polarization configuration, which permits orthogonal polarization states, the topography of the target object 324 can be scanned when both image detection module 320 and the and light emitter module 310 are both using the spectral filters 1810 at the certain wavelength (e.g. both are using 400 nm filters, then both use 500 nm filters; then both use 600 nm filters, etc.). As a result, depth resolved topography of the target object 324 can be obtained. The longer the wavelength, the deeper the depth where the topography of the target object 324 will be scanned. As such, the details of the target object 324 at different wavelengths can be obtained. It should be appreciated that tunable filters can be used instead of filter wheels of narrow band filters.

In addition to topography image data, reflectance images at different wavelengths (e.g. 400 nm, 500 nm, 600 nm, 700 nm, etc.) can be obtained using the configuration 1800A. As the longer wavelengths penetrate deeper into the biological tissues or other media, longer wavelength reflectance image data (e.g. 800 nm image) carries more information about the target object 324 in its deeper layers than the short wavelength reflectance image data (e.g. 400 nm image). As such, subtraction of the two images obtained for different illumination wavelengths following normalization cancels out most of the image information arising from photons that were reflected before reaching the deeper depth where the embedded object is located. It should be appreciated that different illumination wavelengths may be created by having light emitter module 310 emit light 322 that is processed by different spectral filters 1810A. For example, if the 400 nm reflectance image is expressed as $I_{400}(x,y)$ and the 800 nm reflectance image is expressed as $I_{800}(x,y)$, the normalized difference image (NDI) can be mathematically represented as $I_{NDI}(x,y)=I_{800}(x,y)-A \cdot I_{400}(x,y)$, where $I_{NDI}(x,y)$ is the normalized difference image (NDI) and A is the normalization coefficient to cancel out most of the common information due to the objects at shallower penetration depth. In one aspect, the A will be calculated iteratively based on the similarities between $I_{800}(x,y)$ and $I_{400}(x,y)$. It should be appreciated that A can be a matrix of different values at different pixel locations. As such, the equation for the NDI image can be expressed as $I_{NDI}(x,y)=I_{800}(x,y)-A(x,y) \cdot I_{400}(x,y)$.

Projection of Fluorescence Information onto Tissue Surface of Target Object

It should be appreciated that prior generation image projection systems suffered from problems associated with the accurate projection of image information onto a non-flat surface, as such prior generation systems were designed to work with only with a flat surface. As such, when prior generation image projection systems are required to project images onto a non-flat, or curved surface, the projected image becomes distorted. That is, because typical projectors produce a larger image at a further distance than at a smaller distance, the non-flat projection surface, such as the target object 324, introduces different projector-to-surface distances throughout different parts of the surface, which must be taken into account to ensure that the image projected onto a curved projection surface is sharp, and without distortion.

To overcome this problem of current projection systems, the system 100 of the present invention takes into account the surface of the object, such as the target object 324, onto which an image is to be projected using a projection mapping process. Specifically, projection mapping process provided by the system 100 processes the image information to be projected based on the 3D shape of the surface upon which the image information is to be projected upon, such as the target object 324. In addition, the projection mapping process analyzes and calculates the relative distances between the image projector and various portions/points/regions of the non-flat surface to be projected with images, such as the target object 324. Based on the distance calculation, the system 100 generates a corrected image that takes the surface geometry of the surface onto which the image is to be projected (target object 324) into account, so that the distortion of the projected image that is observed by the user is reduced or minimized.

Thus, in one embodiment of the system 100, the 3D scanning module 110 and the imaging module 120 may be embodied in an imaging and projection configuration 1900A, as shown in FIG. 22A. In particular, the configuration 1900A includes the light emitter module 310 and the image detection module 320, as previously discussed, however, the light emitter module 310 is configured to perform both surface scanning of the target object and to perform image projection for user visualization. The present invention is different from previous projection mapping technologies that processes the projection patterns based on 3D models created by a separate 3D scanner before the projection, as the present invention allows concurrent or simultaneous 3D scanning and image projection. Specifically, the frames of the light emitter module 310 when operating as an image projector can be interleaved. For example, if the total frame rate of the projector is 60 frames-per-second (FPS), ½ of the total frames (odd frames) may be used for 3D scanning, while the remaining ½ of total frames (even frames) are used for projection of images or videos onto a non-flat surface. To minimize confusion to the eyes of a viewer of the target object 324, the 3D scanning frames of the target object 324 collected by the image detection module 320 may use near-infrared (NIR) wavelengths for illumination by the light emitter module 310 that are invisible to the eye of a viewer of the target object 324, while the projection of the image/video back onto the target object 324 by the projection function of the light emitter module 310 may be performed using visible wavelengths.

In another embodiment of the system 100, the 3D scanning module 110 and the imaging module 120 may be embodied in another imaging and projection configuration 1900B, as shown in FIG. 22B. In particular, the configuration 1900B includes the light emitter module 310 and the image detection module 320, as discussed with regard to FIG. 22A, however the image detection module 320 is configured as a depth camera or 3D scanner. As such, the depth camera or 3D scanner provided by the image detection module 320 is able to obtain surface topography and a 3D model of the target object 324, which is then used for processing of the images to be projected by the light emitter module 310 that is configured as the projector. Thus, when imaging a dynamic scene, which includes fast moving objects, sport scenes, and images as seen from a car's point of view, the projection mapping process is performed by the configuration 1900B in real-time based on the data obtained from the depth camera of the image detection module 320. It should be appreciated that any depth camera or 3D scanner can be used by the image detection module 320. Specifically, the depth camera or 3D scanner 320 may utilize various topography scanning methods, including but not limited to conoscopic holography, modulated light, stereo camera, Fourier 3D scanning, low coherence interferometry, common-path interference 3D scanning, and contact profilometers.

In another embodiment of the system 100, the 3D scanning module 110 and the imaging module 120 may be embodied in another imaging and projection configuration 1900C, as shown in FIG. 22C. In particular, the configuration 1900C includes the image detection module 320 and the light emitter module 310, as previously discussed with regard to FIG. 22B, with the addition of another light emitter module 310A. As such the light emitter module 310 is configured to perform 3D scanning functions, while the light emitter module 310A functions as an image projector of images back onto the target object 324 using image projection mapping previously discussed.

In another embodiment of the system 100, the 3D scanning module 110 and the imaging module 120 may be embodied in another imaging and projection configuration 1900D, as shown in FIG. 22D. In particular, the configuration 1900D includes the image detection module 320 and the light emitter module 310, as configured in configuration 1900A discussed with regard to FIG. 22A, with the addition of the fluorescence emission filter 340 and the fluorescence excitation filter 410. In particular, the emission filter 340 is operatively arranged for use in conjunction with the image detection module 320 and the excitation filter 410 is operatively arranged for use in conjunction with the light emitting module 310. It should also be appreciated that both the emission filter 340 and the excitation filter 410 may be configured as filter wheels, such that the emission filter 340 may be selectively moved into or out of the light detection path of the image detection module 320 and the excitation filter 410 may be selectively moved into or out of the light emission path of the light emitting module 310. As such, configuration 1900D allows fluorescence imaging by the imaging detection module 320 to be enhanced when the excitation filter 410 and the emission filter 340 are used.

In another embodiment of the system 100, the 3D scanning module 110 and the imaging module 120 may be embodied in another imaging and projection configuration 1900E, as shown in FIG. 22E. In particular, the configuration 1900E includes the image detection module 320, the light emitter module 310, the fluorescence emission filter 340, and the fluorescence excitation filter 410, as previously discussed with regard to FIG. 22D, with the addition of the excitation light source 450. In particular, the excitation light source 450 is configured to be used in conjunction with the excitation filter 410 during the capturing of fluorescence information of the target object 324 by the emission filter 340 and image detection module 320. It should also be appreciated that both the emission filter 340 may be configured as filter wheel, which can be selectively moved into and out of the light detection path of the image detection module 320. As such, configuration 1900E allows fluorescence imaging by the imaging detection module 320 to be enhanced when the excitation filter 410 and the emission filter 340 are used.

In another embodiment of the system 100, the 3D scanning module 110 and the imaging module 120 may be embodied in another imaging and projection configuration 1900F, as shown in FIG. 22F. In particular, the configuration 1900F includes the image detection module 320 and the light emitter module 310, the fluorescence emission filter 340 and the fluorescence excitation filter 410, as discussed with regard to FIG. 22D, with the addition of the additional light emitter module 310A. In particular, the light emitter module 310 is configured as a light projector for 3D scanning, while the light emitter module 310A is configured as an image projector, as discussed with regard to FIG. 22C. In particular, the emission filter 340 is operatively arranged for use in conjunction with the image detection module 320 and the excitation filter 410 is operatively arranged for use in conjunction with the light emitting module 310. It should also be appreciated that both the emission filter 340 and the excitation filter 410 may be configured as filter wheels, such that the emission filter 340 may be selectively moved into or out of the light detection path of the image detection module 320 and the excitation filter 410 may be selectively moved into or out of the light emission path of the light emitting module 310. As such, configuration 1900F allows fluorescence imaging by the imaging detection module 320 to be enhanced when the excitation filter 410 and the emission filter 340 are used.

Vein Imaging

The system 100 may also be configured to facilitate imaging of a location where a human or animal vein target object 324 is located to facilitate intravenous placement of a needle or injection. To enable this imaging function, another embodiment of the system 100, including the 3D scanning module 110 and the imaging module 120 may be embodied in an imaging and projection configuration 2000A, as shown in FIG. 23A. In particular, the configuration 2000A includes the light emitter module 310 and the image detection module 320, whereby, the light emitter module 310 is configured to perform both 3D surface scanning of the target object and to perform image projection for user visualization, as previously discussed with regard to FIG. 22A, with the addition of an infrared light source 450. However, it should be appreciated that the infrared light source 450 may comprise any suitable light source with other wavelengths. In particular, the imaging configuration 2000A includes transmission imaging geometry, whereby the infrared light source 450 and the image detection module 320 are positioned on different or opposite sides of the tissues or target object 324, whereby the portion 2020 of the emitted IR light 2030 that light passes through the tissue is imaged by the image detection module 320. Red, near-infrared or infrared wavelength is preferred for this application as they penetrate deeper into biological tissues of the target object 320. The system captures the 3D shape of the target object 324 and the projector 310 projects the images back to the biological tissues, or target object 324, such as hands. As such, the vein and vasculatures of the target object hand 324 may be displayed back onto the target object tissues 324 to guide IV injection. The projector 310 also splits imaging frames between topography scanning of the target object 324 and image projection back onto the target object 324 in an interleaved manner, as previously discussed. The camera also splits imaging frames between transmission mode imaging and topography scanning. For example, the image detection module 320 and projector provided by the light emitter module 310 can synchronize their frame rate at 60 fps and share the same clock signal. For odd imaging frames (1, 3, 5, 7 . . . ), the projector 310 and the image detection module 320 work together to produce topography scanning of the target object 324. For even imaging frames (2, 4, 6, 8, . . . ), the image detection module 320 works with the light source 2010 to generate a transmission mode imaging (e.g. vein imaging in hand 324), and the projector 310 projects the processed image back onto the target object tissues 324 for visualization by the eyes of a viewer. It should be appreciated that the projected images are processed based on the 3D shape the target tissue surface 324 to minimize distortion. It should be also appreciated the configuration. 2000A may be used to image attenuation within any objects such as other organs, tissues or plastic parts, instead of imaging vasculatures.

Figure 23B:
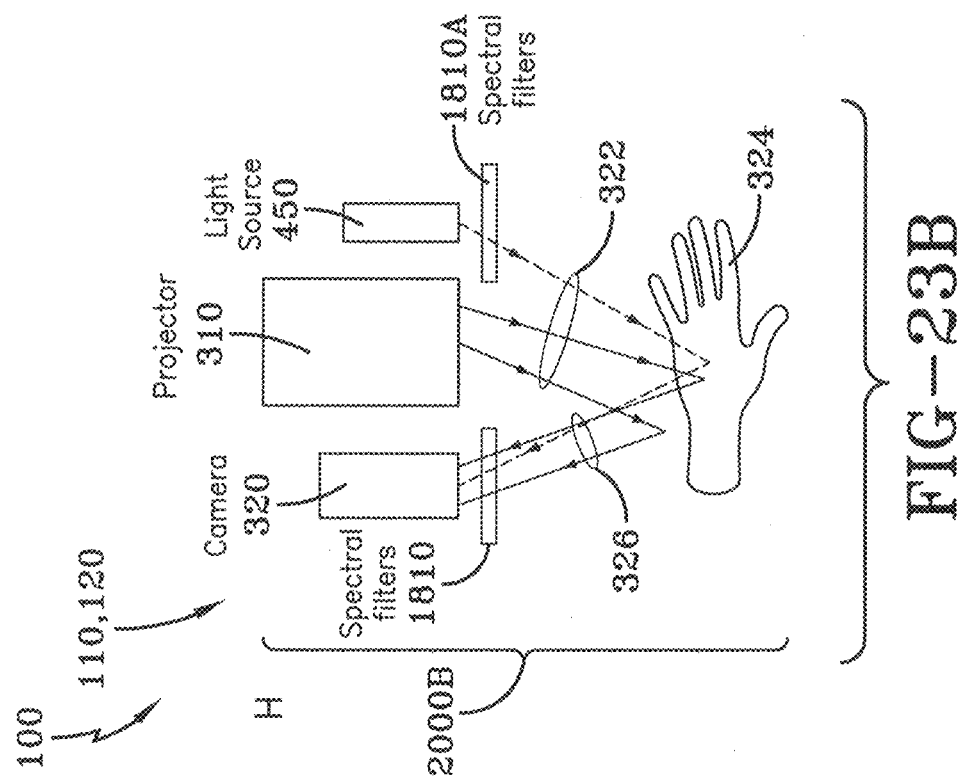
FIG. 23B is a block diagram of another configuration of the optical imaging system in accordance with the concepts of the present invention.
Figure 23A:
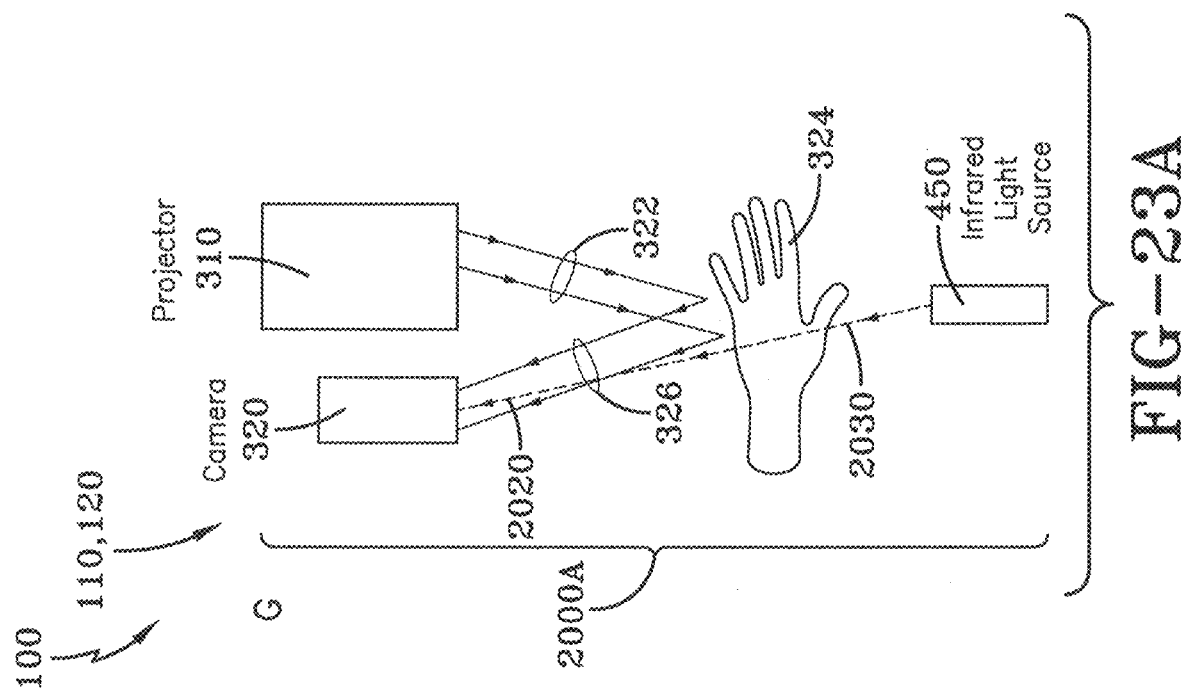
FIG. 23A is a block diagram of one configuration of the optical imaging system in accordance with the concepts of the present invention.

In another embodiment, the system 100, including the 3D scanning module 110 and the imaging module 120 may be embodied in an imaging and projection configuration 2000B, as shown in FIG. 23B. In particular, the configuration 2000B includes the light emitter module 310, the image detection module 320 and the light source 450 whereby, the light emitter module 310 is configured to perform both 3D surface scanning of the target object and to perform image projection for user visualization, as previously discussed with regard to FIG. 23A. In addition, the light source 450 and image detection module 320 are both placed in operative arrangement with respective spectral filters 1810 and 1810A of various wavelengths. For example, both of the spectral filters 1810 and 1810A may be coupled with filters wheels, each of which also include sets of bandpass filters centered at 400 nm, 500 nm, 600 nm, 700 nm, 800 nm. In operation, both the light source 450 and image detection module 320 may both use 400 nm filters to capture an image of the target object 324, and capture the 500 nm, 600 nm, 700 nm, 800 nm images in a similar fashion. If desirable, the normalized difference image (NDI) may be mathematically represented as $I_{NDI}(x,y)=I_{800}(x,y)-A \cdot I_{400}(x,y)$, where $I_{NDI}(x,y)$ is the normalized difference image (NDI) and A is the normalization coefficient to cancel out most of the common information due to the objects at shallower penetration depth. It should be appreciated that any wavelengths can be chosen for multispectral imaging to facilitate imaging of specific biological structures or diseases. Similar to the examples previous discussed, the image detection module 320, the projector 310 and the light source 450 will be synchronized and frames will be interleaved to allow concurrent multispectral imaging and topography scanning.

Projection Mapping and Distortion Compensation

The 3D shape and depth for the non-flat surface to be projected upon, such as the target object 324, enables processing of images to achieve optimized projection and to minimize image distortion of the projected image. Thus, the 3D mod& of the target object 324 captured and generated by the present invention is linked to the physical non-flat target object 324 by a spatial transform, which maps individual points in real-time from the 3D model to the projection surface of the target object 324 so that the image of the 3D model is projected accurately onto the non-flat physical target object 324 surface with a one-to-one correspondence. The spatial transformation is calculated and processed by any suitable computing system, including the controller 130, or any suitable computer system connected thereto by a wireless or wired connection. The spatial transformation calculation uses a transformation T between a 3D model space $X_m$, an object space $X_o$, and an image space $X_i$ on the projection surface of the target object 324 using Cartesian coordinates of a point (x,y,z) that are represented by (xw, yw, zw, w), wherein w is a scalar factor. It should be understood that this calculation can be done on a central processing unit (CPU) or graphics processing unit (GPU), or a combination thereof, or any suitable computing system, such as that previously discussed. The transformation T is a one-to-one mapping process, which includes the transformation $T_1$ from the 3D model space $X_m$ to the object space $X_o$ and the transformation $T_2$ from the object space $X_o$ to the image on the object surface X. The transformation T rotates, scales, reflects, and shears the 3D model to the target object 324 in the object space using the coordinates formulated for $T_1$ and $T_2$, consistent with standard image manipulation techniques. The $T_1$ and $T_2$ are governed by the following equations 1-3:

$$T_1 * X_m = X_o, \qquad \text{Eq. (1)}$$

$$T_2 * X_o = X_i, \qquad \text{Eq. (2),}$$

wherein $X_m$, $X_o$, and $X_i$ are column vectors of 4 dimensions (xw, yw, zw, w) and $T_1$ and $T_2$ are 4×4 matrices.

Combining equation (1) and (2) provides:

$$T_2 * T_1 * X_m = X_i, \quad \text{Eq. (3).}$$

Figure 24:
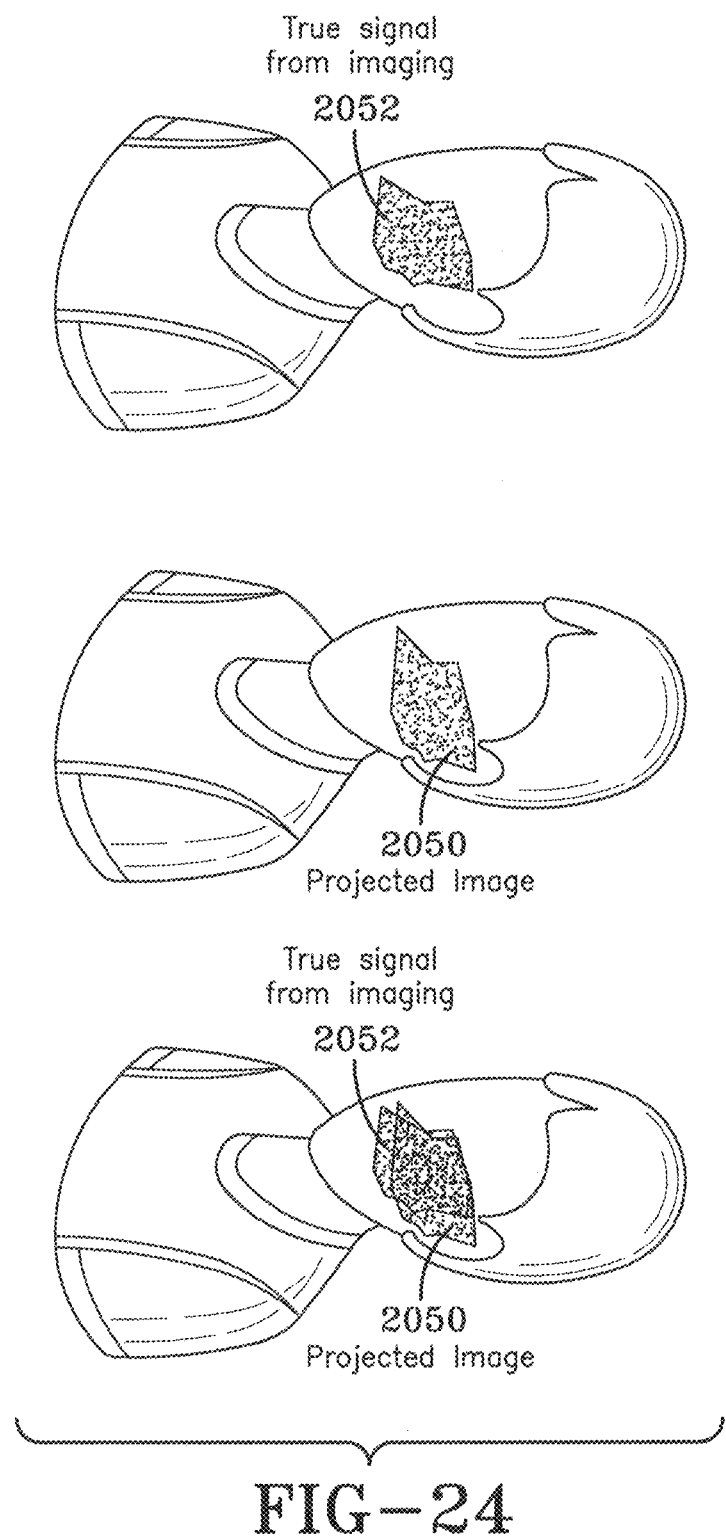
FIG. 24 is a flow diagram showing an imaging and projection process provided by the optical imaging system in accordance with the concepts of the present invention.

Thus, identifying the topography and having the 3D model from the system 100 of the present invention facilitates the calculation of the transformation matrix $T_1$ and $T_2$ for accurate projection mapping, Projection Quality Monitoring, Projection Optimization and Least-Squares Errors The quality of the image projection onto the target object 324 may be monitored in real-time by our system. For example, if a biological tissue lesion or wound is emitting near-infrared (NIR) fluorescence at 830 nm it is imaged by the present invention and projected back to the tissue surface of the target object 324 psedocolored in a color, such as green 2050, as shown in FIG. 24, we can compare the projected image 2050 (in green color) with the true signal 2052 (near infrared signal) for quality monitoring and optimization. Briefly, the points from the true signal Pt(xt,yt) will be compared to corresponding points from the projected image Pp(xp,yp). The NIR and green color can be imaged by the system 100. The correspondences are established based on feature matching and pattern recognition. A vector Vtp may be calculated pointing from Pt(xt, yt) to Pp(xp,yp) (eg. Vtp=Pp(xp,yp)−Pt(xt, yt)). The vector Vtp guides the optimization of the projection mapping by reducing the norm of the vector. Pluralities of mapping point pairs can be used for optimization and least-square error method can be used. For example, if n mapping point pairs (Pp(xp,yp), Pt(xt, yt)) are chosen, the combined square error can be expressed as:

$$\Sigma_{i=1}^{n} [Pp_i(xp,yp) - Pt_i(xt,yt)]^2,$$

wherein $[Pp_i(xp,yp) - Pt_i(xt, yt)]^2$ represents the sum of squared residuals. Optimization is achieved when the system 100 minimizes the sum of the squared residuals, whereby a residual is the difference between the projected image value and the imaging value. In one aspect, the optimization algorithm can be performed on an iterative basis. As such, the iterative algorithm may stop iterations when the calculated squares error sum is smaller than a value that has been predetermined/preset. It should be appreciated that the preset value can be either set manually or by machine learning algorithms that are trained by similar data sets.

It should be appreciated that this optimization can be applied to other optical imaging mechanisms other than fluorescence. For example, the vein imaging systems previously discussed with regard to FIGS. 23A-B may use this optimization algorithm. Similarly, multi-spectral imaging, oxygen saturation imaging with projection mapping on a non-flat surface of the target object 324 can also utilize this algorithm. It should also be appreciated that the real-time monitoring of the projected image on the non-flat surface of the target object 324 provides a technique to monitor projection quality dynamically.

System for Capturing Both 3D Shape Imaging, Fluorescence Imaging, Absorption Coefficient and Scattering Coefficient In another embodiment of the system 100, including the 3D scanning module 110 and the imaging module 120 may be configured, such that the absorption coefficient ($\mu_a$) and the reduced scattering coefficient ($\mu_s'$) may be obtained in addition to fluorescence image data/information and 3D topography data/information. Mapping of the optical properties of biological tissue of the target object 324 using spatial frequency domain imaging (SFDI) may be integrated into the system 100, and carried out by the controller 130, for characterization of the biochemical composition and structure of the target object tissue 324. Modulated imaging is applied to analyze the diffuse reflectance from a spatially-modulated sinusoidal fringe illumination to provide the absorption coefficient ($\mu_a$) and reduced scattering coefficient ($\mu_s'$) maps. An SFDI system comprises an image projector embodied as the light emitter module 310 and the image detection module 320, which are geometrically calibrated.

Figure 25:
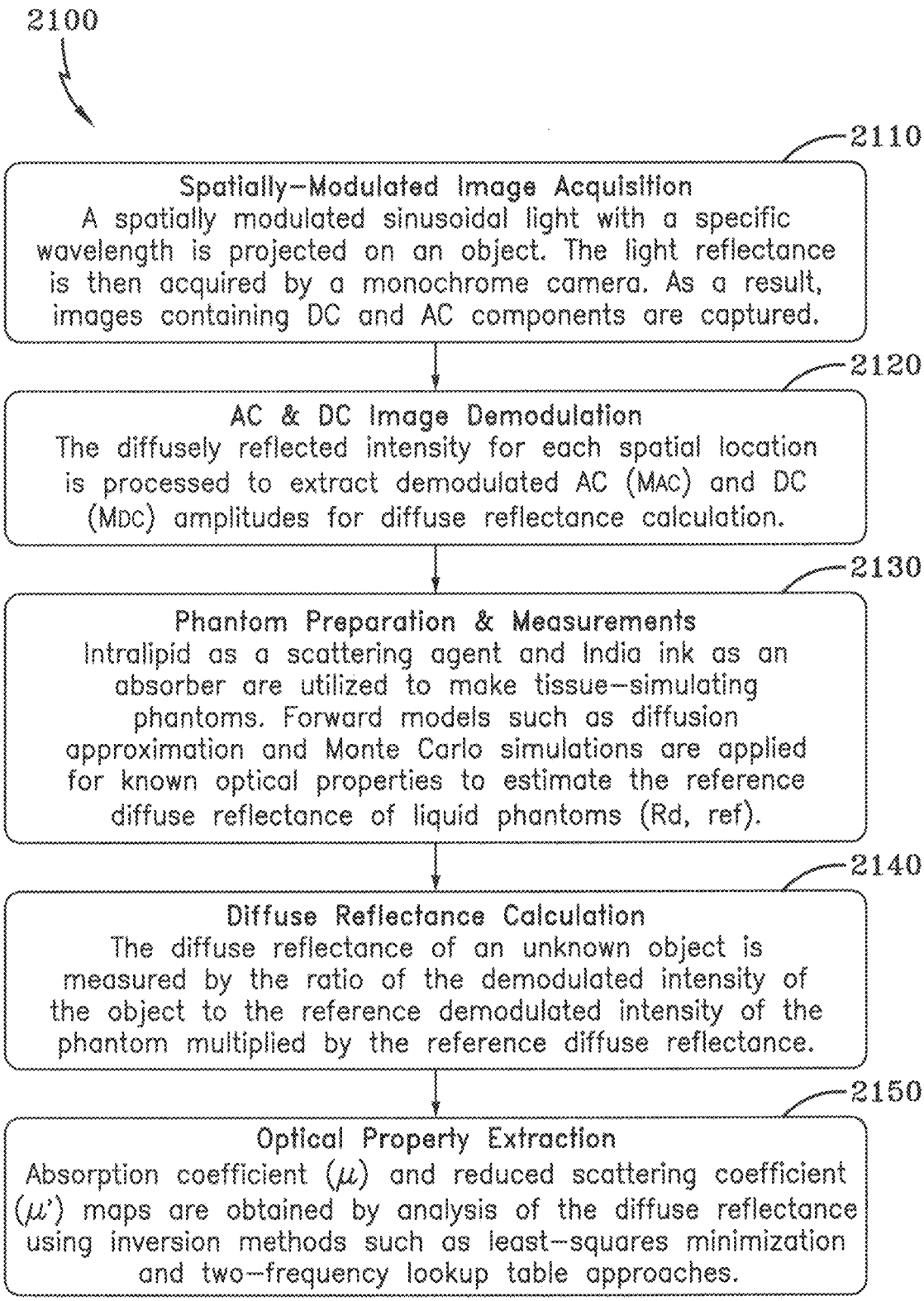
FIG. 25 is a flow diagram showing the steps taken for acquiring optical property maps using spatially-modulated imaging in accordance with the concepts of the present invention.

A procedure or process 2100 steps for acquisition of the optical property maps using spatially-modulated imaging is shown in FIG. 25. In particular, at step 2110, the projector 310 illuminates two grayscale sinusoidal fringe patterns of the target object 324 at different spatial frequencies (fx) with 3 phase shifted by 120 degrees. Sequential illumination of the spatial frequency patterns are controlled by a program running on the controller/computer 130 and filters are used to generate spatial frequency illumination with different wavelengths. The reflected light will be acquired by the image detection module 320 and saved for processing. Low spatial frequency patterns (fx=0) and high spatial frequency patterns are employed to extract the DC and AC components of the diffusely reflected intensity (I), at step 2120. Then, the demodulated AC ($M_{AC}$) and DC ($M_{DC}$) amplitudes will be calculated for each spatial location ($x_i$) as $$M_{AC}(x_i, f_x) = \frac{\sqrt{2}}{3} \sqrt{[I_1(x_i) - I_2(x_i)]^2 + [I_2(x_i) - I_3(x_i)]^2 + [I_3(x_i) - I_1(x_i)]^2} \quad \text{Eq. (4)}$$

$$M_{DC}(x_i) = \frac{1}{3}[I_1(x_i) + I_2(x_i) + I_3(x_i)], \quad \text{Eq. (5)}$$

where, $I_1$, $I_2$ and $I_3$ are the image intensities with shifted spatial phases. Techniques employing transform functions, such as Fourier and Hilbert transforms, allow for the determination of demodulated intensities using a single frame of high spatial frequency patterns, thereby increasing imaging speed significantly and for use in real-time SFDI. The diffuse reflectance of an object (Rd) can be measured from the diffuse reflectance of a turbid phantom (Rd, ref) with known optical properties by:

$$R_d(x_i, f_x) = \frac{M_{AC}(x_i, f_x)}{M_{AC,ref}(x_i, f_x)} R_{d,ref}(f_x), \quad \text{Eq. (6).}$$

Tissue-simulating phantoms are prepared by diluting and blending intralipid as a scattering agent and India ink as an absorber with distilled water, as indicated at step 2130. Reflectance measurements of the homogeneous liquid phantoms with a wide range of absorption and scattering values are performed at step 2140 to acquire demodulated AC ($M_{AC, ref}$) and DC ($M_{DC, ref}$) images. The diffuse reflectance of the phantoms is predicted by applying forward models based on diffusion-based and transport-based approaches, such as diffusion approximation and white Monte Carlo simulations, for given sets of absorption and reduced scattering coefficients. The inversion methods, such as least-squares minimization and two-frequency lookup table approaches are utilized to extract optical properties of the object, as indicated at step 2150. Analysis of the diffuse reflectance for all pixels produces absorption coefficient and reduced scattering coefficient maps which are then processed to merge with 3D models captured by the system.

It should be appreciated that the absorption coefficient ($\mu_a$) and reduced scattering coefficient ($\mu_s'$) images can be registered with fluorescence image, color reflectance image and preoperative images (MRI, CT, SPECT, PET, etc.) using the registration algorithm described previously above.

Deformation Compensation Using Biomechanical Modeling and FEM Modeling

Biological tissues, especially soft tissues, of the target object 324 are likely to deform. If the soft tissues have different deformation between preoperative imaging and intraoperative imaging, registration errors between the images will occur, if deformation is not properly addressed. Accordingly, the present invention allows 3D topography that is captured by the system 100 to be used to update the preoperative images and account for the tissue deformation. Briefly, a surface mesh or volumetric mesh can be generated based on preoperative tomographic imaging data (e.g. MRI, CT, SPECT, PET, 3D ultrasound, OCT, etc.). Image segmentation can be performed to isolate the organ of interest. Features and landmarks can be extracted from both the preoperative image model (based on tomographic imaging data) and the intraoperative image model (3D topography captured by our invention). A first image registration is performed based on the features and landmarks identified. It should be appreciated that the features and landmarks identified tend to have less deformation. After image registration, the closest point distances between mesh nodes of interest and the intraoperatively deformed surface are calculated. It should be appreciated that closest point distances can be calculated based on the mesh data, the point cloud data or a combination thereof. Subsequently, boundary conditions will be generated based on the preoperative image data and the intraoperative image data previously registered. In one aspect, the boundary conditions comprise initial deformations of the tissue/organ of interest associated with mesh nodes or points. Subsequently, the model solutions can be calculated using finite element modeling (FEM) methods using the boundary conditions iteratively (step A). In one aspect, part of the closest point distances are used to determine a displacement boundary condition on the mesh nodes. After each iteration, the locations of new mesh nodes or point clouds of preoperative image data are updated to reflect the mechanical deformation, based on the FEM model solution calculated. Subsequently, a new boundary conditions can be generated and step A can be repeated. It should be appreciated that the partial differential equations are solved with boundary conditions set based on patient anatomy, body force, tissue material properties, etc. As the iterative algorithm is executed, the computer/controller 130 of the system 100 minimizes the least-squares errors for the closest point distances for all mesh nodes or corresponding points. The summation of square errors for all mesh nodes or points can be calculated dynamically and compared to a preset value. The iterative algorithm may stop iterations when the calculated squares error sum is smaller than the preset value. It should be appreciated that the preset value can be either set manually or by machine learning algorithms that were trained by similar data sets. It should be appreciated that the FEM can be performed either on the CPU or the GPU of the computer/controller.

Figure 26:
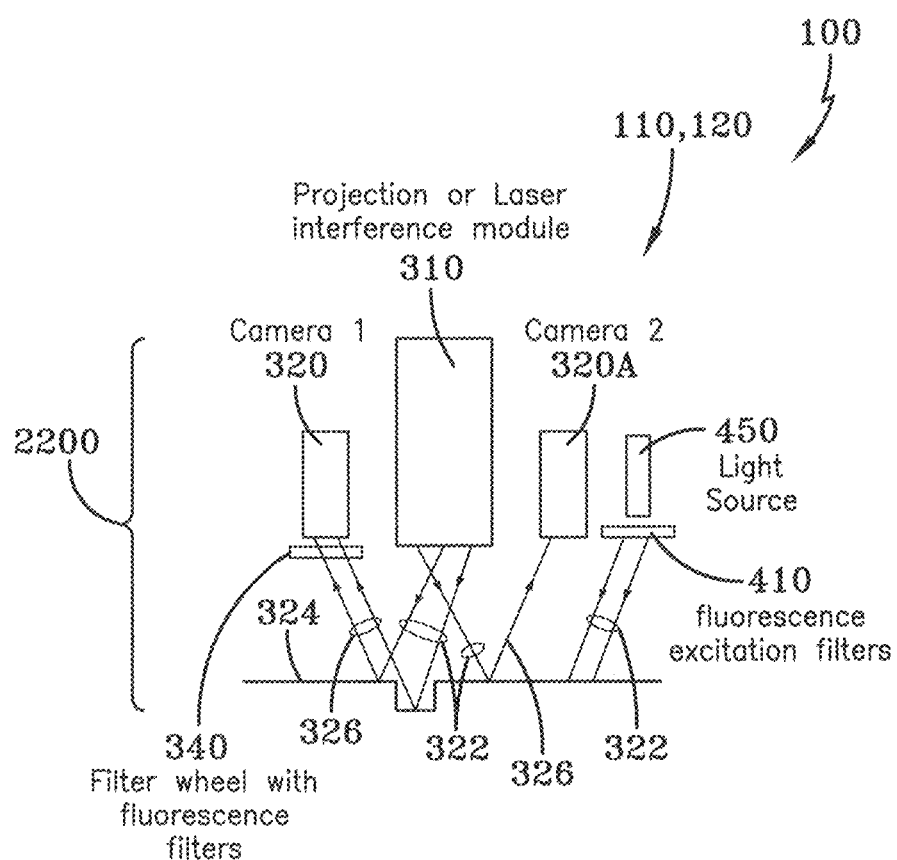
FIG. 26 is a block diagram of one configuration of the optical imaging system in accordance with the concepts of the present invention.

Registration Algorithm Between 2 Image Detectors Based on Topography and Depth Profile In a further embodiment, the 3D scanning module 110 and the imaging module 120 may be embodied in an imaging configuration 2200, as shown in FIG. 26. Specifically, the imaging configuration 2200 includes the light emitter module 310, the image detection module 320, the emission filter 340, the image detection module 320A, and the excitation light source 450 which operates in conjunction with the fluorescence excitation filter 410, as previously discussed with regard to FIG. 4F. Thus, the configuration 2200, as well as other embodiments previously discussed, may use multiple image detection modules 320, in conjunction with 3D scanning and depth sensing capacity provided by the present invention. Thus, the image registration between 2 different image detection modules, 320 and 320A may be optimized based on the depth profile. For example, it is possible to register the images captured by image detector 320 (fluorescence images) to the images captured by image detector module 320A (color images). The transformation matrix for image registration depends on the distance of the target object 324 to the image detector modules 320 and 320A. In the present invention, the distance of the target object 324 is already known. Therefore, the image detector module 320 and the image detector module 320A can be registered using the correct transformation matrix calculated for a fixed distance. For example, transformation matrices may be obtained for various distances and working distances (20 cm, 21 cm, 22 cm, etc.). With the distance/depth of the target object 324 captured by the present invention, the correct transformation matrix may be used for optimized registration results.

In one aspect, the registration matrices at various working distances are calibrated using calibration targets, such as a chessboard pattern. In addition, the transformation matrices at various distances can be obtained during the calibration process. For example, cameras 320 and 320A may image the same calibration target, such as a chessboard pattern, and intersections and/or edges are identified. As such, the common features (e.g. intersections and/or edges) can be used for the calculation of transformation from the image captured by camera 320 to the image that is captured by camera 320A at a given working distance. As the present invention offers depth information and topography data of the objects 324 imaged, the transformation matrices at the correct working distances are identified and used for image registration. For example, if the objects 324 are about 22 cm away from the system 100, the system 100 will detect the depth and use the transformation matrix for 22 cm working distance for image registration between camera 320 and camera 320A.

In another aspect, the registration may be performed between two 2D (two-dimensional) images. The transformation matrix is calculated and processed by the computer/controller 130, which uses a transformation matrix $T_d$ between the image space of the first detector/camera $X_1$ and the image space of the first detector/camera $X_2$ (equation 7), whereby $$T_d * X_1 = X_2 \qquad \text{Eq. (7)}.$$

It should be appreciated that this calculation may be performed on central processing unit (CPU) or graphics processing unit (CPU), or a combination thereof. The transformation T rotates, scales, reflects, and shears the image from detector 320 to register with image from detector 320A. It should also be appreciated that the registration algorithm can be either a rigid registration or a non-rigid registration. Using a calibration pattern, such as chessboard patterns, the transformation matrix $T_d$ at each working distances can be obtained accurately. A set of values such as $\{T_{20}, T_{21}, T_{22}, T_{23}, T_{24}\}$ can be obtained for various working distances (20 cm, 21 cm, 22 cm . . . ) and depths. It should be appreciated that a tolerance range may be assigned to each matrix, whereas T20 can be assigned for a range between 19.1-21.0 cm, and T22 can be assigned to 21.1-23.0 cm. It should be further appreciated that the two image detection modules 320 and 320A may be of different types. For example, image detection module 320 can be a silicon based CCD/CMOS camera for color imaging and image detection module 320A can be a thermographic camera comprises of elements including, but not limited to indium antimonide, indium arsenide, mercury cadmium telluride (MCT), lead sulfide, lead selenide, amorphous silicon (a-Si), vanadium oxide (VOx), lanthanum barium manganite (LBW), lead zirconate titanate (PZT), lanthanum doped lead zirconate titanate (PLZT), lead scandium tantalate (PST), lead lanthanum titanate (PLT), lead titanate (PT), lead zinc niobate (PZN), lead strontium titanate (PSrT), barium strontium titanate (BST), barium titanate (BT), antimony sulfoiodide (SbSI), and polyvinylidene difluoride (PVDF), In another example, image detector module 320 may be a near infrared (NIR) night vision camera and image detector module 320A may be a thermographic camera, where the two types of images may be co-registered based on the distance of the object of interest 324 from system 100.

Depth-Region-Based-Registration

In some circumstances, the target objects 324 being imaged are at different depths. For most accurate registration results, a depth-region-based-registration process may be used. Specifically, the images may be segmented into different regions based on the depth profile captured by the system 100. For example, the images can be segmented into 2 regions, where region 1 has an object 20 cm away from the imaging system and region 2 has an object 30 cm away from the imaging system. For each region, the correct transformation matrix will be used, so $T_{20}$ (for 20 cm working distance) will used for registration of region 1 ($X_{1,r1}$) and $T_{30}$ (for 30 cm working distance) will used for registration of region 2 ($X_{1,r2}$). It should be appreciated that the image can be segmented into a plurality of regions, which is more than 2. It should be further appreciated that each region that is segmented may be represented by a new stack of images, where the pixels within the region still preserve the original intensity values, while the pixels outside of the regions may be assigned the intensity value of 0. As a result, the coordinates and dimensions of the images representing each of the regions remain the same, so each region-based image may be readily used with the original registration transformation matrices. In one aspect, One mathematic representation is shown below;

$$T_{d1}*X_{1,r1}=X_{2,r1}, T_{d2}*X_{1,r2}=X_{2,r2}, \ldots, T_{di}*X_{1,ri}=X_{2,ri},$$

wherein $T_{di}$ is the transformation matrix for the ith region, $X_{1,ri}$ is the image space from detector/camera 320 for the ith region, $X_{2,ri}$ is the image space from detector/camera 320 for the ith region. As such, the previously generated stack of images may be transformed using the transformation matrices of the corresponding working distances, Subsequently, the final transformed image may be digitally synthesized by creating a composite image from the transformed stack of images of various working distances.

In one embodiment, the depth-region-based-registration algorithm or process may be carried out using the following process. Initially, the process calibrates the transformation matrices between 2 detectors, such as image detection modules 320 and 320A, at different working distances. Next, the process obtains the depth profile of objects with the imaging field of view. In the following step, the images that are captured by the 2 detectors are segmented based on the depth profile. The process then generates a stack of images of various working distance, with each stack image containing objects 324 ad a given or predetermined depth. Thus, for each stack image of a particular working distance, the process uses the transformation matrix of the corresponding working distance for registration of the images. Finally, the process adds/overlays the transformed stack images together to synthesize the registered final image.

It should also be appreciated that the depth-region-based-registration algorithm or process may be used to register a plurality of images, from more than 2 detectors or imaging devices. It should also be appreciated that the depth-region-based-registration algorithm or process may use depth profile or 3D topography information that is captured by instruments other than that provided by the system 100, such as a 3D scanner or depth camera. The algorithm or process may also operate independently of the use of the image system 100. In one aspect, the depth-region-based-registration algorithm or process may also be used to register a plurality of images using a known depth map or topography profile of the target objects 324, Endoscope Configuration In some embodiments, the system 100 may be embodied in an imaging configuration 2400A, as shown in FIG. 27A. Specifically, the configuration 2400A includes the light emitting module 310, the image detection module 320, the emission filter 340, with the addition of the beam splitter 610, and an imaging probe 2410. As such, the light emitter module 310 is configured to perform both surface scanning of the target object and to perform optical imaging such as fluorescence imaging and color reflectance imaging. Thus, the present invention allows concurrent or simultaneous 3D scanning and optical imaging in a cavity or other places where access is difficult by free space optics.

It should be appreciated that the imaging probe 2410 may be embodied in the form of an endoscope, a laparoscope or any scope that can enter or be placed into cavities within a human, animal, buildings, cars, or any other physical object. In one embodiment, the endoscope configuration of the imaging probe 2410 is similar to embodiments previously discussed, with the additional requirement that the system is miniaturized so that it can fit into a small cavity. Electrical cords with insulation can be used to deliver the power to the imaging probe 2410 via the duct, intestines, surgical ports or other access routes. In particular, light emitter module 310, and the image detection module 320 and emission filter 340, are arranged at an angle to each other, such as a substantially right angle, while the beam splitter 610 is positioned at an oblique angle, such as about a 45-degree angle, relative to the image detection module 320 and the image detection module 320 and the emission filter 340. In addition, the configuration 2400A includes lenses 2420 and 2430, whereby lens 2420 is disposed at one end of the imaging probe 2410 proximate to the beam splitter 610, and the other lens 2430 is positioned at the other end of the imaging probe 2410, distal to the beam splitter 610. As such, lens 2430 is suitably configured to enter the various cavities in which imaging is desired.

As such, during operation of the detection configuration 2400A, the light emitter module 310 emits light 322 to illuminate the target object 324 via the imaging probe 2410, whereupon the light 326 reflected and emitted by the target object 324 in response to being illuminated is passed through the beam splitter 610 for receipt by the image detection module 320 to capture topography and fluorescence data of the target object 324. In some embodiments, the image data may be represented by a display device, such as LCD monitor or a wearable display. In addition, the projector embodied by the light emitter module 310 may also project the fluorescence image detected by the image detection module 320 through the imaging probe 2410 onto the target object 324.

In other embodiments, the system 100 may be embodied in an imaging configuration 2400B, as shown in FIG. 27B. Specifically, the configuration 2400B includes the light emitting module 310, the image detection module 320, the emission filter 340, and the imaging probe 2410, as discussed with regard to FIG. 27A, but without the use of the beam splitter 610. In addition, the configuration 2400B includes an addition imaging probe 2410A that include corresponding lenses 2420A and 2430A with the addition of the beam spotter 610, and an imaging probe 2410. As such, the light emitter module 310 is configured to perform both surface scanning of the target object and to perform optical imaging. Thus, the present invention allows concurrent or simultaneous 3D scanning and optical imaging. Particularly, during operation the imaging probe 2410 is used to capture topography information and fluorescence image information of the target object 324, while the imaging probe 2410A is used for projecting the pattern for 3D scanning onto the target object 324, and provide fluorescence excitation light to the target object 324.

In other embodiments, the system 100 may be embodied in an imaging configuration 2400C, as shown in FIG. 27C. Specifically, the configuration 2400C includes the light emitting module 310, the image detection module 320, the emission filter 340, the beam splitter 610, and the imaging probe 2410, as discussed with regard to FIG. 27k with the addition of the imaging probe 2410A, a lens 2460, the spectral filter 1810 and the light source 450. As such, the light emitter module 310 is configured to perform both surface scanning of the target object and optical imaging, such as fluorescence imaging and color reflectance imaging. As such, during operation of the configuration 2400C, the spectral filter 1810, and the lens 2460 process the light emitted from the light source 450, whereupon the processed light passes through the imaging probe 2410A to illuminate the target object 324. In addition, the light emitter module 310 projects, via the beam splitter 610 and through the imaging probe 2410, the pattern for 3D scanning of the target object 324. In addition, the image detection module 320 receives through the beam splitter 610 the reflected and emitted light from the target object 324 in response to being illuminated, which passes through the internal detection device 2410 imaging probe 2410, as topography and fluorescence information of the target object 324. Thus, the present invention allows concurrent or simultaneous 3D scanning and optical imaging.

It should also be appreciated that the imaging probe 2410 of the configurations 2400A-C may comprise a liquid light guide, relay lens system in lieu of fiber bundles. It should be further appreciated that color endoscopy, fluorescence endoscopy, oxygen saturation endoscopic imaging, hyperspectral endoscopic imaging can be enabled by the present invention, along with 3D surface topography scanning. It should be further appreciated that the endoscopic images can be registered with CT, MRI, PET, SEPCT, and ultrasound images, or any other diagnostic image, using the methods previously discussed. It should be further appreciated that the various 3D scanning techniques described previously, such as laser triangulation or structured light illumination, may be implemented in the endoscope for 3D scanning. Specifically, the topography scanning module forming the light emitter module 310 in the endoscope configuration may be configured to utilize various topography scanning methods, including but not limited to conoscopic holography, modulated light, stereo camera, Fourier 3D scanning, low coherence interferometry, common-path interference 3D scanning, and contact profilometers.

It should also be appreciated that the components of the system 100, including the light emitter module 310, the image detection module 320, the fluorescence detection module 510, the projector 910, the light source 450, as well as the various filters 340 and 410 when implemented as moveable devices, or any other component of the system 100 requiring control, are coupled to, or are otherwise in a wired or wireless communication with, the controller 130. Accordingly, the controller 130, which may be embodied in any suitable computing device, such as a standalone computing device or portable computing device, which has the necessary hardware, software or combination thereof to coordinate and synchronize the operation of the components coupled thereto. Furthermore, in some embodiments, the controller 130 may be configured to communicate through a wired or wireless communication network with a remote computing device (e.g. a portable or standalone computing device) that may be configured to coordinate and synchronize the operation of the components of the system 100, such that the controller 130 serves as an interface between the components of the system 100 and the remote computing device.

Therefore, one advantage of the present invention is that an imaging system is configured to simultaneously obtain topography and optical imaging data such as fluorescence information. Still another advantage of the present invention is that the imaging system enables topography and optical imaging data such as fluorescence information that are collected to be co-registered. Another advantage of the present invention is that a 3D point cloud/polygon mesh of a shape and fluorescence value is generated, which can be readily registered to preoperative imaging data, such as a PET/CT or MRI image data for example. Still another advantage of the present invention is that the imaging system utilizes a surface 3D profile to track surface deformation, and to provide surface-based registration. Still another advantage of the present invention is that the imaging system allows capturing and projecting of information onto a non-even (i.e. uneven, curved, contoured) surface in real-time or near real-time with low spatial latencies. Still another advantage of the present invention is that the imaging system enables accurate registration between multiple images based on topography and depth profile of a target object. Still another advantage of the present invention is that the imaging system enables depth-resolved scanning by using polarization gating and/or multispectral scanning. Still another advantage of the present invention is the imaging system enables a 3D scanning goggle, which can perform optical imaging. Still another advantage of the present invention is that the imaging system enables a 3D scanning endoscope to perform optical imaging.

Thus, it can be seen that the objects of the present invention have been satisfied by the structure and its method for use presented above. While in accordance with the Patent Statutes, only the best mode and preferred embodiments have been presented and described in detail, with it being understood that the present invention is not limited thereto or thereby. Accordingly, for an appreciation of the true scope and breadth of the invention, reference should be made to the following claims.

What is claimed is:

1. An optical imaging system to image a target object, comprising:
   a light source that includes at least one projector and is configured to illuminate the target object with structured light; and
   an image detector configured to capture a three-dimensional (3D) topography image of the target object when reflected light is reflected from the target object when illuminated by the structured light emitted by the light source;
   a preoperative image detector configured to capture a preoperative image of the target object before the target object is positioned to be illuminated by the light source with the structured light;
   a tracker that is configured to track a position of the target object; and
   a controller that includes at least one graphics processing unit (GPU) and is configured to:
      instruct the image detector to capture the 3D topography image of the target object intraoperatively,
      co-register topography information detected from the 3D topography image intraoperatively and preoperative image information detected from the preoperative image detector to generate co-registered topography information and preoperative information, wherein the co-registered topography information and preoperative information is segmented to isolate an organ of interest and surface-based registration, and
      display intraoperatively the co-registered topography information and the preoperative image information to the user via a display.

2. The optical imaging system of claim 1, further comprising:
   a computer topography (CT) detector configured to capture a CT scan image of the target object before the target object is positioned to be illuminated by the light source with light.

3. The optical imaging system of claim 2, wherein the controller is further configured to co-register the topography information detected from the 3D topography image intraoperatively and CT scan image information detected from the CT detector to simultaneously display intraoperatively the co-registered topography information and the CT scan image information to the user via the display.

4. The optical imaging system of claim 1, further comprising:
   a magnetic resonance imaging (MRI) detector configured to capture an MRI scan image of the target object before the target object is positioned to be illuminated by the light emitter module with light.

5. The optical imaging system of claim 4, wherein the controller is further configured to co-register the topography information detected from the 3D topography image intraoperatively and MRI scan image information detected from the MRI detector to simultaneously display intraoperatively the co-registered topography information and the CT scan image information to the user via the display.

6. The optical imaging system of claim 1, further comprising:
   a fluorescence detector configured to capture a fluorescence image of the target object when reflected light is reflected off the target object when illuminated by the light emitted by the light source.

7. The optical imaging system of claim 6, wherein the controller is further configured to co-register the topography information detected from the 3D topography image intraoperatively and the preoperative information detected from the preoperative image detector and fluorescence information detected from the fluorescence image intraoperatively to simultaneously display intraoperatively the co-registered topography information, the preoperative information and the fluorescence information to the user via the display.

8. The optical imaging system of claim 1, wherein the image detector is further configured to capture optical properties of biological tissue of the target object.

9. The optical imaging system of claim 8, wherein the controller is further configured to incorporate optical properties associated with biological tissue of the target object to co-register the topography information detected from the 3D topography image intraoperatively and preoperative information detected from the preoperative image detector to generate the co-registered topography information and the preoperative image information.

10. The optical imaging system of claim 1, wherein the controller is further configured to incorporate a three-dimensional (3D) surface profile from the 3D topography image to track tissue movements of the target object intraoperatively.

11. An optical imaging system to image a target object comprising:
    a light source configured to illuminate the target with structured light;
    an image detector configured to capture a three-dimensional (3D) topography image of the target when reflected light is reflected from the target when illuminated by the structured light emitted by the light source;
    a tracker that is configured to track a position of the target; and
    a controller that includes at least one graphics processing unit (GPU) and is configured to:
       receive a preoperative image of the target, the preoperative image being an image obtained before the target is positioned to be illuminated by the light source with the structured light,
       instruct the image detector to capture the 3D topography image of the target intraoperatively,
       intraoperatively co-register topography information detected from the 3D topography image and preoperative image information from the received preoperative image to generate co-registered topography information and preoperative information, wherein the co-registered topography information and preoperative information is segmented to isolate an organ of interest and surface-based registration, and
       display intraoperatively the co-registered topography information and the preoperative image information to the user via a display.

12. The optical imaging system of claim 11, further comprising:
    a computer topography (CT) detector configured to capture a CT scan image of the target object before the target object is positioned to be illuminated by the light source with light.

13. The optical imaging system of claim 12, wherein the controller is further configured to co-register the topography information detected from the 3D topography image intraoperatively and CT scan image information detected from the CT detector to simultaneously display intraoperatively the co-registered topography information and the CT scan image information to the user via the display.

14. The optical imaging system of claim 11, further comprising:
   a magnetic resonance imaging (MRI) detector configured to capture an MRI scan image of the target object before the target object is positioned to be illuminated by the light emitter module with light.

15. The optical imaging system of claim 14, wherein the controller is further configured to co-register the topography information detected from the 3D topography image intraoperatively and MRI scan image information detected from the MRI detector to simultaneously display intraoperatively the co-registered topography information and the CT scan image information to the user via the display.

16. The optical imaging system of claim 11, further comprising:
   a fluorescence detector configured to capture a fluorescence image of the target object when reflected light is reflected off the target object when illuminated by the light emitted by the light source.

17. The optical imaging system of claim 16, wherein the controller is further configured to co-register the topography information detected from the 3D topography image intraoperatively and the preoperative information detected from the preoperative image detector and fluorescence information detected from the fluorescence image intraoperatively to simultaneously display intraoperatively the co-registered topography information, the preoperative information and the fluorescence information to the user via the display.

18. The optical imaging system of claim 11, wherein the image detector is further configured to capture optical properties of biological tissue of the target object.

19. The optical imaging system of claim 18, wherein the controller is further configured to incorporate optical properties associated with biological tissue of the target object to co-register the topography information detected from the 3D topography image intraoperatively and preoperative information detected from the preoperative image detector to generate the co-registered topography information and the preoperative image information.

20. The optical imaging system of claim 11, wherein the controller is further configured to incorporate a three-dimensional (3D) surface profile from the 3D topography image to track tissue movements of the target object intraoperatively.

* * * * *